US012648547B2

(12) United States Patent
Goldman et al.

(10) Patent No.: US 12,648,547 B2
(45) Date of Patent: Jun. 9, 2026

(54) HUMANIZED CHIMERAS FOR THE PROSPECTIVE ASSESSMENT OF CELL ADDITION AND REPLACEMENT THERAPIES

(71) Applicants:UNIVERSITY OF ROCHESTER, Rochester, NY (US); UNIVERSITY OF COPENHAGEN, Copenhagen (DK)

(72) Inventors: Steven A. Goldman, Webster, NY (US); Ricardo da Costa Barbedo Vieira, Denmark (DK)

(73) Assignees: University of Rochester, Rochester, NY (US); University of Copenhagen, Copenhagen (DK)

( * ) Notice: Subject to any disclaimer, the term of this patent is extended or adjusted under 35 U.S.C. 154(b) by 307 days.

(21) Appl. No.: 18/045,148

(22) Filed: Oct. 8, 2022

(65) Prior Publication Data

US 2023/0292719 A1 Sep. 21, 2023

Related U.S. Application Data

(60) Provisional application No. 63/257,727, filed on Oct. 20, 2021.

(51) Int. Cl.
*A01K 67/0271* (2024.01)
*A61K 35/30* (2015.01)

(52) U.S. Cl.
CPC ...... *A01K 67/0271* (2013.01); *A01K 2207/15* (2013.01); *A01K 2227/105* (2013.01); *A01K 2267/0318* (2013.01)

(58) Field of Classification Search
None
See application file for complete search history.

(56) References Cited

U.S. PATENT DOCUMENTS

| | | | |
|---|---|---|---|
| 5,082,670 A | 1/1992 | Gage et al. | |
| 6,245,564 B1 | 6/2001 | Goldman et al. | |
| 6,497,872 B1 | 12/2002 | Weiss et al. | |
| 7,524,491 B2 | 4/2009 | Goldman et al. | |
| 9,724,432 B2 * | 8/2017 | Goldman ............... | A61K 35/30 |
| 10,279,051 B2 | 5/2019 | Goldman | |
| 10,779,519 B2 | 9/2020 | Goldman et al. | |
| 2003/0223972 A1 | 12/2003 | Goldman et al. | |
| 2004/0029269 A1 | 2/2004 | Goldman et al. | |
| 2008/0233610 A1 | 9/2008 | Thomson et al. | |
| 2010/0156778 A1 | 6/2010 | Yamagishi | |
| 2011/0200588 A1 | 8/2011 | Ikeda et al. | |
| 2012/0276070 A1 | 11/2012 | Musick | |
| 2012/0276636 A1 | 11/2012 | Nakagawa et al. | |

FOREIGN PATENT DOCUMENTS

| | | |
|---|---|---|
| WO | 2007/069666 | 6/2007 |
| WO | 2008/118820 | 10/2008 |
| WO | 2009/006930 | 1/2009 |
| WO | 2009/006997 | 1/2009 |
| WO | 2009/007852 | 1/2009 |
| WO | 2014124087 | 8/2014 |
| WO | 2020167822 | 8/2020 |

OTHER PUBLICATIONS

Ted M. Dawson, Todd E. Golde, Clotilde Lagier Tourenne, Animal Models of Neurodegenerative Diseases, Oct. 21, 2018, Nat Neursci (Year: 2018).*
Kathryn Eve Lewandowski, Recognizing and Treating Bipolar Disorder and Schizophrenia in Adults, Accessed 2023, McLean, Putting People First in Mental Health; Retrieved from URL: https://www.mcleanhospital.org/video/recognizing-and-treating-bipolar-disorder-and-schizophrenia-adults (Year: 2023).*
Hoffman, R. M. (2004). In vivo imaging with fluorescent proteins: the new cell biology. Acta Histochemica, 106(2), 77-87. https://doi.org/10.1016/j.acthis.2004.02.001 (Year: 2004).*
Goldman SA, Nedergaard M, Windrem MS. Modeling cognition and disease using human glial chimeric mice. Glia. Aug. 2015;63(8):1483-93. doi: 10.1002/glia.22862. Epub May 24, 2015. PMID: 26010831; PMCID: PMC4527525. (Year: 2015).*
Hébert JM, Vijg J. Cell Replacement to Reverse Brain Aging: Challenges, Pitfalls, and Opportunities. Trends Neurosci. May 2018;41(5):267-279. doi: 10.1016/j.tins.2018.02.008. Epub Mar. 13, 2018. PMID: 29548515; PMCID: PMC5924639. (Year: 2018).*
Aleksovskai, K. et al., "Systematic Review and Meta-Analysis of Circulating S100B Blood Levels in Schizophrenia," Plos One 9, e106342 (2014).
Bates, G. P. et al. "Huntington Disease," Nat Rev Dis Primers 1: 15005 (2015).
Benraiss, A. et al. "Cell-intrinsic Glial Pathology is Conserved Across Human and Murine Models of Huntington's Disease," Cell Reports 36, 109308 (2021).
Benraiss, A. et al. Human glia can both induce and rescue aspects of disease phenotype in Huntington disease. Nature Communications 7, 11758 (2016).
Bjorklund et al., Neural Grafting in the Mammalian CNS, Ch. 3-8, Elsevier, Amsterdam (1985).
Cai et al., "Generation of Human Induced Pluripotent Stem Cells from Umbilical Cord Matrix and Amniotic Membrane Mesenchymal Cells," J. Biol. Chem. 285 (15):112227-11234 (2110).

(Continued)

*Primary Examiner* — Anna Skibinsky
*Assistant Examiner* — Catherine L Mccormick
(74) *Attorney, Agent, or Firm* — Fox Rothschild LLP

(57) ABSTRACT

A chimeric non-human mammal disease model, wherein (1) at least 30% of all the glial cells in the corpus callosum of the chimeric non-human mammal are human glial cells, and/or (2) at least 5% of all of the glial cells in the white matter of the brain and/or brain stem of the chimeric non-human mammal are human glial cells, and wherein the human glial cells comprise a combination of a first group of human glial cells tagged with a first label and a second group of human glial cells tagged with a second label that is distinguishable from the first label.

18 Claims, 53 Drawing Sheets
(46 of 53 Drawing Sheet(s) Filed in Color)

Specification includes a Sequence Listing.

(56)         References Cited

OTHER PUBLICATIONS

Cambi et al., Neurochem. Res. 19:1055-60 (1994).
Cook et al., "Regulation of Rodent Myelin Proteolipid Protein Gene Expression," Neurosci. Lett. 137(1): 56-60 (1992).
Diaz-Castro, B., et al., "Astrocyte Molecular Signatures in Huntington's Disease," Sci Transl Med 11, eaaw8546 (2019).
Faideau, M. et al. "In Vivo Expression of Polyglutamine-Expanded Huntingtin by Mouse Striatal Astrocytes Impairs Glutamate Transport: A Correlation with Huntington's Disease Subjects," Hum Mol Genet 19: 3053-3067 (2010).
Feng et al., "Reprogramming of Fibroblasts into Induced Pluripotent Stem Cells with Orphan Nuclear Receptor Esrrb," Nat. Cell Biol. 11: 197-203 (2009).
Franklin, R. J. M., et al., "Remyelination in the CNS: from Biology to Therapy," Nat Rev Neurosci 9, 839-855 (2008).
Giorgetti et al.. "Generation of Induced Pluripotent Stem Cells from Human Cord Blood Cells with only Two Factors: Oct4 and Sox2," Nat. Protocol. 5 (4): 811-820 (2010).
Giorgio, F. P. D., et al., "Human Embryonic Stem Cell-Derived Motor Neurons Are Sensitive to the Toxic Effect of Glial Cells Carrying an ALS-Causing Mutation," Cell Stem Cell 3: 637-648 (2008).
Giorgio, F. P. D., et al., "Non-Cell Autonomous Effect of Glia on Motor Neurons in an Embryonic Are Sensitive to the Toxic Effect of Glial Cells Carrying an ALS-Causing Mutation," Cell Stem Cell 3: 637-648 (2008).
Giorgio, F. P. D., et al., "Non-Cell Autonomous Effect of Glia on Motor Neurons in an Embryonic Stem Cell-Based ALS Model," Nat Neurosci 10: 608-614 (2007).
Givogri, M. I. et al., "Oligodendroglial Progenitor Cell Therapy Limits Central Neurological Deficits in Mice with Metachromatic Leukodystrophy," J Neurosci 26, 3109-3119 (2006).
Gloster et al, J. Neurosci. 14:7319-30 (1994).
Wang et al., "Human PSC-Derived Oligodendrocyte Progenitors Can Myelinate and Rescue a Mouse Model of Congenital Hypomyelination," Cell Stem Cell 12(2): 252-264 (2013).
Goldman, S. A., et al., "Modeling Cognition and Disease Using Human Glial Chimeric Mice," Glia 63: 1483-1493 (2015).
Goldman, S. A., "Stem and Progenitor Cell-Based Therapy of the Central Nervous System: Hopes, Hype, and Wishful Thinking," Cell Stem Cell 18, 174-188 (2016).
Han et al., "Forebrain Engraftment by Human Glial Progenitor Cells Enhances Synaptic Plasticity and Learning Adult Mice," Cell Stem Cell 12:342-353 (2013).
Hanna et al., "Direct Reprogramming of Terminally Differentiated Mature B Lymphocytes to Pluripotency" Cell 133 (2):250-264 (2008).
Hoist et al., J. Biol. Chem. 269:22245-52 (1994).
Hu et al., "Efficient Generation of Transgene-Free Induced Pluripotent Stem Cells from Normal and Neoplastic Bone Marrow and Cord Blood Mononuclear Cells," Blood ( 2011).
Huangfu et al., "Induction of Pluripotent Stem Cells from Primary Human Fibroblasts with Only Oct4 and Sox2," Nat. Biotechnol. 26: 1269-1275 (2008).
Katsel, P. et al., "Astrocyte and Glutamate Markers in the Superficial, Deep, and White Matter Layers of the Anterior Cingulate Gyrus in Schizophrenia." Neuropsychopharmacol 36, 1171-1177 (2011).
Keyoung et al.. "High-Yield Selection and Extraction of Two Promoter-Defined Phenotypes of Neural Stem Cells from the Fetal Human Brain," Nat. Biotechnol. 19:843-850 (2001).
Kim et al., "Oct4-induced Pluripotency in Adult Neural Stem Cells," Cell 136 (3): 411-419 (2009).
Kim et al., "Pluripotent Stem Cells Induced from Adult Neural Stem Cells by Reprogramming with Two Factors," Nature 454: 646-650 (2008).
Krebs et al., J. Virol. 69:2434-42 (1995).

Laszkiewicz et al., "Structural Characterization of Myelin-associated Glycoprotein Gene Core Promoter." J. Neurosci. Res. 50(6): 928-36 (1997).
Lee, Y. et al., "Oligodendroglia Metabolically Support Axons and Contribute to Neurodegeneration," Nature 487: 443-448 (2012).
Liu et al., "CD44 Expression Identifies Astrocyte-Restricted Precursor Cells." Dev. Biol. 276:31-46 (2004).
Liu et al., Gene 171 :307-08 (1996).
Meissner et al., "Direct Reprogramming of Genetically Unmodified Fibroblasts into Pluripotent Stem Cells," Nat. Biotech. 25: 1177-1181 (2007).
Meyer, K. et al. "Direct Conversion of Patient Fibroblasts Demonstrates Non-Cell Autonomous Toxicity of Astrocytes to Motor Neurons in Familial and Sporadic ALS." Proc National Acad Sci 111: 829-832 (2014).
Nakagawa et al., Nat. Biotechnol. 26:101-106 (2007).
Nakagawa, et al., "Induction of Pluripotent Stem Cells from Mouse Embryonic Fibroblasts by Oct4 and Kif4 with Small-Molecule Compounds" Cell Stem Cell 3(5): 568-574 (2008).
Nunes et al., "Identification and Isolation of Multipotential Neural Progenitor Cells from the Adult Human White Matter," Soc. Neurosci. Abstr. (2001).
Nunes, M. C. et al., "Identification and Isolation of Multipotential Neural Progenitor Cells from the Subcortical White Matter of the Adult Human Brain," Nat Med 9, 438-447 (2003).
Okita, et al., "Generation of Germline—Competent Induced Pluripotent Stem Cells," Nature 448: 313-317 (2007).
Osipovitch, M. et al., "Human ESC-Derived Chimeric Mouse Models of Huntington's Disease Reveal Cell-Intrinsic Defects in Glial Progenitor Cell Differentiation," Cell Stem Cell 24: 107-122 (2019).
Park et al., "Analysis of Upstream Elements in the HuC Promoter Leads to the Establishment of Transgenic Zebrafish with Fluorescent Neurons," Dev. Biol. 227(2): 279-93 (2000).
Park et al., "Reprogramming of Human Somatic Cells Pluripotency with Defined Factors," Nature 451: 141-146 (2008).
Pluchino et al., "Injection of Adult Neurospheres Induces Recovery in a Chronic Model of Multiple Sclerosis," Nature 422(6933): 678-94 (2003).
Scherer et al., "Differential Regulation of the 2',3'-cyclic nucleotide 3'phosphodiesterase Gene During Oligodendrocyte Development," Neuron 12: 1363-75 (1994).
Shin, J.-Y. et al. "Expression of Mutan Huntingtin in Glial Cells Contributes to Neuronal Excitotoxicity" J Cell Biology 171, 1001-1012 (2005).
Sim, F. J. et al., "CD140a Identifies a Population of Highly Myelinogenic, Migration-competent and Efficiently Engrafting Human Oligodendrocyte Progenitor cells," Nat Biotechnol 29, 934-941 (2011).
Sommer et al., "Experimental Approaches for the Generation of Induced Pluripotent Stem Cells," Stem Cell Res. Ther. 1: 250-264 (2010).
Sommer et al., "Generation of Human Induced Pluripotent Stem Cells from Peripheral Blood using the STEMCCA Lentiviral Vector," J. Vis. Exp. 68: e4327 (2012).
Streckfuss-Bomeke et al., "Comparative Study of Human-Induced Pluripotent Stem Cells Derived from Bone Marrow Cells, Hair Keratinocytes, and Skin Fibroblasts," Eur. Heart J. Sep. 2013;34(33):2618-29. Doi: 10.1093/eurheartj/ehs.203. Epub 2012.
Tabrizi, S. J., et al., "Huntington Disease: New Insights into Molecular Pathogenesis and Therapeutic Opportunities." Nat Rev Neurol 16: 529-546 (2020).
Takahashi et al., "Induction of Pluripotent Stem Cells from Adult Human Fibroblasts by Defined Factors," Cell 131: 1-12 (2007).
Takahashi et al., "Induction of Pluripotent Stem Cells from Mouse Embryonic and Adult Fibroblast Cultures by Defined Factors," Cell 126: 663-676 (2006).
Tkachev, D. et al., "Oligodendrocyte Dysfunction in Schizophrenia and Bipolar Disorder," Lancet 362, 798-805 (2003).
Tong, X. et al., "Astrocyte Kir4.1 Ion Channel Deficits Contribute to Neuronal Dysfunction in Huntington's Disease Model Mice," Nat Neurosci 17, 694-703 (2014).

(56)         References Cited

OTHER PUBLICATIONS

Voineskos, A. N. et al., "Oligodendrocyte Genes, White Matter Tract Integrity, and Cogriltion in Schizophrenia," Cereb Cortex 23, 2044-2057 (2013).

Waldvogel, H. J., et al., "Behavioral Neurobiology of Huntington's Disease and Parkinson's Disease," Curr Top Behav Neurosci 22: 33-80 (2014).

Wang et al., "Human iPSCs-Derived Oligodendrocyte Progenitor Cells Can Myelinate and Rescue a Mouse Model of Congenital Hypomyelination," Cell Stem Cell 12:252-264 (2013).

Wang et al., Prospective Identification, Direct Isolation, and Expression Profiling of a Telomerase Expressing Subpopulation of Human Neural Stem Cells, Using Sox2 Enhancer-directed fluorescence-activated cell sorting. J Neurosci. Nov. 3, 2010;30 (44):14635-48. Doi: 10.1523/JNEUROSCI.1729-10.2010.

Wight et al., "Regulation of Murine Myelin Proteolipid Protein Gene Expression," J. Neurosci. Res. 50(6): 917-27 (1997).

Windrem et al., "Neonatal Chimerization With Human Glial Progenitor Cells Can Both Remyelinate and Rescue the Otherwise Lethally Hypomyelinated Shiverer Mouse," Cell 2:553-56.

Windrem, M. S. et al., "A Competitive Advantage by Neonatally Engrafted Human Glial Progenitors Yields Mice Whose Brains Are Chimeric for Human Glia," J Neurosci 34, 16153-16.

Windrem, M. S. et al., "Human Glial Progenitor Cells Effectively Remyelinate the Demyelinated Adult Brain," Cell Reports 31, 107658 (2020).

Windrem, M. S. et al., "Human IPSC Glial Mouse Chimeras Reveal Glial Contributions to Schizophrenia," Cell Stem Cell 21, 195-208. e6 (2017).

Wrabetz et al., "Analaysis of the Human MBP Promoter in Primary Culture of Oligodendrocytes", J. Nurosci. Res. 36:455-71 (1993).

Yamanaka, K. et al., "Astrocytes as Determinants of Disease Progression in Inherited Amyotrophic Lateral Sclerosis," Nat Neurosci 11: 251-253 (2008).

Yao et al., "Neural Specificity of ELAV Expression: Defining a *Drosophila* Promoter for Directing Expression to the Nervous System," J. Neurochem. 63(1): 41-51 (1994).

Yu et al., "Induced Pluripotent Stem Cell Lines Derived from Human Somatic Cells," Science 318: 1917-1920 (2007).

Zhao et al., "Two Supporting Factors Greatly Improve the Efficiency of Human iPSC Generation," Cell Stem Cell 3:475-479 (2008).

U.S. Appl. No. 18/046,930, filed Oct. 16, 2022, Pending.

U.S. Appl. No. 18/046,928, filed Oct. 16, 2022, Pending.

Bjorklund and Stenevi (eds), Neural Grafting in the Mammalian CNS, Ch. 3-8. Elsevier, Amsterdam (1985).

International Search Report and Written Opinion Issued in International Patent Application No. PCT/US/2022/078182, mail date Jan. 20, 2023.

International Search Report and Written Opinion Issued in International Patent Application No. PCT/US/2022/076161, mail date Mar. 21, 2023.

International Search Report and Written Opinion Issued in International Patent Application No. PCT/US/2022/077825, mail date Jan. 20, 2023.

Mariani, John et al. "Age Associated Induction of Senescent Transcriptional Programs in Human Hlial Progenitor Cells", SSRN Electronic Journal, Sep. 25, 2021, pp. 1-51.

Neumann Bjom et al. "Myc determines the functional age state of oligodendrocyte progenitor cells", Nature Aging. vol. 1 No. 9 Sep. 14, 2021 pp. 826-837.

Lo L-C et al, "V-myc Immortalization of Early Rat Neural Crest Cells Yields a Clonal Cell Line Which Generates Both Cliat and Adrenergic Progenitor Cells" Development Biology, Elsevier Amsterdam vol. 145, No. 1, May 1, 1991 pp. 139-153.

Vieira, R et al., "Young glial progenitor cells competitively replace aged and diseased human glia in the adult chimeric mouse brain," Nature Biotechnology (2024); 42: pp. 719-730.

Moser, A. et al., "Survival of the fittest glia," Nature Biotechnology (2024); 42: pp. 700-702.

* cited by examiner

A

A'

C

| Cell Line | HTT CAG Lenght | Transgenic Insert |
|---|---|---|
| GENEA019 (WT-EGFP) | 18;15 | Puro-CAG-EGFP |
| GENEA019 (WT-mCherry) | 18;15 | Puro-CAG-mCherry |
| GENEA020 (HD-EGFP) | 48;17 | Puro-CAG-EGFP |

WT-mCherry

HD-EGFP

FIG. 2 (Con.)
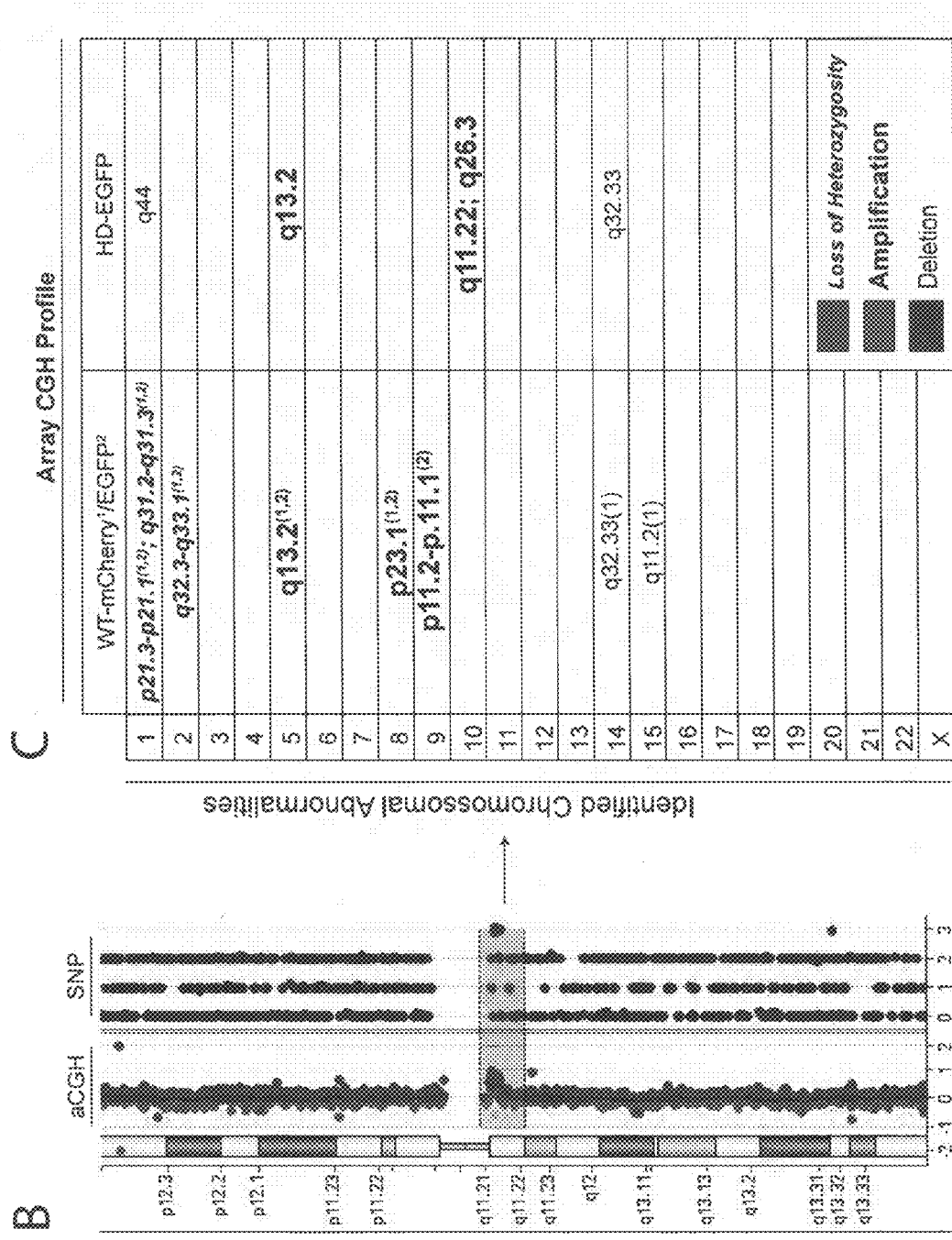

A hESCs
WT-mCherry
HD-EGFP

Directed Differentiation
(Wang et al. 2013)

180 DIV

GPCs
WT-mCherry
HD-EGFP

In vitro Characterization
Morphological Assessment (B)
Phenotypic Characterization (C-D)
- Flow Cytometry (C)
- Immunocytochemistry (D)

Experimental Grafts

A    Identification of TF candidates
with Competititive Advantage

HUMANIZED CHIMERAS FOR THE PROSPECTIVE ASSESSMENT OF CELL ADDITION AND REPLACEMENT THERAPIES

This application claims priority from U.S. Provisional Application No. 63/257,727, filed Oct. 20, 2021, which is incorporated herein by reference.

FIELD

This application relates to humanized chimeras for prospective assessment of cell addition and replacement therapies.

BACKGROUND

Glial dysfunction is a causal contributor to a broad spectrum of neurological conditions. Besides the many disorders of myelin, it is now clear that astrocytic and oligodendrocytic pathology underlie the genesis and progression of a number of both neurodegenerative and neuropsychiatric disorders, including conditions as varied as amyotrophic lateral sclerosis (ALS) (Giorgio, F. P. D., et al., "Non-Cell Autonomous Effect of Glia on Motor Neurons in an Embryonic Are Sensitive to the Toxic Effect of Glial Cells Carrying an ALS-Causing Mutation," Cell Stem Cell 3:637-648 (2008); Yamanaka, K. et al. "Astrocytes as determinants of disease progression in inherited amyotrophic lateral sclerosis," Nat Neurosci 11:251-253 (2008); Lee, Y. et al. "Oligodendroglia Metabolically Support Axons and Contribute to Neurodegeneration," Nature 487:443-448 (2012); and Meyer, K. et al. "Direct Conversion of Patient Fibroblasts Demonstrates Non-Cell Autonomous Toxicity of Astrocytes to Motor Neurons in Familial and Sporadic ALS," Proc National Acad Sci 111:829-832 (2014)) and Huntington's disease (HD) (Shin, J.-Y. et al. "Expression of Mutant Huntingtin in Glial Cells Contributes to Neuronal Excitotoxicity," J Cell Biology 171:1001-1012 (2005); Faideau, M. et al. "In Vivo Expression of Polyglutamine-Expanded Huntingtin by Mouse Striatal Astrocytes Impairs Glutamate Transport: A Correlation with Huntington's Disease Subjects," Hum Mol Genet 19:3053-3067 (2010); Tong, X. et al., "Astrocyte Kir4.1 Ion Channel Deficits Contribute to Neuronal Dysfunction in Huntington's Disease Model Mice," Nat Neurosci 17, 694-703 (2014); Benraiss, A. et al., Human Glia can both Induce and Rescue Aspects of Disease Phenotype in Huntington Disease," Nat Commun 7, 11758 (2016); Diaz-Castro, B., et. al., "Astrocyte Molecular Signatures in Huntington's Disease," Sci Transl Med 11, eaaw8546 (2019); Benraiss, A. et al. "Cell-intrinsic Glial Pathology is Conserved Across Human and Murine Models of Huntington's Disease," Cell Reports 36, 109308 (2021)) as well as schizophrenia and bipolar disease (Tkachev, D. et al., "Oligodendrocyte Dysfunction in Schizophrenia and Bipolar Disorder," Lancet 362, 798-805 (2003); Katsel, P. et al., "Astrocyte and Glutamate Markers in the Superficial, Deep, and White Matter Layers of the Anterior Cingulate Gyrus in Schizophrenia," Neuropsychopharmacol 36, 1171-1177 (2011); Voineskos, A. N. et al., "Oligodendrocyte Genes, White Matter Tract Integrity, and Cognition in Schizophrenia," Cereb Cortex 23, 2044-2057 (2013); Aleksovska, K. et al., "Systematic Review and Meta-Analysis of Circulating S100B Blood Levels in Schizophrenia," Plos One 9, e106342 (2014); Windrem, M.

S. et al., "Human iPSC Glial Mouse Chimeras Reveal Glial Contributions to Schizophrenia," Cell Stem Cell 21, 195-208.e6 (2017).

In such conditions, the replacement of diseased glia by healthy wild-type glial progenitor cells may provide substantial therapeutic benefit (Goldman, S. A., "Stem and Progenitor Cell-Based Therapy of the Central Nervous System: Hopes, Hype, and Wishful Thinking," Cell Stem Cell 18, 174-188 (2016) and Franklin, R. J. M., et. al., "Remyelination in the CNS: from Biology to Therapy," Nat Rev Neurosci 9, 839-855 (2008)) due to the migration and expansion competence of human glial progenitor cells (hGPCs), as well as their lineage plasticity and ability to generate both astrocytes and myelin-forming oligodendrocytes in a context-dependent manner (Nunes, M. C. et al., "Identification and Isolation of Multipotential Neural Progenitor Cells from the Subcortical White Matter of the Adult Human Brain," Nat Med 9, 439-447 (2003); Sim, F. J. et al., "CD140a Identifies a Population of Highly Myelinogenic, Migration-competent and Efficiently Engrafting Human Oligodendrocyte Progenitor cells," Nat Biotechnol 29, 934-941 (2011); Windrem, M. S. et al., "A Competitive Advantage by Neonatally Engrafted Human Glial Progenitors Yields Mice Whose Brains Are Chimeric for Human Glia," J Neurosci 34, 16153-16161 (2014); and Windrem, M. S. et al., "Human Glial Progenitor Cells Effectively Remyelinate the Demyelinated Adult Brain," Cell Reports 31, 107658 (2020)). However, to effect therapeutic replacement, allogeneic hGPCs must compete against the endogenous pool, displace them, and eventually repopulate the afflicted areas of the host's brain. In prior studies of mouse-to-mouse allografts, the competitive interactions between healthy and diseased glial progenitor cells (GPCs) favor the expansion and integration of the healthy donor population (Givogri, M. I. et al., "Oligodendroglial Progenitor Cell Therapy Limits Central Neurological Deficits in Mice with Metachromatic Leukodystrophy," J Neurosci 26, 3109-3119 (2006), U.S. Pat. No. 10,279,051 to Goldman, and U.S. Pat. No. 10,779, 519 to Goldman). Nonetheless, it remains unclear whether healthy human GPCs can outcompete and replace their diseased human counterparts.

The present disclosure is directed to overcoming these and other deficiencies in the art.

SUMMARY

One aspect of the present application relates to a chimeric non-human mammal, wherein (1) at least 30% of all the glial cells in the corpus callosum of the chimeric non-human mammal are human glial cells, and/or (2) at least 5% of all of the glial cells in the white matter of the brain and/or brain stem of the chimeric non-human mammal are human glial cells, and wherein the human glial cells comprise a combination of human disease-specific glial cells and healthy human glial cells, wherein the human disease-specific glial cells are tagged with a first detectable label, and wherein the healthy human glial cells are tagged with a second detectable label that is distinguishable from the first detectable label.

Another aspect of the present application relates to a chimeric non-human mammal, wherein (1) at least 30% of all the glial cells in the corpus callosum of the chimeric non-human mammal are human glial cells, and/or (2) at least 5% of all of the glial cells in the white matter of the brain and/or brain stem of the chimeric non-human mammal are human glial cells, and wherein the human glial cells comprise a first group of healthy human glial cells tagged with a first detectable label and a second group of healthy human glial cells tagged with a second detectable label that is distinguishable from the first detectable label.

Another aspect of the present application relates to a method for producing a chimeric non-human mammal comprising human glial cells, the method comprises the steps of: introducing a first population of human glial progenitor cells into the brain and/or brain stem of a non-human mammal, wherein the first population of human glial progenitor cells are tagged with a first detectable label; introducing a second population of human glial progenitor cells into the brain and/or brain stem of a non-human mammal, wherein the second population of human glial progenitor cells are tagged with a second detectable label that is distinguishable from the first detectable label; recovering, as a result of said introducing, a chimeric non-human mammal with human glial cells at least partially replacing native glial cells in the brain or brain stem, wherein (1) at least 30% of all the glial cells in the corpus callosum of the chimeric non-human mammal are human glial cells, and/or (2) at least 5% of all of the glial cells in the white matter of the brain and/or brain stem of the chimeric non-human mammal are human glial cells.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 9, Panels A-D show co-engrafted isogenic clones of wildtype glia thrive and admix while displacing HD glia. Panel A shows immunolabeling against human nuclear antigen (hN) shows that both WT-mCherry (mCherry+hN+, red, white) and WT-untagged (mCherry-EGFP-hN+, white) glia expanded within the previously humanized striatum, progressively displacing HD glia (EGFP+hN+, green, white). Scale bar 500 µm. Panel B shows vast homotypic domains were formed as mixed WT glia expanded and displaced resident HD glia. Scale bar 100 µm. Panel C shows isogenic WT-mCherry and WT-untagged were found admixing. Scale bar 100 µm. Panel D shows that within WT glia dominated domains, only more complex astrocyte-like HD glia could be found, typically within white matter tracts. Scale bar: 10 µm.

Figure 11:
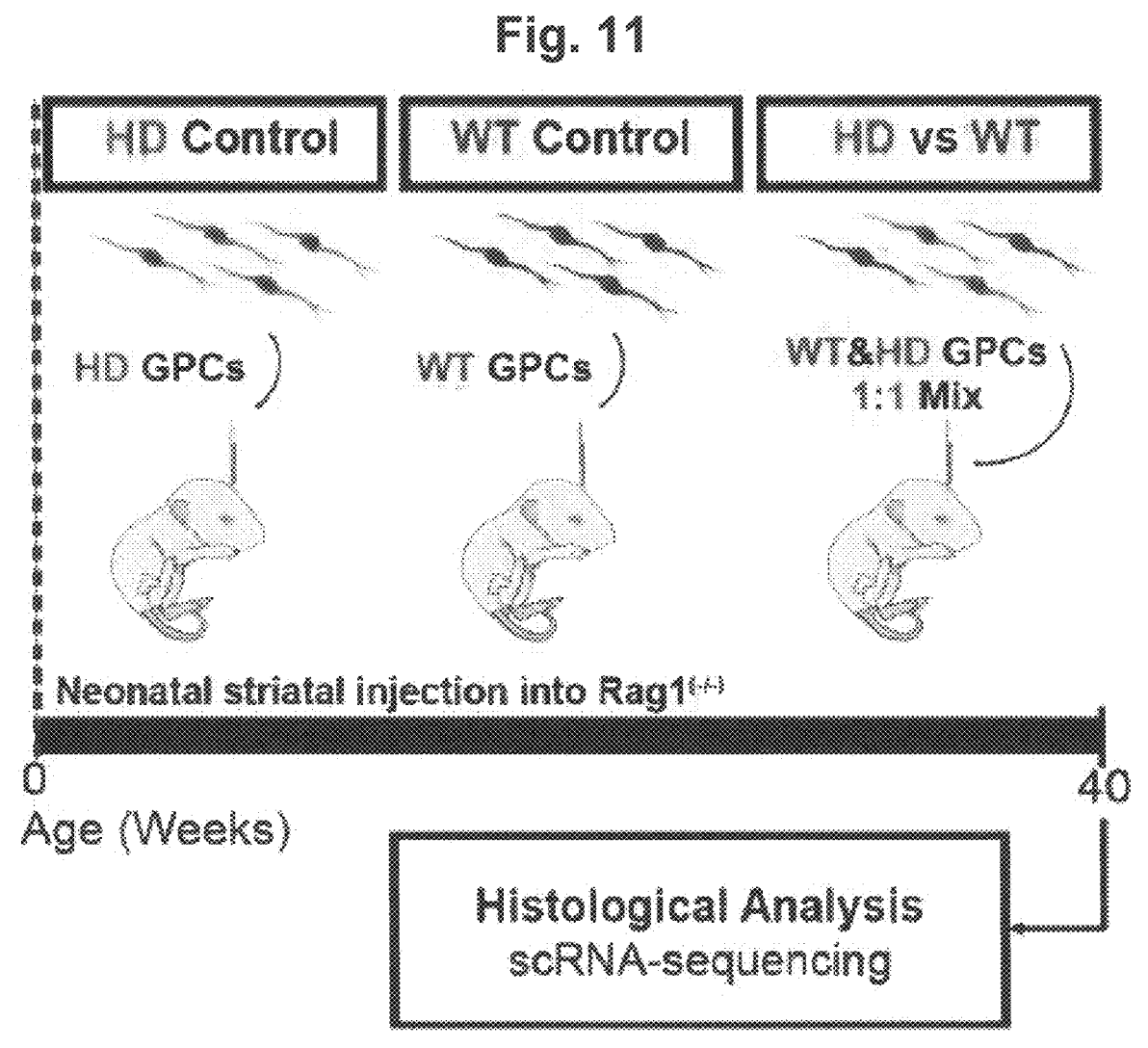

FIG. 11 illustrates the experimental design for co-engrafting WT and HT glia in neonatal mice.

Figure 13:
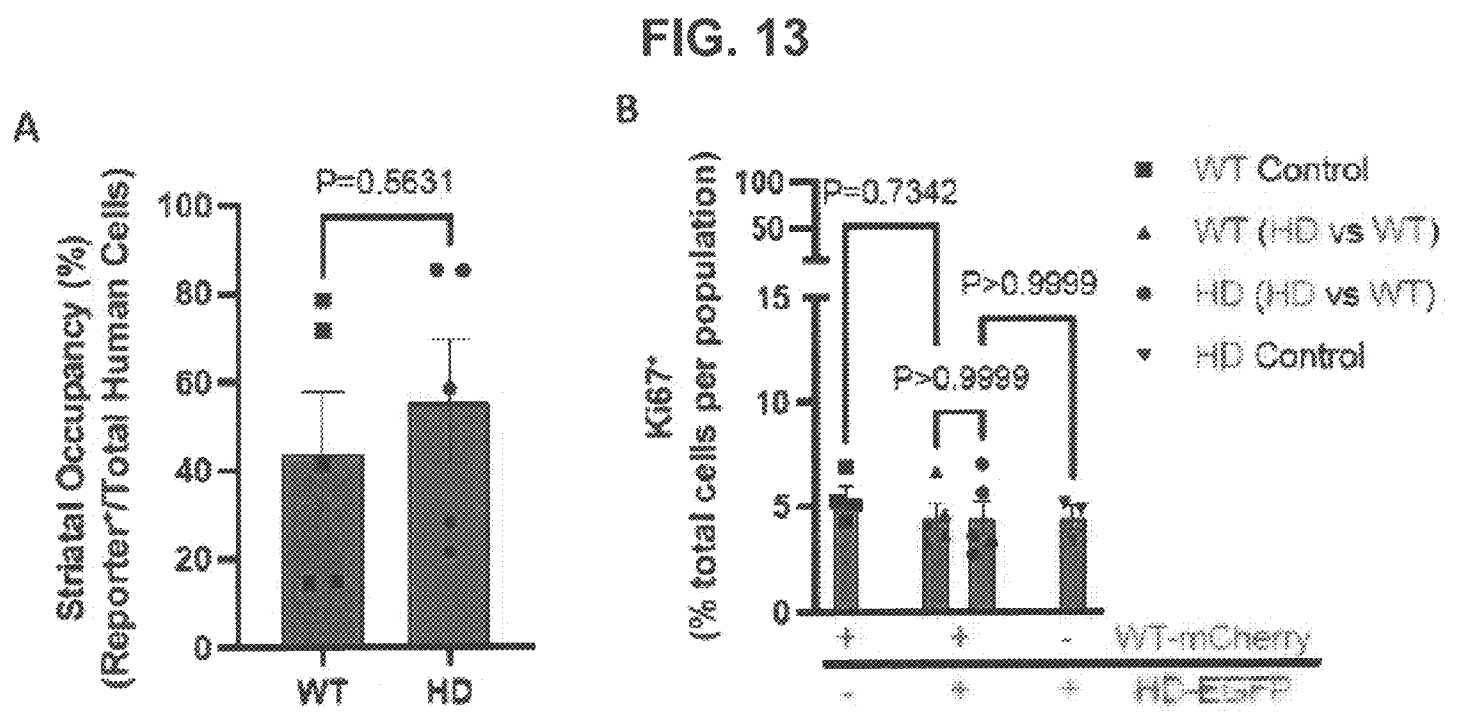

FIG. 13, Panels A-B demonstrates equal growth of neonatally engrafted WT and HD glia is sustained by equally proliferative Ki67+ (white) glial pools; HD Control—n=3; WT Control—n=4; HD vs WT—n=5; One-way ANOVA with Tukey's multiple comparisons test.

Figure 14:
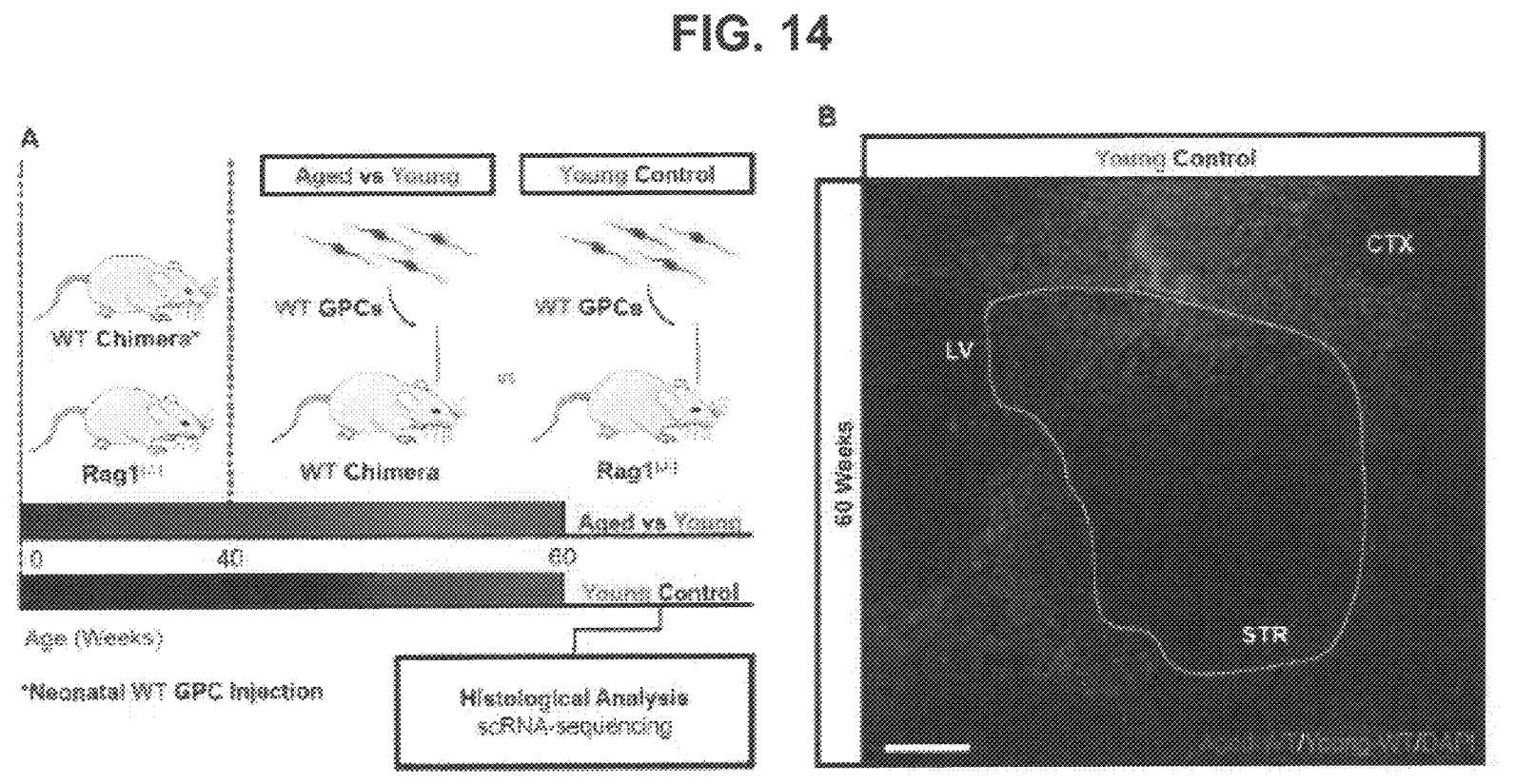

FIG. 14, Panels A-B demonstrate differences in cellular age are sufficient to drive human glial repopulation.

DETAILED DESCRIPTION

Figure 1:
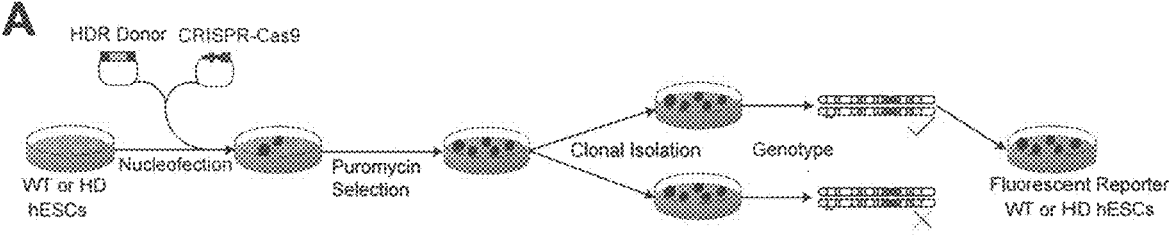
FIG. 1, Panels A-B show representative images of expression of WT-mCherry and HD-EGFP. Panel A shows workflow employed in the genetic engineering of the adeno-associated virus integration site 1 (AAVS1) locus of hESC lines to constitutively express transgenes of interest. Panel A' shows the mechanism of CRISPR-Cas9 mediated transgene integration into the AAVS1 locus (located in the first intron of the protein phosphatase 1 regulatory subunit 12C (PPP1R12C) gene). Panels B-B' show representative images of expression of WT-mCherry and HD-EGFP. Panels C-D illustrate transgene constructs driving expression of either mCherry or EGFP (enhanced green fluorescent protein) inserted into the AAVS1 safe-harbor locus of WT GENEA019 (mcherry) and HD GENEA020 (EGFP) hESCs. Panel E shows representative images of WT-mCherry (Panel B) and HD-EGFP expression in the brain (Panel B').
Figure 1:
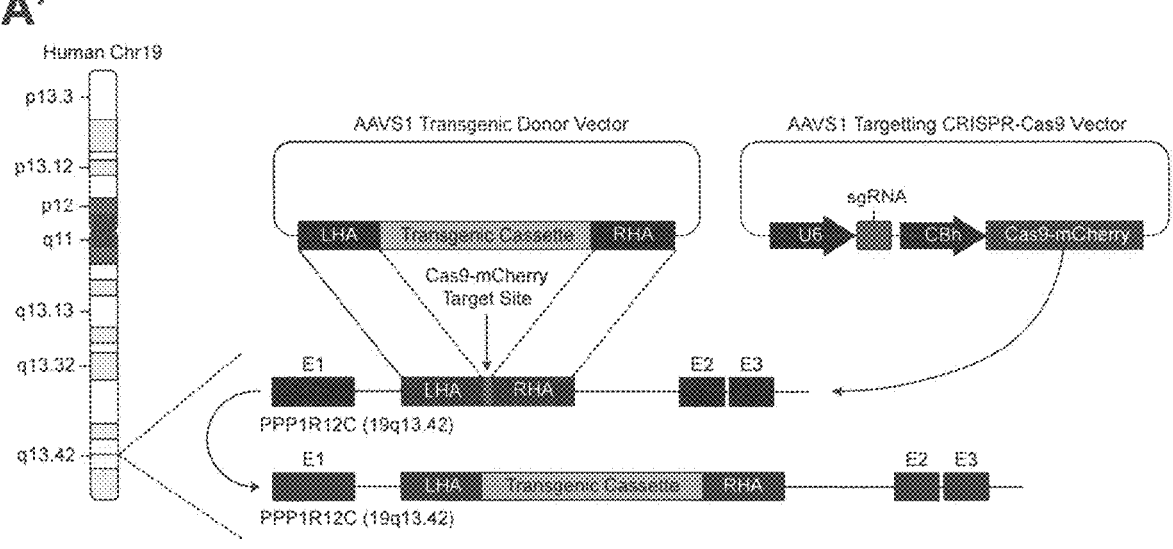
Figure 1:
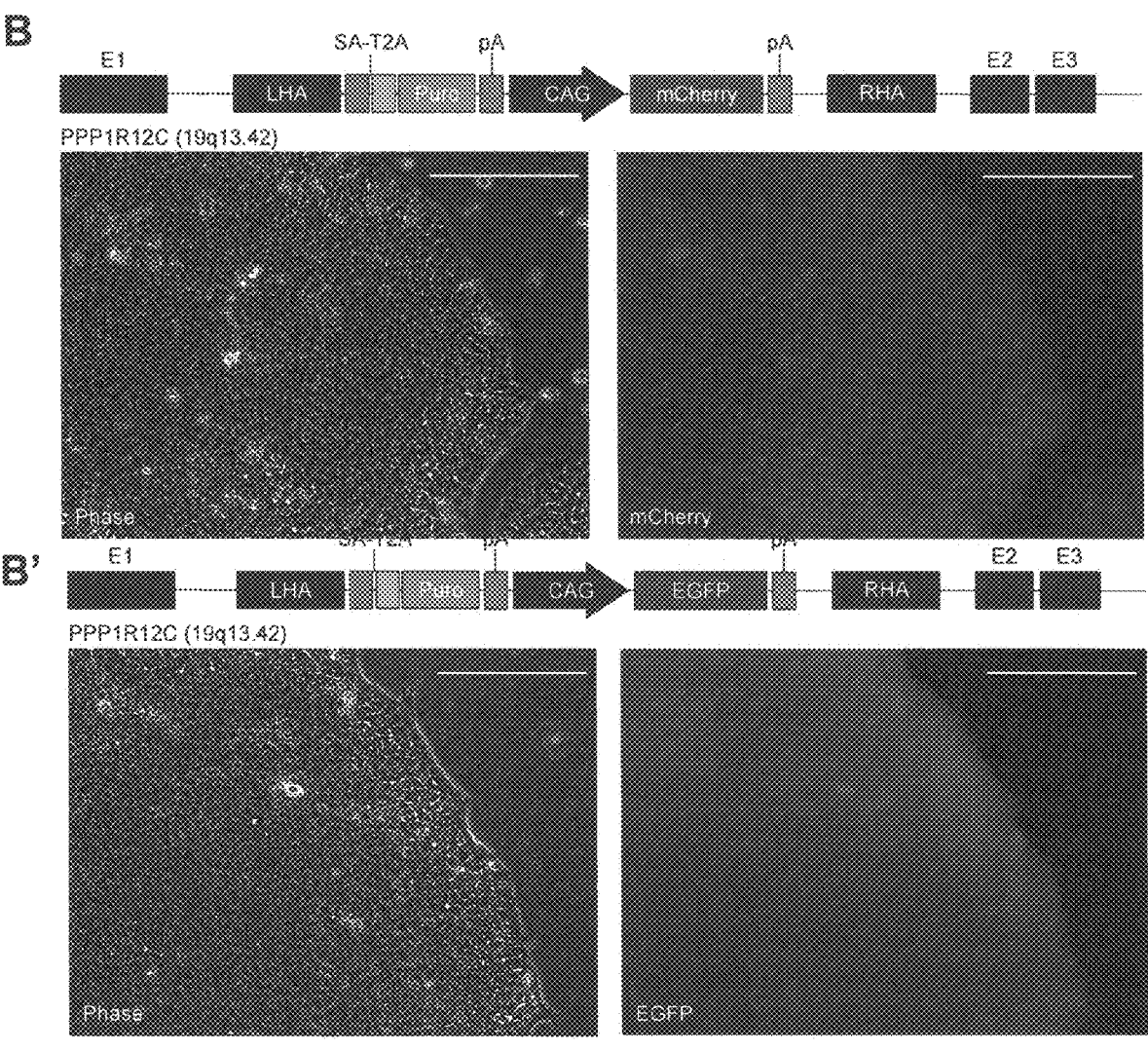
Figure 1:
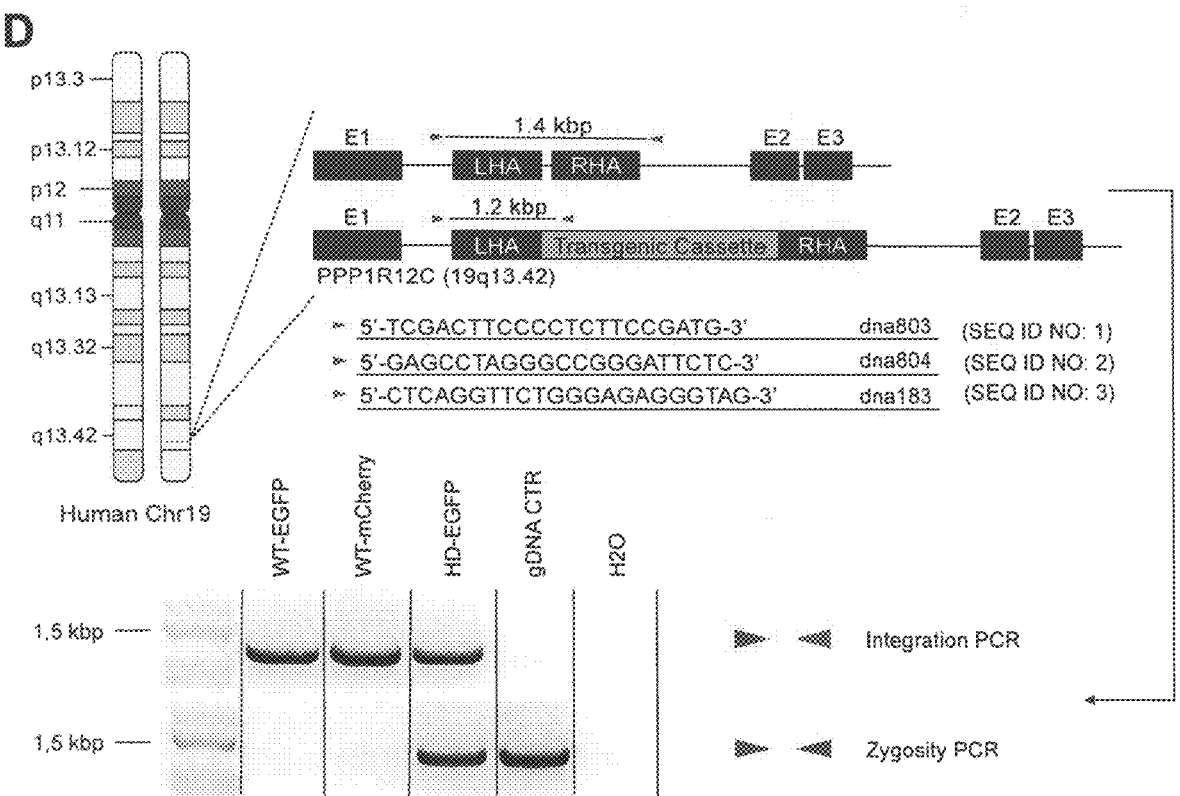

Reference will be made in detail to certain aspects and exemplary embodiments of the application, illustrating examples in the accompanying structures and figures. The aspects of the application will be described in conjunction with the exemplary embodiments, including methods, materials and examples, such description is non-limiting, and the scope of the application is intended to encompass all equivalents, alternatives, and modifications, either generally known, or incorporated here. The described aspects, features, advantages, and characteristics of the invention may be combined in any suitable manner in one or more further embodiments. One skilled in the relevant art will recognize that the invention may be practiced without one or more of the specific aspects or advantages of a particular embodiment. In other instances, additional aspects, features, and advantages may be recognized and claimed in certain embodiments that may not be present in all embodiments of the invention. Further, one skilled in the art will recognize many techniques and materials similar or equivalent to those described here, which could be used in the practice of the aspects and embodiments of the present application. The described aspects and embodiments of the application are not limited to the methods and materials described.

Unless otherwise defined, all technical and scientific terms used herein have the same meaning as commonly understood by one of ordinary skill in the art to which this application belongs.

Ranges may be expressed herein as from "about" one particular value and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to "the value," greater than or equal to the value" and possible ranges between values are also disclosed, as appropriately understood by the skilled artisan. For example, if the value "10" is disclosed the "less than or equal to 10" as well as "greater than or equal to 10" is also disclosed.

As used in this specification and the appended claims, the singular forms "a," "an" and "the" include plural referents unless the content clearly dictates otherwise. Thus, for example, reference to "a peptide" includes "one or more" peptides or a "plurality" of such peptides.

The present application leverages the human glial-chimeric mouse model (Goldman, S. A., et al., "Modeling Cognition and Disease Using Human Glial Chimeric Mice," Glia 63:1483-1493 (2015), which is hereby incorporated by reference in its entirety) in which a substantial degree of glial humanization can be achieved following perinatal delivery of human glial progenitor cells (GPCs)—to model competition between healthy and diseased human glia in vivo. To that end, healthy hGPCs were engrafted into the striata of adult glial chimeras that are already chimerized neonatally with hGPCs produced from human embryonic stem cells (ESCs) derived from subjects with Huntington disease (HD). HD is a prototypic monogenic neurodegenerative disease, resulting from the expression of a mutant CAG-repeat expanded HTT gene (Waldvogel, H. J., et al., "Behavioral Neurobiology of Huntington's Disease and Parkinson's Disease," Curr Top Behav Neurosci 22:33-80 (2014), Bates, G. P. et al. "Huntington Disease," Nat Rev Dis Primers 1: 15005 (2015), and Tabrizi, S. J., et. al., "Huntington Disease: New Insights into Molecular Pathogenesis and Therapeutic Opportunities," Nat Rev Neurol 16: 529-546 (2020), which are hereby incorporated by reference in their entirety). It was previously established that glial pathology is causally involved in the synaptic dysfunction of HD, and that replacement of mouse huntingtin gene (mHTT)-expressing murine glia by normal wild-type human glia in transgenic mouse models of HD was sufficient to rescue aspects of HD phenotype. However, it was unknown if human wild-type human glia can replace mHTT-expressing human hGPCs in vivo.

The ability to replace mHTT-expressing hGPCs in vivo was previously unknown. Applicants have established that when healthy hGPCs were delivered into the striata of adult mice that had been chimerized neonatally with mHTT-expressing hGPCs, that the healthy hGPCs pervaded the humanized host striata, outcompeting and displacing the already resident mHTT-expressing parenchymal human glial progenitors. The dominance of the healthy cells was sustained by a sustained proliferative advantage, and progressed with the active elimination of the resident HD glia from the tissue. Yet while the expression of mHTT imparted a competitive disadvantage to HD glia, disease-state alone was insufficient to explain all results, since the perinatal co-engraftment of wildtype (WT) and HD hGPCs together revealed that both populations expanded and survived when co-injected. Rather, the competitive repopulation of the HD striatum by healthy glia was driven not by the disease state but by the difference in age—and thus proliferative capacity—between the newly implanted healthy GPCs and the resident HD glia. These observations highlight the potential of human GPC as therapeutic vectors for the variety of neurological disorders that can benefit from glial replacement.

I. Definitions

As used herein, the following terms or phrases (in parentheses) shall have the following meanings:

As used herein, the term "mammal" refers to a group of vertebrate animals constituting the class Mammalia, characterized by the presence of mammary glands which in females produce milk for feeding (nursing) their young, a neocortex (a region of the brain), fur or hair, and three middle ear bones. Humans are mammals. The term "non-human mammals" encompasses all mammals except humans.

As used herein, the term "chimeric" refers to an organism containing a mixture of genetically different tissues, formed by processes such as fusion of early embryos, grafting, or mutation.

As used herein, the term "corpus callosum" refers to a bundle of nerve fibers in the longitudinal fissure of the brain that enables corresponding regions of the left and right cerebral hemispheres to communicate. The axons and dendrites of the neurons in the corpus callosum synapse with cortical neurons on symmetrically related points of the hemispheres. Thus, electrical stimulation of a point on one hemisphere usually gives rise to a response on a symmetrically related point on the other, by virtue of these callosal connections. The neurons in the corpus callosum also are insulated by a myelin sheath, which facilitates the rapid conduction of electrical impulses between the hemispheres.

As used herein, the term "brain stem" refers to the posterior stalk-like part of the brain that connects the cerebrum with the spinal cord. In the human brain the brainstem is composed of the midbrain, the pons, and the medulla oblongata. The midbrain is continuous with the thalamus of the diencephalon through the tentorial notch, and sometimes the diencephalon is included in the brainstem.

As used herein, the term "glial cells" refers to a population of non-neuronal cells that provide support and nutrition, maintain homeostasis, either form myelin or promote myelination, and participate in signal transmission in the nervous system. "Glial cells" as used herein encompasses fully differentiated cells of the glial lineage, such as oligodendrocytes or astrocytes, as well as glial progenitor cells, each of which can be referred to as macroglial cells. The term "HD glia," as used herein, refers to glia expressing mHTT. The term "WT glia," as used herein, refers to glia not expressing mHTT.

As used herein the term "human disease-specific glial cells" refers to glial cells that manifest the conditions of certain human diseases that are associated with the degradation of the function or other behavior of glial cells in a manner that negatively impacts the health of an individual carrying such cells. Such diseases may include, but are not limited to, Huntington's disease, frontotemporal dementia, Parkinson's disease, multisystem atrophy, and amyotrophic lateral sclerosis.

As used herein the term "healthy human glial progenitor cells" refers to cells which function effectively to expand, differentiate, and if need be engraft, into functional oligodendrocytes and astrocytes. Such cells can outcompete the host glial pool to ultimately colonize and dominate recipient brains.

As used herein the term "human neurodegenerative disorder-specific glial cells," refers to glial cells which manifest the conditions of certain human neurodegenerative disorders that are associated with the degradation of the function or other behavior of glial cells in a manner that negatively impacts the health of an individual carrying such cells. Such neurodegenerative disorders may include Huntington's disease, frontotemporal dementia, Parkinson's disease, multisystem atrophy, and amyotrophic lateral sclerosis.

As used herein, the term "Huntington's disease (HD)" refers to an autosomal dominant neurodegenerative disease characterized by a relentlessly progressive movement disorder with devastating psychiatric and cognitive deterioration. Huntington's disease is associated with a consistent and severe atrophy of the neostriatum which is related to a marked loss of the GABAergic medium-sized spiny projection neurons, the major output neurons of the striatum. Huntington's disease is characterized by abnormally long CAG repeat expansions in the first exon of the Huntingtin gene ("HTT"). The encoded polyglutamine expansions of mutant huntingtin protein disrupt its normal functions and protein-protein interactions, ultimately yielding widespread neuropathology, most rapidly evident in the neostriatum.

As used herein, the term "Frontotemporal dementia" refers to a group of related conditions resulting from the progressive degeneration of the temporal and frontal lobes of the brain. These areas of the brain play a significant role in decision-making, behavioral control, emotion, and language.

As used herein, the term "Parkinson's disease" refers to a progressive nervous system disorder that affects movement. Parkinson's disease is characterized by progressive neurodegeneration.

As used herein, the term "multisystem atrophy" refers to a progressive neurodegenerative disorder characterized by a combination of symptoms that affect both the autonomic nervous system (the part of the nervous system that controls involuntary action such as blood pressure or digestion) and movement. The symptoms reflect the progressive loss of function and death of different types of nerve cells in the brain and spinal cord.

As used herein, the term "Amyotrophic lateral sclerosis (ALS, commonly called "Lou Gehrig's disease")" refers to the most common motor neuron disease in adults. Motor neuron diseases are neurodegenerative diseases that cause selective loss of the nerve cells that directly connect the brain to muscles.

As used herein the term "human neuropsychiatric disorder-specific glial cells" refers to glial cells which manifest the conditions of certain human neuropsychiatric disorders that are associated with the degradation of the function or other behavior of glial cells in a manner that negatively impacts the health of an individual carrying such cells. Such neuropsychiatric disorders may include schizophrenia, bipolar disorder and autism spectrum disorder.

As used herein, the term "schizophrenia" refers to a serious mental illness that affects how a person thinks, feels, and behaves. The symptoms of schizophrenia generally fall into the following three categories: 1) psychotic symptoms including altered perceptions, 2) negative symptoms including loss of motivation, disinterest and lack of enjoyment, and 3) cognitive symptoms including problems in attention, concentration, and memory.

As used herein, the term "autism spectrum disorder" refers to a neurodevelopment disorder that causes a wide range of impairments in social communication and restricted and repetitive behaviors.

As used herein, the term "bipolar disorder" refers to a serious mental illness characterized by extreme mood swings. They can include extreme excitement episodes or extreme depressive feelings. Three types of bipolar disorder include: 1) Bipolar I Disorder, defined by manic episodes, 2) Bipolar II Disorder, that is defined by depressive episodes, and 3) Cyclothymic Disorder, defined by periods of hypomanic and depressive symptoms.

As used herein the term "human myelin disease-specific glial cells" refers to glial cells which manifest the conditions of certain human myelin diseases that are associated with the degradation of the function or other behavior of glial cells in a manner that negatively impacts the health of an individual carrying such cells. Such human myelin diseases may include leukodystrophy or a white matter disease.

As used herein the term "leukodystrophy" refers to a group of rare, primarily inherited neurological disorders known as the leukodystrophies that result from the abnormal production, processing, or development of myelin and other components of central nervous system (CNS) white matter, such as cells called oligodendrocytes and astrocytes. All leukodystrophies are the result of genetic defects (mutations).

As used herein, the term "white matter" relates to a component of the central nervous system, in the brain and superficial spinal cord, which consists mostly of glial cells and myelinated axons that transmit signals from one region of the cerebrum to another and between the cerebrum and lower brain centers.

As used herein, the term "detectable label" refers to any means of labelling a target that shall allow it to be distinguished or differentiated from its context by its labelling, whether it is labelled visually or by other means. Examples of detectable label include, but are not limited to, green fluorescence proteins (GFPs) and red fluorescence protein (RFPs).

As used herein, the term "pre-natal" refers to before, during or relating to pregnancy.

As used herein, the term "neo-natal" refers to the period relating to or affecting an infant one month after birth.

As used herein, the term "post-natal" refers to developmental stages after birth, including adult.

As used hereinafter, the term "youth-related genes" refers to genes with significantly increased expression in young glial cells compared to older glial cells.

In some embodiments, the term "young glial cells" refers to stem cells that are induced to start differentiation into glial progenitor cell in an in vitro setting at differentiation stage 6 based on the protocol of Wang et al. Cell Stem Cell 12, 252-264, 2013, or at the equivalent differentiation stage based on other protocols. Compared with old glial cells, young glial cells may have one or more of the following characteristics: (i) growing or proliferating or dividing faster and (ii) longer telomeres or higher telomerase activity. In some embodiments, the term "young glial cells" refers to glial progenitor cells or their progeny that are within 1-20 weeks of transplantation into a host. The term "older glial cells" or "old glial cells" is used in relative to the term "young glial cells". In some embodiments, the young glial cells are glial cells that have been cultured for 1-5, 5-10, 5-20, 5-30, 10-20, 10-30, or 20-30 weeks at differentiation stage 6 based on the protocol of Wang et al. Cell Stem Cell 12, 252-264, 2013, or at the equivalent differentiation stage based on other protocols.

In some embodiments, older glial cells are glial cells that are derived from glial progenitor cells that have been transplanted into a host for 5-10, 5-20, 5-30, 5-40, 5-50, 5-60, 5-70, 5-80, 5-90, 5-100, 10-20, 10-30, 10-40, 10-50, 10-60, 10-70, 10-80, 10-90, 10-100, 20-30, 20-40, 20-50, 20-60, 20-70, 20-80, 20-90, 20-100, 30-40, 30-50, 30-60, 30-70, 30-80, 30-90, 30-100, 40-50, 40-60, 40-70, 40-80, 40-90, 40-100, 50-60, 50-70, 50-80, 50-90, 50-100, 60-70, 60-80, 60-90,60-100, 70-80, 70-90, 70-100, 80-90, 80-100, or 90-100 weeks. In some embodiments, the older glial cells are glial cells that have been cultured for 5-100, 5-10, 5-20, 5-30, 5-40, 5-50, 5-60, 5-70, 5-80, 5-90, 10-20, 10-30, 10-40, 10-50, 10-60, 10-70, 10-80, 10-90, 10-100, 20-30, 20-40, 20-50, 20-60, 20-70, 20-80, 20-90, 20-100, 30-40, 30-50, 30-60, 30-70, 30-80, 30-90, 30-100, 40-50, 40-60, 40-70, 40-80, 40-90, 40-100, 50-60, 50-70, 50-80, 50-90, 50-100, 60-70, 60-80, 60-90,60-100, 70-80, 70-90, 70-100, 80-90, 80-100, or 90-100 weeks at differentiation stage 6 based on the protocol of Wang et al. Cell Stem Cell 12, 252-264, 2013, or at the equivalent differentiation stage based on other protocols.

II. Chimeric Non-Human Mammal Model

One aspect of the present application relates to a chimeric non-human mammal, wherein (1) at least 30% of all the glial cells in the corpus callosum of the chimeric non-human mammal are human glial cells, and/or (2) at least 5% of all of the glial cells in the white matter of the brain and/or brain stem of the chimeric non-human mammal are human glial cells, and wherein the human glial cells comprise a combination of human disease-specific glial cells and healthy human glial cells, wherein the human disease-specific glial cells are tagged with a first detectable label, and wherein the healthy human glial cells are tagged with a second detectable label that is distinguishable from the first detectable label.

In some embodiments, the human disease-specific glial cells comprise human neurodegenerative disorder-specific glial cells, or human neuropsychiatric disorder-specific glial cells, or human myelin disease-specific glial cells.

In some embodiments, the human disease-specific glial cells comprise human neurodegenerative disorder-specific glial cells and wherein the human neurodegenerative disorder is selected from the group consisting of Huntington's disease, frontotemporal dementia, Parkinson's disease, multisystem atrophy, and amyotrophic lateral sclerosis.

In some embodiments, the human disease-specific glial cells comprise Huntington's disease-specific glial cells.

In some embodiments, the human disease-specific glial cells comprise human neuropsychiatric disorder-specific glial cells and wherein the human neuropsychiatric disorder is selected from the group consisting of schizophrenia, autism spectrum disorder, and bipolar disorder.

In some embodiments, the human disease-specific glial cells comprise human myelin disease-specific glial cells and wherein the human myelin disease leukodystrophy or a white matter disease In some embodiments, the human disease-specific glial cells are derived from human disease-specific glial progenitor cells implanted at a first implantation date, wherein the healthy human glial cells are derived from healthy human glial progenitor cells implanted at a second implantation date, and wherein the first implantation date is the same as the second implantation date.

In some embodiments, the human disease-specific glial cells are derived from human disease-specific glial progenitor cells implanted at a first implantation date, wherein the healthy human glial cells are derived from healthy human glial progenitor cells implanted at a second implantation date, and wherein the first implantation date is earlier than the second implantation date.

In some embodiments, the first implantation date is 5-100, 5-10, 5-15, 5-20, 5-25, 5-30, 5-35, 5-40, 5-45, 5-50, 5-55, 5-60, 5-65, 5-70, 5-75, 5-80, 5-85, 5-90, 5-95, 10-15, 10-20, 10-25, 10-30, 10-35, 10-40, 10-45, 10-50, 10-55, 10-60, 10-65, 10-70, 10-75, 10-80, 10-85, 10-90, 10-95, 10-100, 15-20, 15-25, 15-30, 15-35, 15-40, 15-45, 15-50, 15-55, 15-60, 15-65, 15-70, 15-75, 15-80, 15-85, 15-90, 15-95, 15-100, 20-25, 20-30, 20-35, 20-40, 20-45, 20-50, 20-55, 20-60, 20-65, 20-70, 20-75, 20-80, 20-85, 20-90, 20-95, 20-100, 25-30, 25-35, 25-40, 25-45, 25-50, 25-55, 25-60, 25-65, 25-70, 25-75, 25-80, 25-85, 25-90, 25-95, 25-100, 30-35, 30-40, 30-45, 30-50, 30-55, 30-60, 30-65, 30-70, 30-75, 30-80, 30-85, 30-90, 30-95, 30-100, 35-40, 35-45, 35-50, 35-55, 35-60, 35-65, 35-70, 35-75, 35-80, 35-85, 35-90, 35-95, 35-100, 40-45, 40-50, 40-55, 40-60, 40-65, 40-70, 40-75, 40-80, 40-85, 40-90, 40-95, 40-100, 45-50, 45-55, 45-60, 45-65, 45-70, 45-75, 45-80, 45-85, 45-90, 45-95, 45-100, 50-55, 50-60, 50-65, 50-70, 50-75, 50-80, 50-85, 50-90, 50-95, 50-100, 55-60, 55-65, 55-70, 55-75, 55-80, 55-85, 55-90, 55-95, 55-100, 60-65, 60-70, 60-75, 60-80, 60-85, 60-90, 60-95, 60-100, 65-70, 65-75, 65-80, 65-85, 65-90, 65-95, 65-100, 70-75, 70-80, 70-85, 70-90, 70-95, 70-100, 75-80, 75-85, 75-90, 75-95, 75-100, 80-85, 80-90, 80-95, 80-100, 85-90, 85-95, 85-100, 90-95, 90-100 or 95-100 weeks before the second implantation date.

In some embodiments, the first implantation date is 30-40 weeks before the second implantation date.

In some embodiments, the human neurodegenerative disorder specific glial cells of the non-human mammal described herein exhibit glial cell pathology, e.g., glial cell specific gene expression, growth, structure, organization, differentiation, proliferation, and the like that is associated with the neurodegenerative disorder. Similarly, the non-human mammal model of the human neurodegenerative disease as described herein exhibits at least some of the pathological, physiological, and behavioral characteristics and phenotypes associated with the human neurodegenerative disorder. For example, in one embodiment, the non-human mammal model is a model of Huntington's disease. In this embodiment, the mammal model exhibits significantly slower motor learning and decrements in motor coordination, which is characteristic of Huntington's disease, as compared to non-human healthy mammals (i.e., non-human mammals comprising non-diseased human glial cells). Likewise, striatal neurons of the non-human mammal model of Huntington's disease exhibit increased neuronal excitability and decreased input resistance compared to striatal neurons of a non-human healthy mammal. This neuronal phenotype is characteristic of the neuronal phenotype in a human patient having Huntington's disease.

In some embodiments, the human neurodegenerative disorder specific glial cells of the non-human mammal model are derived from a human patient having the disorder. In another embodiment, the human neurodegenerative disorder specific glial cells of the non-human mammal model are engineered to be neurodegenerative disorder specific, i.e., the cells are engineered to contain one or more genetic mutations associated with the neurodegenerative disease and/or increase or decrease expression of one or more disease associated biological molecules (e.g., proteins, polysaccharides, lipids, or nucleic acid molecules). For example, as described herein, an exemplary non-human mammal model of Huntington's disease may comprise human glial cells engineered to express a mutant Huntingtin gene having an expansion of a CAG (cytosine-adenine-guanine) triplet repeat.

The human neurodegenerative disorder specific glial cells of the non-human mammal model described herein may be derived from any suitable source of glial cells, such as, for example and without limitation, human induced pluripotent stem cells (iPSCs), embryonic stem cells, fetal tissue, glial progenitor cells, and/or astrocytes as described in more detail below.

In some embodiments, at least 10%, 15%, 20%, 25%, 30%, 35%, 40%, 45% or 50% of all of the glial cells in the white matter of the chimeric non-human mammal's brain and/or brain stem are human glial cells. In some embodiments, the white matter is cerebellar white matter and at least 50% of all of the glial cells in the cerebellar white matter of the mammal's brain are human glial cells.

In some embodiments, at least 50%, 55%, 60%, 65%, 70%, 75%, 80% or 85% of all of the glial cells in the corpus callosum of the chimeric non-human mammal's brain are human glial cells.

In some embodiments, at least 70% of all of the glial cells in the corpus callosum of the chimeric non-human mammal's brain are human glial cells.

In some embodiments, at least 30%, 35%, 40%, 45%, 50%, 55%, 60%, 65%, 70%, 75%, 80%, 85%, or 90% of the glial cells in the corpus callosum of the chimeric non-human mammal are human neurodegenerative disorder specific glial cells.

In another embodiment, at least 50% of all of the glial cells in the corpus callosum of the chimeric non-human mammal are human neurodegenerative disorder specific glial cells.

In another embodiment, at least 70% of all of the glial cells in the corpus callosum of the chimeric non-human mammal are human neurodegenerative disorder specific glial cells.

In yet another embodiment, at least 90% of all the glial cells in the corpus callosum of the non-human mammal are human neurodegenerative disorder specific glial cells.

In some embodiments, the chimeric non-human mammal's brain or brain stem comprises human neurodegenerative disorder glial cells, where the human neurodegenerative disorder is selected from the group consisting of Huntington's disease, Alzheimer's disease, frontotemporal dementia, Parkinson's disease, multisystem atrophy, and amyotrophic lateral sclerosis. The non-human mammal model described herein is a model of a human neurodegenerative disorder. A neurodegenerative disorder or a neurodegenerative disease is a chronic progressive neuropathy characterized by selective and generally symmetrical loss of neurons in motor, sensory, or cognitive systems.

In some embodiments, the chimeric non-human mammal's brain or brain stem comprises human neuropsychiatric disorder glial cells, where the human neuropsychiatric disorder is selected from the group consisting of schizophrenia, autism spectrum disorder, and bipolar disorder.

In some embodiments, the chimeric non-human mammal's brain or brain stem has a human myelin disease, where the human myelin disease is a leukodystrophy or a white matter disease. In one embodiment, the chimeric non-human mammal is hypomyelinated. Hypomyelinated mammals comprise an abnormally reduced amount of myelin. In another embodiment, the chimeric non-human mammal has normal levels of myelin throughout its brain and brainstem.

Another aspect of the present application relates to a chimeric non-human mammal, wherein (1) at least 30% of all the glial cells in the corpus callosum of the chimeric non-human mammal are human glial cells, and/or (2) at least 5% of all of the glial cells in the white matter of the brain and/or brain stem of the chimeric non-human mammal are human glial cells, and wherein the human glial cells comprise a first group of healthy human glial cells tagged with a first detectable label and a second group of healthy human glial cells tagged with a second detectable label that is distinguishable from the first detectable label.

In some embodiments, the first group of healthy human glial cells are derived from a first group of healthy human glial progenitor cells implanted at a first implantation date, wherein the second group of healthy human glial cells are derived from a second group of healthy human glial progenitor cells implanted at a second implantation date, and wherein the first implantation date is the same as the second implantation date.

In some embodiments, the first group of healthy human glial cells are derived from a first group of healthy human glial progenitor cells implanted at a first implantation date, wherein the second group of healthy human glial cells are derived from a second group of healthy human glial progenitor cells implanted at a second implantation date, and wherein the first implantation date is earlier than the second implantation date.

In some embodiments, the first implantation date is 5-100, 5-10, 5-15, 5-20, 5-25, 5-30, 5-35, 5-40, 5-45, 5-50, 5-55, 5-60, 5-65, 5-70, 5-75, 5-80, 5-85, 5-90, 5-95, 10-15, 10-20, 10-25, 10-30, 10-35, 10-40, 10-45, 10-50, 10-55, 10-60, 10-65, 10-70, 10-75, 10-80, 10-85, 10-90, 10-95, 10-100, 15-20, 15-25, 15-30, 15-35, 15-40, 15-45, 15-50, 15-55, 15-60, 15-65, 15-70, 15-75, 15-80, 15-85, 15-90, 15-95, 15-100, 20-25, 20-30, 20-35, 20-40, 20-45, 20-50, 20-55, 20-60, 20-65, 20-70, 20-75, 20-80, 20-85, 20-90, 20-95, 20-100, 25-30, 25-35, 25-40, 25-45, 25-50, 25-55, 25-60, 25-65, 25-70, 25-75, 25-80, 25-85, 25-90, 25-95, 25-100, 30-35, 30-40, 30-45, 30-50, 30-55, 30-60, 30-65, 30-70, 30-75, 30-80, 30-85, 30-90, 30-95, 30-100, 35-40, 35-45, 35-50, 35-55, 35-60, 35-65, 35-70, 35-75, 35-80, 35-85, 35-90, 35-95, 35-100, 40-45, 40-50, 40-55, 40-60, 40-65, 40-70, 40-75, 40-80, 40-85, 40-90, 40-95, 40-100, 45-50, 45-55, 45-60, 45-65, 45-70, 45-75, 45-80, 45-85, 45-90, 45-95, 45-100, 50-55, 50-60, 50-65, 50-70, 50-75, 50-80, 50-85, 50-90, 50-95, 50-100, 55-60, 55-65, 55-70, 55-75, 55-80, 55-85, 55-90, 55-95, 55-100, 60-65, 60-70, 60-75, 60-80, 60-85, 60-90, 60-95, 60-100, 65-70, 65-75, 65-80, 65-85, 65-90, 65-95, 65-100, 70-75, 70-80, 70-85, 70-90, 70-95, 70-100, 75-80, 75-85, 75-90, 75-95, 75-100, 80-85, 80-90, 80-95, 80-100, 85-90, 85-95, 85-100, 90-95, 90-100 or 95-100 weeks before the second implantation date.

In some embodiments, the first implantation date is 30-40 weeks before the second implantation date.

The chimeric non-human mammal of the present application may be of any age. In some embodiments, the chimeric non-human mammal is post-natal. As used herein, the term "post-natal" refers mammals at any age after birth, including adult mammals. In some embodiments, the chimeric non-human mammal is neo-natal. In some embodiments, the chimeric non-human mammal is an adult.

The chimeric non-human mammal of the present application can be any mammal, including mice, rats, guinea pigs and other small rodents, dogs, cats, sheep, goats, and monkeys. In a preferred embodiment of the present application, the chimeric non-human mammal is a mouse. Suitable strains of mice include, without limitation, CD-1® Nude mice, NU/NU mice, BALB/C Nude mice, BALB/C mice, NIH-III mice, SCID® mice, outbred SCID® mice, SCID Beige mice, C3H mice, C57BL/6 mice, DBA/2 mice, FVB mice, CB17 mice, 129 mice, SJL mice, B6C3F1 mice, BDF1 mice, CDF1 mice, CB6F1 mice, CF-1 mice, Swiss Webster mice, SKH1 mice, PGP mice, and B6SJL mice.

In some embodiments, the chimeric non-human mammal of the present application is immune-incompetent, immune-deficient, or immune-suppressed.

III. Method of Producing a Chimeric Non-Human Mammal

Another aspect of the present application relates to a method for producing a chimeric non-human mammal comprising human glial cells. In some embodiments, the method comprises the steps of: introducing a first population of human glial progenitor cells into the brain and/or brain stem of a non-human mammal, wherein the first population of human glial cells are tagged with a first detectable label; introducing a second population of human glial progenitor cells into the brain and/or brain stem of a non-human mammal, wherein the second population of human glial cells are tagged with a second detectable label that is distinguishable from the first detectable label; and recovering, as a result of said introducing, a chimeric non-human mammal with human glial cells least partially replacing native glial cells in the brain or brain stem, wherein (1) at least 30% of all the glial cells in the corpus callosum of the chimeric non-human mammal are human glial cells, and/or (2) at least 5% of all of the glial cells in the white matter of the brain and/or brain stem of the chimeric non-human mammal are human glial cells.

In some embodiments, the first population of human glial progenitor cells are human disease-specific glial progenitor cells and wherein the second population of human glial progenitor cells are healthy human glial progenitor cells. In some embodiments, the human disease-specific glial progenitor cells comprise human neurodegenerative disorder-specific glial progenitor cells, or human neuropsychiatric disorder-specific glial progenitor cells, or human myelin disease-specific glial progenitor cells. In some embodiments, the human disease-specific glial progenitor cells comprise Huntington's disease-specific glial progenitor cells.

In some embodiments, the first population of human glial progenitor cells are healthy human glial progenitor cells and wherein the second population of human glial progenitor cells are healthy human glial progenitor cells.

In some embodiments, the first population of human glial progenitor cells and the second population of human glial progenitor cells are introduced into the brain and/or brain stem of the non-human mammal at the same time.

In some embodiments, the first population of human glial progenitor cells are introduced into the brain and/or brain stem of the non-human mammal at a first implantation date, wherein the second population of human glial progenitor cells are introduced into the brain and/or brain stem of the non-human mammal at a second implantation date, and wherein the first implantation date is earlier than the second implantation date.

In some embodiments, the first implantation date is 5-100, 5-10, 5-15, 5-20, 5-25, 5-30, 5-35, 5-40, 5-45, 5-50, 5-55, 5-60, 5-65, 5-70, 5-75, 5-80, 5-85, 5-90, 5-95, 10-15, 10-20, 10-25, 10-30, 10-35, 10-40, 10-45, 10-50, 10-55, 10-60, 10-65, 10-70, 10-75, 10-80, 10-85, 10-90, 10-95, 10-100, 15-20, 15-25, 15-30, 15-35, 15-40, 15-45, 15-50, 15-55, 15-60, 15-65, 15-70, 15-75, 15-80, 15-85, 15-90, 15-95, 15-100, 20-25, 20-30, 20-35, 20-40, 20-45, 20-50, 20-55, 20-60, 20-65, 20-70, 20-75, 20-80, 20-85, 20-90, 20-95, 20-100, 25-30, 25-35, 25-40, 25-45, 25-50, 25-55, 25-60, 25-65, 25-70, 25-75, 25-80, 25-85, 25-90, 25-95, 25-100, 30-35, 30-40, 30-45, 30-50, 30-55, 30-60, 30-65, 30-70, 30-75, 30-80, 30-85, 30-90, 30-95, 30-100, 35-40, 35-45, 35-50, 35-55, 35-60, 35-65, 35-70, 35-75, 35-80, 35-85, 35-90, 35-95, 35-100, 40-45, 40-50, 40-55, 40-60, 40-65, 40-70, 40-75, 40-80, 40-85, 40-90, 40-95, 40-100, 45-50, 45-55, 45-60, 45-65, 45-70, 45-75, 45-80, 45-85, 45-90, 45-95, 45-100, 50-55, 50-60, 50-65, 50-70, 50-75, 50-80, 50-85, 50-90, 50-95, 50-100, 55-60, 55-65, 55-70, 55-75, 55-80, 55-85, 55-90, 55-95, 55-100, 60-65, 60-70, 60-75, 60-80, 60-85, 60-90, 60-95, 60-100, 65-70, 65-75, 65-80, 65-85, 65-90, 65-95, 65-100, 70-75, 70-80, 70-85, 70-90, 70-95, 70-100, 75-80, 75-85, 75-90, 75-95, 75-100, 80-85, 80-90, 80-95, 80-100, 85-90, 85-95, 85-100, 90-95, 90-100 or 95-100 weeks before the second implantation date.

In some embodiments, the first implantation date is 30-40 weeks before the second implantation date.

The non-human mammal suitable for carrying out the method of the present application may be of any age. In some embodiments, the non-human mammal is pre-natal. In some embodiments, the non-human mammal is neo-natal. In some embodiments, the non-human mammal is an adult.

Any non-human mammal is suitable for carrying out the methods of the present application, including mice, rats, guinea pigs and other small rodents, dogs, cats, sheep, goats, and monkeys. In a preferred embodiment of the present application, the non-human mammal is a mouse. Suitable strains of mice include, without limitation, CD-1® Nude mice, NU/NU mice, BALB/C Nude mice, BALB/C mice, NIH-III mice, SCID® mice, outbred SCID® mice, SCID Beige mice, C3H mice, C57BL/6 mice, DBA/2 mice, FVB mice, CB17 mice, 129 mice, SJL mice, B6C3F1 mice, BDF1 mice, CDF1 mice, CB6F1 mice, CF-1 mice, Swiss Webster mice, SKH1 mice, PGP mice, and B6SJL mice.

In some embodiments, the non-human mammal suitable for carrying out the methods of the present application is immune-incompetent, immune-deficient, or immune-suppressed.

In accordance with the method of the present application, the population of human glial cells to be transplanted into chimeric non-human mammal are preferably bi-potential glial progenitor cells. In one embodiment, the glial progenitor cells can be biased to producing oligodendrocytes. Alternatively, the glial progenitor cells can be biased to producing astrocytes. In a further embodiment of the present application, the human glial cells to be transplanted into the non-human mammal can be astrocytes.

Glial progenitor cells can be obtained from embryonic, fetal, or adult brain tissue, embryonic stem cells, or induced pluripotential cells. Preferably, the glial progenitor cells are isolated from ventricular and subventricular zones of the brain or from the subcortical white matter.

iPSCs are pluripotent cells that are derived from non-pluripotent cells, such as somatic cells. For example, and without limitation, iPSCs can be derived from tissue, peripheral blood, umbilical cord blood, and bone marrow (see e.g., Cai et al., "Generation of Human Induced Pluripotent Stem Cells from Umbilical Cord Matrix and Amniotic Membrane Mesenchymal Cells," J. Biol. Chem. 285 (15): 112227-11234 (2110); Giorgetti et al., "Generation of Induced Pluripotent Stem Cells from Human Cord Blood Cells with only Two Factors: Oct4 and Sox2," Nat. Protocol. 5 (4): 811-820 (2010); Streckfuss-Bomeke et al., "Comparative Study of Human-Induced Pluripotent Stem Cells Derived from Bone Marrow Cells, Hair Keratinocytes, and Skin Fibroblasts," Eur. Heart J. (2012); Hu et al., "Efficient Generation of Transgene-Free Induced Pluripotent Stem Cells from Normal and Neoplastic Bone Marrow and Cord Blood Mononuclear Cells," Blood (2011); Sommer et al., "Generation of Human Induced Pluripotent Stem Cells from Peripheral Blood using the STEMCCA Lentiviral Vector," J. Vis. Exp. 68: e4327 (2012), which are hereby incorporated by reference in their entirety). The somatic cells are reprogrammed to an embryonic stem cell-like state using genetic manipulation. Exemplary somatic cells suitable for the formation of iPSCs include fibroblasts (see e.g., Streckfuss-Bomeke et al., "Comparative Study of Human-Induced Pluripotent Stem Cells Derived from Bone Marrow Cells, Hair Keratinocytes, and Skin Fibroblasts," Eur. Heart J. (2012), which is hereby incorporated by reference in its entirety), such as dermal fibroblasts obtained by a skin sample or biopsy, synoviocytes from synovial tissue, keratinocytes, mature B cells, mature T cells, pancreatic β cells, melanocytes, hepatocytes, foreskin cells, cheek cells, or lung fibroblasts.

Methods of producing induced pluripotent stem cells are known in the art and typically involve expressing a combination of reprogramming factors in a somatic cell. Suitable reprogramming factors that promote and induce iPSC generation include one or more of octamer-binding transcription factor 4 (Oct4), kruppel-like factor 4 (Klf4), SRY (sex determining region Y)-box 2 (Sox2), c-Myc, Nanog, CCAAT-enhancer-binding protein alpha (C/EBPα), estrogen-related receptor beta (Esrrb), Lin28, and nuclear receptor subfamily 5, group A, member 2 (Nr5a2). In certain embodiments, at least two reprogramming factors are expressed in a somatic cell to successfully reprogram the somatic cell. In other embodiments, at least three reprogramming factors are expressed in a somatic cell to successfully reprogram the somatic cell.

iPSCs may be derived by methods known in the art, including the use integrating viral vectors (e.g., lentiviral vectors, inducible lentiviral vectors, and retroviral vectors), excisable vectors (e.g., transposon and foxed lentiviral vectors), and non-integrating vectors (e.g., adenoviral and plasmid vectors) to deliver the genes that promote cell reprogramming (Takahashi, K. and Yamanaka, S., "Induction of Pluripotent Stem Cells from Mouse Embryonic and Adult Fibroblast Cultures by Defined Factors," Cell 126:663-676 (2006); Okita. et al., "Generation of Germline-Competent Induced Pluripotent Stem Cells," Nature 448:313-317 (2007); Nakagawa et al., Nat. Biotechnol. 26:101-106 (2007); Takahashi et al., "Induction of Pluripotent Stem Cells from Adult Human Fibroblasts by Defined Factors,"

Cell 131:1-12 (2007); Meissner et al., "Direct Reprogramming of Genetically Unmodified Fibroblasts into Pluripotent Stem Cells," Nat. Biotech. 25:1177-1181 (2007); Yu et al., "Induced Pluripotent Stem Cell Lines Derived from Human Somatic Cells," Science 318:1917-1920 (2007); Park et al., "Reprogramming of Human Somatic Cells Pluripotency with Defined Factors," Nature 451:141-146 (2008); and U.S. Patent Application Publication No. 2008/0233610, which are hereby incorporated by reference in their entirety). Other methods for generating IPS cells include those disclosed in WO2007/069666, WO2009/006930, WO2009/006997, WO2009/007852, WO2008/118820, U.S. Patent Application Publication No. 2011/0200568 to Ikeda et al., U.S. Patent Application Publication No 2010/0156778 to Egusa et al., U.S. Patent Application Publication No 2012/0276070 to Musick, and U.S. Patent Application Publication No 2012/0276636 to Nakagawa, Shi et al., "Induction of Pluripotent Stem Cells from Mouse Embryonic Fibroblasts by Oct4 and Klf4 with Small-Molecule Compounds" Cell Stem Cell 3 (5): 568-574 (2008), Kim et al., "Pluripotent Stem Cells Induced from Adult Neural Stem Cells by Reprogramming with Two Factors," Nature 454:646-650 (2008), Kim et al., "Oct4-induced Pluripotency in Adult Neural Stem Cells," Cell 136 (3): 411-419 (2009), Huangfu et al., "Induction of Pluripotent Stem Cells from Primary Human Fibroblasts with Only Oct4 and Sox2," Nat. Biotechnol. 26:1269-1275 (2008), Zhao et al., "Two Supporting Factors Greatly Improve the Efficiency of Human iPSC Generation," Cell Stem Cell 3:475-479 (2008), Feng et al., "Reprogramming of Fibroblasts into Induced Pluripotent Stem Cells with Orphan Nuclear Receptor Esrrb," Nat. Cell Biol. 11:197-203 (2009), and Hanna et al., "Direct Reprogramming of Terminally Differentiated Mature B Lymphocytes to Pluripotency" Cell 133 (2): 250-264 (2008), which are hereby incorporated by reference in their entirety.

The methods of iPSC generation described above can be modified to include small molecules that enhance reprogramming efficiency or even substitute for a reprogramming factor. These small molecules include, without limitation, epigenetic modulators such as, the DNA methyltransferase inhibitor 5'-azacytidine, the histone deacetylase inhibitor VPA, and the G9a histone methyltransferase inhibitor BIX-01294 together with BayK8644, an L-type calcium channel agonist. Other small molecule reprogramming factors include those that target signal transduction pathways, such as transforming growth factor beta (TGF-β) inhibitors and kinase inhibitors (e.g., kenpaullone) (see review by Sommer and Mostoslavsky, "Experimental Approaches for the Generation of Induced Pluripotent Stem Cells," Stem Cell Res. Ther. 1:250-264 (2010), which is hereby incorporated by reference in its entirety).

Methods of obtaining highly enriched preparations of glial progenitor cells from the iPSCs that are suitable for making the chimeric non-human mammal models described herein are disclosed in WO2014/124087 to Goldman and Wang, and Wang et al., "Human iPSC-Derived Oligodendrocyte Progenitors Can Myelinate and Rescue a Mouse Model of Congenital Hypomyelination," Cell Stem Cell 12 (2): 252-264 (2013), which are hereby incorporated by reference in their entirety.

In some embodiments, the human neurodegenerative disorder specific glial cells of the chimeric non-human mammal model described herein are derived from embryonic stem cells. Human Embryonic stem cells provide a virtually unlimited source of clonal/genetically modified cells potentially useful for tissue replacement therapies. Methods of obtaining highly enriched preparations of glial progenitor cells from embryonic cells that are suitable for making the chimeric non-human mammal model of the present disclosure are described herein as disclosed in Wang et al., "Human iPSC-Derived Oligodendrocyte Progenitor Cells can Myelinate and Rescue a Mouse Model of Congenital Hypomyelination," Cell Stem Cell 12:252-264 (2013), which is hereby incorporated by reference in its entirety.

In some embodiments, the human glial cells of the chimeric non-human mammal are derived from human fetal tissue. Glial progenitor cells can be extracted from fetal brain tissue containing a mixed population of cells directly by using the promoter specific separation technique as described in U.S. Patent Application Publication Nos. 20040029269 and 20030223972 to Goldman, which are hereby incorporated by reference in their entirety. This method involves selecting a promoter which functions specifically in glial progenitor cells, and introducing a nucleic acid encoding a marker protein under the control of said promoter into the mixed population cells. The mixed population of cells is allowed to express the marker protein and the cells expressing the marker protein are separated from the population of cells, with the separated cells being the glial progenitor cells. Human glial progenitor cells can be isolated from ventricular or subventricular zones of the brain or from the subcortical white matter.

Glial progenitor cells can be extracted from brain tissue containing a mixed population of cells directly by using the promoter specific separation technique, as described in U.S. Patent Application Nos. 20040029269 and 20030223972 to Goldman, which are hereby incorporated by reference in their entirety. This method involves selecting a promoter which functions specifically in glial progenitor cells, and introducing a nucleic acid encoding a marker protein under the control of said promoter into the mixed population cells. The mixed population of cells is allowed to express the marker protein and the cells expressing the marker protein are separated from the population of cells, with the separated cells being the glial progenitor cells.

Glial specific promoters that can be used for isolating glial progenitor cells from a mixed population of cells include the CNP promoter (Scherer et al, "Differential Regulation of the 2',3'-cyclic nucleotide 3'phosphodiesterase Gene During Oligodendrocyte Development," Neuron 12:1363-75 (1994), which is hereby incorporated by reference in its entirety), an NCAM promoter (Hoist et al., J. Biol. Chem. 269:22245-52 (1994), which is hereby incorporated by reference in its entirety), a myelin basic protein promoter (Wrabetz et al., "Analysis Of The Human MBP Promoter In Primary Cultures Of Oligodendrocytes: Positive And Negative Cis-Acting Elements In The Proximal MBP Promoter Mediate Oligodendrocyte-Specific Expression Of MBP," J. Neurosci. Res. 36:455-71 (1993), which is hereby incorporated by reference in its entirety), a JC virus minimal core promoter (Krebs et al., J. Virol. 69:2434-42 (1995), which is hereby incorporated by reference in its entirety), a myelin-associated glycoprotein promoter (Laszkiewicz et al., "Structural Characterization of Myelin-associated Glycoprotein Gene Core Promoter," J. Neurosci. Res. 50 (6): 928-36 (1997), which is hereby incorporated by reference in its entirety), or a proteolipid protein promoter (Cook et al., "Regulation of Rodent Myelin Proteolipid Protein Gene Expression," Neurosci. Lett. 137 (1): 56-60 (1992); Wight et al., "Regulation of Murine Myelin Proteolipid Protein Gene Expression," J. Neurosci. Res. 50 (6): 917-27 (1997); and Cambi et al., Neurochem. Res. 19:1055-60 (1994), which are hereby incorporated by reference in their entirety). See also U.S. Pat. No. 6,245,564 to Goldman et. al., which is hereby incorporated by reference in its entirety.

In some embodiments, the glial progenitor cells are isolated by first removing neurons or neural progenitor cells from the mixed cell population. Where neuronal progenitor cells are to be separated from the mixed population of cells, they can be removed based on their surface expression of neural cell adhesion molecule (NCAM), polysialic acid-NCAM (PSA-NCAM), or any other surface moiety specific to neurons or neural progenitor cells. Neurons or neural progenitor cells may also be separated from a mixed population of cells using the promoter based separation technique. Neuron or neural progenitor specific promoters that can be used for separating neural cells from a mixed population of cells include the Tal tubulin promoter (Gloster et al, J. Neurosci. 14:7319-30 (1994), which is hereby incorporated by reference in its entirety), a Hu promoter (Park et al., "Analysis of Upstream Elements in the HuC Promoter Leads to the Establishment of Transgenic Zebrafish with Fluorescent Neurons," Dev. Biol. 227 (2): 279-93 (2000), which is hereby incorporated by reference in its entirety), an ELAV promoter (Yao et al., "Neural Specificity of ELAV Expression: Defining a *Drosophila* Promoter for Directing Expression to the Nervous System," J. Neurochem. 63 (1): 41-51 (1994), which is hereby incorporated by reference in its entirety), a microtubule associated protein (MAP)-IB promoter (Liu et al., Gene 171:307-08 (1996), which is hereby incorporated by reference in its entirety), or a GAP-43 promoter. See U.S. Pat. No. 6,245,564 to Goldman et. al., which is hereby incorporated by reference in its entirety.

Having selected a promoter specific for the cell of interest, a nucleic acid molecule encoding a protein marker, preferably a green fluorescent protein under the control of the promoter is introduced into a plurality of cells to be sorted. The isolated nucleic acid molecule encoding a green fluorescent protein can be deoxyribonucleic acid (DNA) or ribonucleic acid (RNA, including messenger RNA or mRNA), genomic, recombinant, or mutant, biologically isolated or synthetic as described in U.S. Patent Application No. 20040029269 to Goldman, which is hereby incorporated by reference in its entirety. Other suitable marker proteins include lacZ/beta-galactosidase or alkaline phosphatase.

Standard techniques are then used to place the nucleic acid molecule encoding the marker protein under the control of the chosen cell specific promoter. Generally, this involves the use of restriction enzymes and ligation.

The resulting construct, which comprises the nucleic acid molecule encoding the marker protein under the control of the selected promoter (itself a nucleic acid molecule) (with other suitable regulatory elements if desired), is then introduced into a plurality of cells which are to be sorted and then sorting. Techniques for introducing the nucleic acid molecules of the construct into the plurality of cells and then sorting the cells are described in U.S. Patent Application No. 20040029269 to Goldman et al., which is hereby incorporated by reference in its entirety.

Once the nucleic acid molecule encoding the marker protein is introduced into a plurality of cells, the promoter which controls expression of the marker protein only functions in the cell of interest. Therefore, the marker protein is only expressed in the cell of interest and those cells can be identified from among the plurality of cells by the expression of the marker protein (e.g. fluorescence of the green fluorescent protein (GFP) using any suitable means of fluorescent detection). For GFP, cells may be identified using epifluorescence optics, and can be physically picked up and brought together by Laser Tweezers (Cell Robotics Inc., Albuquerque, N. Mex.). Alternatively, the cells can be separated in bulk through fluorescence activated cell sorting, a method that effectively separates the fluorescent cells from the non-fluorescent cells.

As an alternative to using promoter-based cell sorting to recover glial progenitor cells from the mixed population, an immunoseparation procedure can be utilized. In a positive immunoselection technique, the desired cells (i.e. glial progenitor cells) are isolated based on proteinaceous surface markers naturally present on the progenitor cells. For example, the surface marker A2B5 is an initially expressed early marker. See Nunes et al., "Identification and Isolation of Multipotential Neural Progenitor Cells from the Adult Human White Matter," Soc. Neurosci. Abstr. (2001), which is hereby incorporated by reference. Using an antibody specific to that marker, glial progenitor cells can be separated from a mixed population of cell types. Using an antibody specific to A2B5, glial progenitor cells can be separated from a mixed population of cell types. Similarly, the surface marker CD44 identifies astrocyte-biased glial progenitor cells (Liu et al., "CD44 Expression Identifies Astrocyte-Restricted Precursor Cells," Dev. Biol. 276:31-46 (2004), which is hereby incorporated by reference in its entirety).

Using CD44-conjugated microbead technology, astrocyte-biased glial progenitor cells can be separated from a mixed population of cell types. Oligodendrocyte-biased glial progenitor cells can be separated from a mixed population of cell types based on expression of platelet-derived growth factor receptor alpha (PDGFαR), the PDGFαR ectodomain CD140a, or CD9. Cells expressing markers of non-glial cell types (e.g., neurons, inflammatory cells, etc.) can be removed from the preparation of glial cells to further enrich the preparation for the desired glial cell type using immunoseparation techniques. For example, the glial progenitor cell population is preferably negative for a PSA-NCAM marker and/or other markers for cells of neuronal lineage, negative for one or more inflammatory cell markers, e.g., negative for a CD11 marker, negative for a CD32 marker, and/or negative for a CD36 marker, which are markers for microglia. Exemplary microbead technologies include MACS® Microbeads, MACS® Columns, and MACS® Separators. Additional examples of immunoseparation are described in Wang et al., "Prospective Identification, Direct Isolation, and Expression Profiling of a Telomerase Expressing Subpopulation of Human Neural Stem Cells, Using Sox2 Enhancer-Directed FACS," J. Neurosci. 30:14635-14648 (2010); Keyoung et al., "High-Yield Selection and Extraction of Two Promoter-Defined Phenotypes of Neural Stem Cells from the Fetal Human Brain," Nat. Biotechnol. 19:843-850 (2001); and Windrem et al., "Neonatal Chimerization with Human Glial Progenitor Cells can both Remyelinate and Rescue the Otherwise Lethally Hypomyelinated Shiverer Mouse," Cell Stem Cell 2:553-565 (2008), which are hereby incorporated by reference in their entirety.

Alternatively, or in combination with the positive immunoselection method described above, a mixed cell population can be depleted of undesirable cell types, leaving the desired cell population. This method involves separating cells based on proteinaceous surface markers that are specific to cell populations other than the glial progenitor cells (i.e. neuronal cells, endothelial cells, etc.) and retaining the glial progenitor cell population. In accordance with the method of producing the non-human mammal model of a human neurodegenerative disorder, the selected preparation of administered human neurodegenerative disorder specific glial cells comprise at least about 80% glial cells, including, for example, about 80%, 85%, 90%, 95%, 96%, 97%, 98%, 99%, 100% glial cells. The selected preparation of glial cells can be relatively devoid (e.g., containing less than 20, 15, 10, 9, 8, 7, 6, 5, 4, 3, 2, or 1%) of other cell types such as neurons or cells of neuronal lineage, fibrous astrocytes and cells of fibrous astrocyte lineage, and pluripotential stem cells (like embryonic stem cells). Optionally, example cell populations are substantially pure populations of glial cells.

Cell specific antibodies for immunoseparation techniques can be labeled with a fluorescent, biotin, or hapten label to facilitate separation of cells to which they bind.

Alternatively, the antibodies can be attached to paramagnetic beads so that cells which bind to the beads through the attached antibodies can be recovered by a bio magnetic separation process. Any other suitable method for cell separation known in the art, including attachment to and disattachment from solid phase (i.e. immunopanning), is also within the scope of the present application.

To produce the chimeric non-human mammal model described herein, a population of isolated human neurodegenerative disorder specific glial cells is introduced into multiple locations within the forebrain and/or brain stem of a non-human mammal. The population of cells introduced may be a population of glial progenitor cells and/or astrocyte cells. As described above, the glial progenitor cells and/or astrocytes can be derived from any suitable source, e.g., iPSCs, embryonic stem cells, fetal tissue, glial progenitor cells. As described supra, the glial progenitor cells and/or astrocytes can be derived from a patient having the neurodegenerative disease. Alternatively, the glial progenitor cells or astrocytes are engineered to a neurodegenerative disorder specific state. Suitable methods of introducing cells into the forebrain and/or brain stem of non-human mammals are well known to those of skill in the art and include, but are not limited to, injection, deposition, and grafting as described herein.

The glial progenitor cells can be transplanted bilaterally into multiple sites of the non-mammal host animal. Methods for transplanting nerve tissues and cells into host brains are described by Bjorklund and Stenevi (eds), Neural Grafting in the Mammalian CNS, Ch. 3-8, Elsevier, Amsterdam (1985); U.S. Pat. No. 5,082,670 to Gage et al.; and U.S. Pat. No. 6,497,872 to Weiss et al, which are hereby incorporated by reference in their entirety. In one embodiment, the glial progenitor cells are transplanted bilaterally into multiple sites of the non-mammal host animal as described U.S. Pat. No. 7,524,491 to Goldman, Windrem et al., "Neonatal Chimerization With Human Glial Progenitor Cells Can Both Remyelinate and Rescue the Otherwise Lethally Hypomyelinated Shiverer Mouse," Cell Stem Cell 2:553-565 (2008), Han et al., "Forebrain Engraftment by Human Glial Progenitor Cells Enhances Synaptic Plasticity and Learning Adult Mice," Cell Stem Cell 12:342-353 (2013), and Wang et al., "Human iPSCs-Derived Oligodendrocyte Progenitor Cells Can Myelinate and Rescue a Mouse Model of Congenital Hypomyelination," Cell Stem Cell 12:252-264 (2013), which are hereby incorporated by reference in their entirety). Methods for transplanting nerve tissues and cells into host brains are described In one embodiment, the glial progenitor cells are transplanted bilaterally into multiple sites of the non-mammal host animal as described U.S. Pat. No. 7,524,491 to Goldman, Windrem et al., "Neonatal Chimerization With Human Glial Progenitor Cells Can Both Remyelinate and Rescue the Otherwise Lethally Hypomyelinated Shiverer Mouse," Cell Stem Cell 2:553-565 (2008), Han et al., "Forebrain Engraftment by Human Glial Progenitor Cells Enhances Synaptic Plasticity and Learning Adult Mice," Cell Stem Cell 12:342-353 (2013), and Wang et al., "Human iPSCs-Derived Oligodendrocyte Progenitor Cells Can Myelinate and Rescue a Mouse Model of Congenital Hypomyelination," Cell Stem Cell 12:252-264 (2013), which are hereby incorporated by reference in their entirety). Methods for transplanting nerve tissues and cells into host brains are described by Bjorklund and Stenevi (eds), Neural Grafting in the Mammalian CNS, Ch. 3-8, Elsevier, Amsterdam (1985); U.S. Pat. No. 5,082,670 to Gage et al.; and U.S. Pat. No. 6,497,872 to Weiss et al., which are hereby incorporated by reference in their entirety. Typical procedures include intraparenchymal, intracallosal, intraventricular, intrathecal, and intravenous transplantation., which are hereby incorporated by reference in their entirety.

Intraparenchymal transplantation is achieved by injection or deposition of tissue within the host brain so as to be apposed to the brain parenchyma at the time of transplantation. The two main procedures for intraparenchymal transplantation are: 1) injecting the donor cells within the host brain parenchyma or 2) preparing a cavity by surgical means to expose the host brain parenchyma and then depositing the graft into the cavity (Bjorklund and Stenevi (eds), Neural Grafting in the Mammalian CNS, Ch. 3, Elsevier, Amsterdam (1985), which is hereby incorporated by reference in its entirety). Both methods provide parenchymal apposition between the donor cells and host brain tissue at the time of grafting, and both facilitate anatomical integration between the graft and host brain tissue. This is of importance if it is required that the donor cells become an integral part of the host brain and survive for the life of the host.

Glial progenitor cells can also be delivered intracallosally as described in U.S. Patent Application No. 20030223972 to Goldman. In a preferred embodiment of the present application, glial progenitor cells are delivered directly to the forebrain subcortex, specifically into the anterior and posterior anlagen of the corpus callosum. Glial progenitor cells can also be delivered to the cerebellar peduncle white matter to gain access to the major cerebellar and brainstem tracts. Glial progenitor cells can also be delivered to the spinal cord.

Alternatively, the cells may be placed in a ventricle, e.g. a cerebral ventricle. Grafting cells in the ventricle may be accomplished by injection of the donor cells or by growing the cells in a substrate such as 30% collagen to form a plug of solid tissue which may then be implanted into the ventricle to prevent dislocation of the graft cells. For subdural grafting, the cells may be injected around the surface of the brain after making a slit in the dura.

As indicated supra, the isolated population of human neurodegenerative disorder specific glial cells are introduced into a myelin deficient or myelin depleted non-human mammal. Alternatively, the isolated population of human neurodegenerative disorder specific glial cells are introduced into a normally myelinated non-human mammal.

In another embodiment of the present application, transplantation of the glial progenitor cells can be carried out using intravenous or intrathecal administration as described by Pluchino et al., "Injection of Adult Neurospheres Induces Recovery in a Chronic Model of Multiple Sclerosis," Nature 422 (6933): 678-94 (2003), which is hereby incorporated by reference in its entirety.

Once the human glial progenitor cells are introduced, the mammal is permitted to age, causing the mammal to produce more human glial cells as it ages. In addition, the mammal undergoes myelination as it ages.

After the population of isolated human neurodegenerative disorder specific glial cells is introduced into the forebrain and/or brain stem of the non-human mammal, the non-human mammal is recovered. As used herein, the term "recovering the non-human mammal" refers to a process or means by which the introduced human glial cells are allowed to functionally engraft into the brain of the non-human mammal. Exemplary percentages of human glial cells present in the white matter and/or corpus callosum of the brain and brain stem of the recovered non-human mammal model are described supra.

Survival of the human glial progenitor cells in the host mammal can be examined using various non-invasive scans such as computerized axial tomography (CAT scan or CT scan), nuclear magnetic resonance or magnetic resonance imaging (NMR or MRI) or more preferably positron emission tomography (PET) scans. Postmortem examination of cell survival and integration can be done by histological examination of various brain regions macroscopically, or more preferably using microscopy. Cells can be labeled with any stain visible under light or electron microscopic conditions, more particularly with stains which are specific for host glia cells. Particularly useful are antibodies which specifically identify the human donor cells, including the mouse anti-human nuclei, clone 235-1, and antibodies which demonstrate myelin production by the donor cells, including anti-myelin basic protein antibodies. Transplanted cells can also be identified by prior incorporation of tracer dyes such as rhodamine- or fluorescein-labeled microspheres, fast blue, bisbenzamide or retrovirally introduced histochemical markers such as the lac Z gene which produces beta galactosidase.

IV. Method of Providing Specific Glial Progenitor Cells

Another aspect of the present application relates to a method comprising providing a population of isolated human neurodegenerative disorder specific glial progenitor cells or human neuropsychiatric disorder specific glial progenitor cells or human myelin disease specific glial progenitor cells, the human neurodegenerative disorder specific glial progenitor cells or said human neuropsychiatric disorder specific glial progenitor cells or human myelin disease specific glial progenitor cells being tagged with a first detectable label. This method further involves introducing the population of isolated human neurodegenerative disorder specific glial progenitor cells or human neuropsychiatric disorder specific glial progenitor cells or human myelin disease specific glial progenitor cells with the first detectable label into the brain and/or brain stem of a non-human mammal to produce a chimeric non-human mammal.

This method also involves providing a population of isolated healthy human glial progenitor cells, where the healthy human glial progenitor cells express a second detectable label, which is distinguishable from the first detectable label. This method further involves introducing the population of isolated healthy human glial progenitor cells into the brain and/or brain stem of the chimeric non-human mammal. This method additionally involves recovering, as a result of the introducing step, the population of isolated healthy human glial progenitor cells into the brain and/or brain stem of the chimeric non-human mammal, a treated, chimeric non-human mammal, having, in its brain and/or brain stem, healthy human glial cells expressing the second detectable label at least partially replacing human neurodegenerative disorder specific glial cells or human neuropsychiatric disorder specific glial cells or human white matter disease specific glial cells tagged with the first detectable label.

In aspects of the present application, the method further comprises isolating from the chimeric non-human mammal the population of glial cells from where native glial cell are at least partially replaced.

The method of providing a population of isolated healthy human glial progenitor cells, said healthy human glial progenitor cells expressing a second detectable label, which is distinguishable from the first detectable label may use any of the methods for isolating human glial progenitors cells to the brain as disclosed supra.

The method of introducing the population of isolated healthy human glial progenitor cells into the brain and/or brain stem of the chimeric non-human mammal may use any of the methods for introducing human glial progenitor cells to the brain as disclosed supra.

The method of recovering, as a result of said introducing the population of isolated healthy human glial progenitor cells into the brain and/or brain stem of the chimeric non-human mammal, a treated, chimeric non-human mammal, having, in its brain and/or brain stem, healthy human glial cells expressing the second detectable label at least partially replacing human neurodegenerative disorder specific glial cells or human neuropsychiatric disorder specific glial cells or human white matter disease specific glial cells tagged with the first detectable label may use any of the methods for recovering as disclosed supra.

In aspects of the present application, the method further comprises imaging the brain and/or brain stem of the treated, chimeric non-human mammal to produce an image showing glial cells with the first and second detectable labels. In aspects of the present application, the method further comprises evaluating the image to determine whether transplantation of the healthy human glial progenitor cells into a human subject is useful in treating the human neurodegenerative disorder or the human neuropsychiatric disorder or human myelin disease.

In aspects of the present application, the method further comprises isolating from the treated chimeric non-human mammal the population of glial cells from where glial cells expressing the second detectable label at least partially replace glial cells with the first label.

In aspects of the present application, the method wherein the non-human mammal into which the population of isolated human neurodegenerative disorder specific glial progenitor cells or human neuropsychiatric disorder specific glial progenitor cells or human myelin disease specific glial progenitor cells with the first detectable label is introduced is a pre-natal or a neo-natal non-human animal. In aspects of the present application, the method wherein the non-human animal into which the population of isolated healthy human glial progenitor cells expressing the second detectable label is introduced is an adult non-human animal.

Another aspect of the present application relates to a method comprising providing a population of isolated human neurodegenerative disorder specific glial progenitor cells or human neuropsychiatric disorder specific glial progenitor cells or human myelin disease specific glial progenitor cells, where the human neurodegenerative disorder specific glial progenitor cells or said human neuropsychiatric disorder specific glial progenitor cells or human myelin disease specific glial progenitor cells are tagged with a first detectable label. This method further involves providing a population of isolated healthy human glial progenitor cells, with the healthy human glial progenitor cells expressing a second detectable label, which is distinguishable from the first detectable label. This method additionally involves co-introducing (1) the population of isolated human neuro- degenerative disorder specific glial progenitor cells or human neuropsychiatric disorder specific glial progenitor cells or human myelin disease specific glial progenitor cells with the first detectable label and (2) the population of isolated healthy human glial progenitor cells expressing the second detectable label into the brain and/or brain stem of a non-human mammal. This method also includes recovering, as a result of said co-introducing, a treated chimeric non-human mammal having, in its brain and/or brain stem, healthy human glial cells expressing the second detectable label and human neurodegenerative disorder specific glial cells or human neuropsychiatric disorder specific glial cells or human white matter disease specific glial cells tagged with the first detectable label.

In aspects of the present application, the method further comprises imaging the brain and/or brain stem of the treated chimeric non-human mammal to produce an image showing glial cells with the first and second detectable labels. In aspects of the present application, the method further comprises evaluating the image to determine whether transplantation of the healthy human glial progenitor cells into a human subject is useful in treating the human neurodegenerative disorder or the human neuropsychiatric disorder or the human myelin disease.

To determine whether transplantation of the healthy human glial progenitor cells into a human subject is useful in treating the human neurodegenerative disorder or the human neuropsychiatric disorder or the human myelin disease, the volume of cells expressing the second detectable marker may be compared to the volume of cells expressing the first detectable marker. To map human cell distributions within the mouse brain, the brain is cut into equidistantly spaced sections spanning the distance of a brain structure of interest. In some aspects of the present application, the brain structure of interest is the striatum. Sections are immunolabeled with a proliferation marker. In an aspect of the present application, the proliferation marker is marker of proliferation Ki-67 (MKI67) or Ki76. Sections may also be immunostained for any other marker of interest, such as markers for glia (glial fibrillary acidic protein, GFAP) and oligodendrocytes (oligodendrocyte transcription factor, Olig2). After imaging, the images of the sections are digitally aligned and reconstructed into a three-dimensional structure. The boundaries of the brain structure are determined and the volume is determined. Cells in the brain structure are counted to determine the cell density of cell types.

Specifically, the cell density of cells expressing the first detectable marker and the density of cells expressing the second detectable marker is determined. The proportion of cells expressing the second detectable marker compared to the first detectable marker to determine whether transplantation of the healthy human glial progenitor cells was successful.

In aspects of the present application, the method further comprises isolating from the treated chimeric non-human mammal the population of glial cells from where glial cells expressing the second detectable label and glial cells with the first label are present.

In aspects of the present application, the method wherein the human neurodegenerative disorder is selected from the group consisting of Huntington's disease, frontotemporal dementia, Parkinson's disease, multisystem atrophy, and amyotrophic lateral sclerosis. In aspects of the present application, the method wherein the human neuropsychiatric disorder is selected from the group consisting of schizophrenia, autism spectrum disorder, and bipolar disorder. In aspects of the present application, the method wherein the human myelin disease, wherein the human myelin disease is a leukodystrophy or a white matter disease.

In aspects of the present application, the method wherein said introducing steps are independently carried out by intraparenchymal, intracallosal, intraventricular, intrathecal, intracerebral, intracisternal, or intravenous transplantation. In aspects of the present application, the method wherein said introducing steps independently result in replacement of human glial progenitor cells previously present in the forebrain, striatum, and/or cerebellum of the non-human mammal.

Another aspect of the present application relates to a method comprising providing a population of isolated diseased human selected organ specific progenitor cells tagged with a first detectable label. This method further involves introducing the population of isolated diseased human selected organ specific progenitor cells with the first detectable label into the selected organ of a non-human mammal to produce a chimeric non-human mammal. This method further involves providing a population of isolated healthy human selected organ specific progenitor cells expressing a second detectable label, which is distinguishable from the first detectable label. This method also involves introducing the population of isolated healthy human selected organ specific progenitor cells into the selected organ of the chimeric non-human mammal. This method further includes recovering, as a result of the introducing step the population of isolated healthy human selected organ specific progenitor cells into the selected organ of the chimeric non-human mammal, a treated chimeric non-human mammal with the selected organ having healthy human organ specific cells expressing the second detectable label and diseased human selected organ specific cells tagged with the first detectable label.

Another aspect of the present application relates to a method comprising providing a population of isolated diseased human selected organ specific progenitor cells tagged with a first detectable label and providing a population of isolated healthy human selected organ specific progenitor cells expressing a second detectable label, which is distinguishable from the first detectable label. The population of isolated diseased human selected organ specific progenitor cells with the first detectable label and the population of isolated healthy human selected organ specific progenitor cells expressing a second detectable label are co-introduced into the selected organ of a non-human mammal. As a result of the co-introducing step, a treated chimeric non-human mammal with the selected organ having healthy human organ specific cells expressing the second detectable label and diseased human selected organ specific cells tagged with the first detectable label is recovered.

The method of providing a population of isolated diseased human selected organ specific progenitor cells tagged with a first detectable label may use any of the methods described supra and may be adapted to the selected organ as would be known by a skilled artisan.

The method of introducing the population of isolated diseased human selected organ specific progenitor cells with the first detectable label into the selected organ of a non-human mammal to produce a chimeric non-human mammal may use any of the methods described supra and may be adapted to the selected organ as would be known by a skilled artisan.

The method of recovering, as a result of said introducing the population of isolated healthy human selected organ specific progenitor cells into the selected organ of the chimeric non-human mammal, a treated chimeric non-human mammal with the selected organ having healthy human organ specific cells expressing the second detectable label and diseased human selected organ specific cells tagged with the first detectable label may use any of the methods described supra and may be adapted to the selected organ as would be known by a skilled artisan.

In aspects of the present application, the method further comprises imaging the selected organ of the treated chimeric non-human mammal to produce an image showing cells with the first and second detectable labels. In aspects of the present application, the method further comprises evaluating the image to determine whether transplantation of the healthy human selected organ specific progenitor cells into a human subject is useful in treating a disease of the selected human organ. The method may use any of the methods described supra and may be adapted to the selected organ as would be known by a skilled artisan.

In aspects of the present application, the method wherein the non-human mammal into which the population of isolated diseased human selected organ specific progenitor cells with the first detectable label is introduced is a pre-natal or a neo-natal non-human animal. In aspects of the present application wherein the non-human animal into which the population of isolated healthy human selected organ specific progenitor cells expressing the second detectable label is introduced is an adult non-human animal. The method may use any of the methods described supra and may be adapted to the selected organ as would be known by a skilled artisan.

In aspects of the present application, the method wherein the selected organ is the liver, bone marrow and hematopoietic stem cells, skin, pancreas, heart, lung, and kidney.

The present application is further illustrated by the following examples that should not be construed as limiting. The contents of all references, patents, and published patent applications cited throughout this application, as well as the Figures and Tables, are incorporated herein by reference.

EXAMPLES

Example 1: Materials and Methods

Human Embryonic Stem Cell Lines and Culture Conditions

Sibling human embryonic stem cells (hESCs) lines GENEA019 (WT: 18; 15 CAG; Giorgio, F. P. D., et al., "Non-Cell Autonomous Effect of Glia on Motor Neurons in an Embryonic Stem Cell-Based ALS Model," Nat Neurosci 10:608-614 (2007), which is hereby incorporated by reference in its entirety) and GENEA020 (HD: 48; 17 CAG; Giorgio, F. P. D., et al., "Human Embryonic Stem Cell-Derived Motor Neurons Are Sensitive to the Toxic Effect of Glial Cells Carrying an ALS-Causing Mutation," Cell Stem Cell 3:637-648 (2008), which is hereby incorporated by reference in its entirety) were obtained from GENEA, Inc. (Sydney, Australia). hESC were regularly cultured under feeder-free conditions on 0.55 ug/cm2 human recombinant laminin 521 (Biolamina, cat. no. LN521) coated cell culture flasks with mTeSR1 medium (StemCell Technologies, cat. no. 85850). Daily medium changes were performed. hESCs were routinely passaged at 80% confluency onto freshly coated flasks. Passaging was performed using ReLeSR (StemCell Technologies, cat. no. 05872). All hESCs and differentiated cultures were maintained in a 5% CO2 incubator at 37° C. and routinely checked for contamination and *mycoplasma* free status.

Generation of Fluorescent Reporter hESCs

For ubiquitous and distinct fluorescent labeling of wild-type (WT) and Huntington's disease (HD) cells (FIG. 1), reporter constructs driving expression of either mCherry or EGFP (enhanced green fluorescent protein) were inserted into the AAVS1 safe-harbor locus of WT GENEA019 and HD GENEA020 hESCs, respectively, using a modified version of the CRISPR-Cas9 (clustered regularly interspaced short palindromic repeats-CRISPR associated protein 9) mediated strategy previously described in (Yamanaka, K. et al., "Astrocytes as Determinants of Disease Progression in Inherited Amyotrophic Lateral Sclerosis," Nat Neurosci 11:251-253 (2008), which is hereby incorporated by reference in its entirety). To prepare hESCs for plasmid delivery by electroporation, hESC were harvested as single cell suspension following dissociation with Accutase (StemCell Technologies, cat. no. 07920), washed in culture medium, and counted with the automated cell counter NucleoCounter NC-200 (ChemoMetec). Per electroporation, a total of $1.5 \times 10^6$ cells were mixed with 5 μg of the AAVS1 targeting CRISPR-Cas9 plasmid (pXAT2) and 5 μg of reporter donor plasmid (pAAVS1-P-CAG-mCh or pAAVS1-P-CAG-GFP). pXAT2 (Addgene plasmid no. 80494), pAAVS1-P-CAG-mCh (Addgene plasmid no. 80491) and pAAVS1-P-CAG-GFP (Addgene plasmid no. 80492) were a gift from Knut Woltjen. Electroporation was performed using an Amaxa 4D-Nucleofector (Lonza) with the P3 primary cell kit (Lonza, cat. no. V4XP-3024) according to manufacturer's guidelines. After nucleofection, the electroporated hESC suspensions were transferred to 10 cm cell culture dishes and cultured with mTeSR1 supplemented with 10 μM Y-27632 (Tocris, cat. no. 1254) for the first 24 h. Electroporated hESCs were grown for 48-72 h and then treated with 0.5 μg/μL puromycin (ThermoFisher, cat. no. A1113803). Electroporated hESC cultures were kept under puromycin until individual colonies were large enough to be picked manually. Colonies were assessed by fluorescent microscopy and transferred to a 96-well plate based on uniformity of fluorescent protein expression. Following their expansion, each clone was split for further expansion and for genotyping. For genotyping, DNA was extracted using the prepGEM Tissue DNA extraction kit (Zygem). Correctly targeted transgenic integrations in the AAVS1 locus were detected by PCR using the following primers: dna803: TCGACTTCCCCTCTTCCGATG (SEQ ID NO; 1) and dna804: CTCAGGTTCTGGGAGAGGGTAG (SEQ ID NO; 2); while the zygosity of the integrations was determined by the presence or absence of a WT allele using an additional primer: (dna803 and dna183: GAGCCTAGGGCCGGGATTCTC (SEQ ID NO; 3)). hESC clones with correctly targeted insertions were cryopreserved with Pro-Freeze CDM medium (Lonza, cat. no. BEBP12-769E) and expanded for karyotyping and array comparative genomic hybridization (aCGH) characterization prior to experimental application.

Karyotyping and aCGH

The karyogram of generated reporter hESC lines was analyzed on metaphase spreads by G-banding (Institut für Medizinishche Genetik und Angewandte Genomik, Universitätsklinikum Tübingen). All hESC lines used in this study harbor a normal karyotype. Additionally, acquired copy number variants (CNVs) and loss-of-heterozygosity regions (LOH) were assessed by aCGH (Cell Line Genetics). A variety of CNVs and LOH within and outside of normal range were identified (FIG. 2), but none that are expected to influence the outcomes of competitive interactions between the clones.

Derivation of hGPCs from Reporter WT and HD hESCs

Human GPCs were derived from both reporter WT and HD hESCs using our well-established protocol (Lee, Y. et al., "Oligodendroglia Metabolically Support Axons and Contribute to Neurodegeneration," Nature 487:443-448 (2012), which is hereby incorporated by reference in its entirety). with minor modifications to the embryoid body (EB) generation step. Details on the EB generation step are included in the supplementary information. Cells were collected for xenotransplantation between 150 and 200 DIV, at which time the cultures derived from both WT-mCherry and HD-EGFP hESCs were rich in PDGFRα+/CD44+ bipotential glial progenitor cells. A detailed characterization of the generated cultures by flow cytometry and immunocytochemistry can be found in FIG. 3 and FIG. 18, Panels A and B.

Cell Preparation for Xenotransplantation

To prepare cells for xenotransplantation, glial cultures were collected in Ca2+/Mg2+-free Hanks' balanced salt solution (HBSS (−/−); ThermoFisher, cat. no. 14170112), mechanically dissociated to small clusters by gentle pipetting and counted with a hemocytometer. The cell suspension was then spun and resuspended in cold HBSS (−/−) at a final concentration of 105 cells/μL and kept on ice until transplanted.

Hosts and Xenotransplantation Paradigms

In vivo modelling of human glial striatal repopulation: To generate human-mouse chimeras harboring mHTT-expressing human glia (HD chimeras), newborn immunocompromised Rag1 (−/−) pups (Meyer, K. et al. "Direct Conversion Of Patient Fibroblasts Demonstrates Non-Cell Autonomous Toxicity Of Astrocytes To Motor Neurons In Familial And Sporadic ALS." Proc National Acad Sci 111:829-832 (2014), which is hereby incorporated by reference in its entirety) were cryoanesthetized, secured in a custom baked clay stage, and injected bilaterally with 100,000 HD-EGFP glia (50,000 per hemisphere) into the presumptive striatum within 48 h from birth. Cells were delivered using a 10 μL syringe (Hamilton, cat. no. 7653-01) with pulled glass pipettes at a depth of 1.2 to 1.4 mm. The pups were then returned to their mother, until weaned. To model human glial striatal repopulation, 36 weeks old HD chimeras were anesthetized by ketamine/xylazine and secured in a stereotaxic frame. 200,000 WT glia were delivered bilaterally using a 10 μL syringe and metal needle into the humanized striatum (AP: +0.8 mm; ML: ±1.8 mm; DV: −2.5 to −2.8 mm). To minimize damage, cells were infused at a controlled rate of 175 nL/min using a controlled micropump system (World Precision Instruments). Backflow was prevented by leaving the needle in place for an additional 5 min. Experimental animals were compared to HD chimeric littermates that did not receive WT glia and to non-chimeric Rag1(−/−) mice that received WT glia at 36 weeks of age following this exact procedure.

Neonatal Striatal Co-Engraftments

To model the cell-intrinsic effects of mHTT-expression on the outcomes of competition between human glia, newborn Rag1(−/−) mice were injected following the same neonatal striatal xenotransplant protocol above described, but instead a total of 200,000 human glia (100,000 per hemisphere) composed of a 1:1 mixture of glia derived from WT-mCherry and HD-EGFP hESCs were delivered. Control littermates received injections composed of either WT-mCherry or HD-EGFP human glia.

Aseptic technique was used for all xenotransplants. All mice were housed in a pathogen-free environment, with ad libitum access to food and water, and all procedures were performed in agreement with protocols approved by the University of Rochester Committee on Animal Resources.

Tissue Processing

Experimental animals were perfused with HBSS (−/−) followed by 4% PFA. The brains were removed, post-fixed for 2 h in 4% PFA and rinsed 3× with PBS. They were then incubated in 30% sucrose solution (Sigma-Aldrich, cat. no. S9378) until equilibrated at which point, they were embedded in OCT in a sagittal orientation (Sakura, cat. no. 4583), frozen in 2-methylbutane (Fisher Scientific, cat. no. 11914421) at temperatures between −60 and −70° C. and transferred to a −80° C. freezer. The resulting blocks were then cut in 20 μm sections on a CM1950 cryostat (Leica), serially collected on adhesion slides and stored at −20° C. until further use.

Immunostaining

Figure 4:
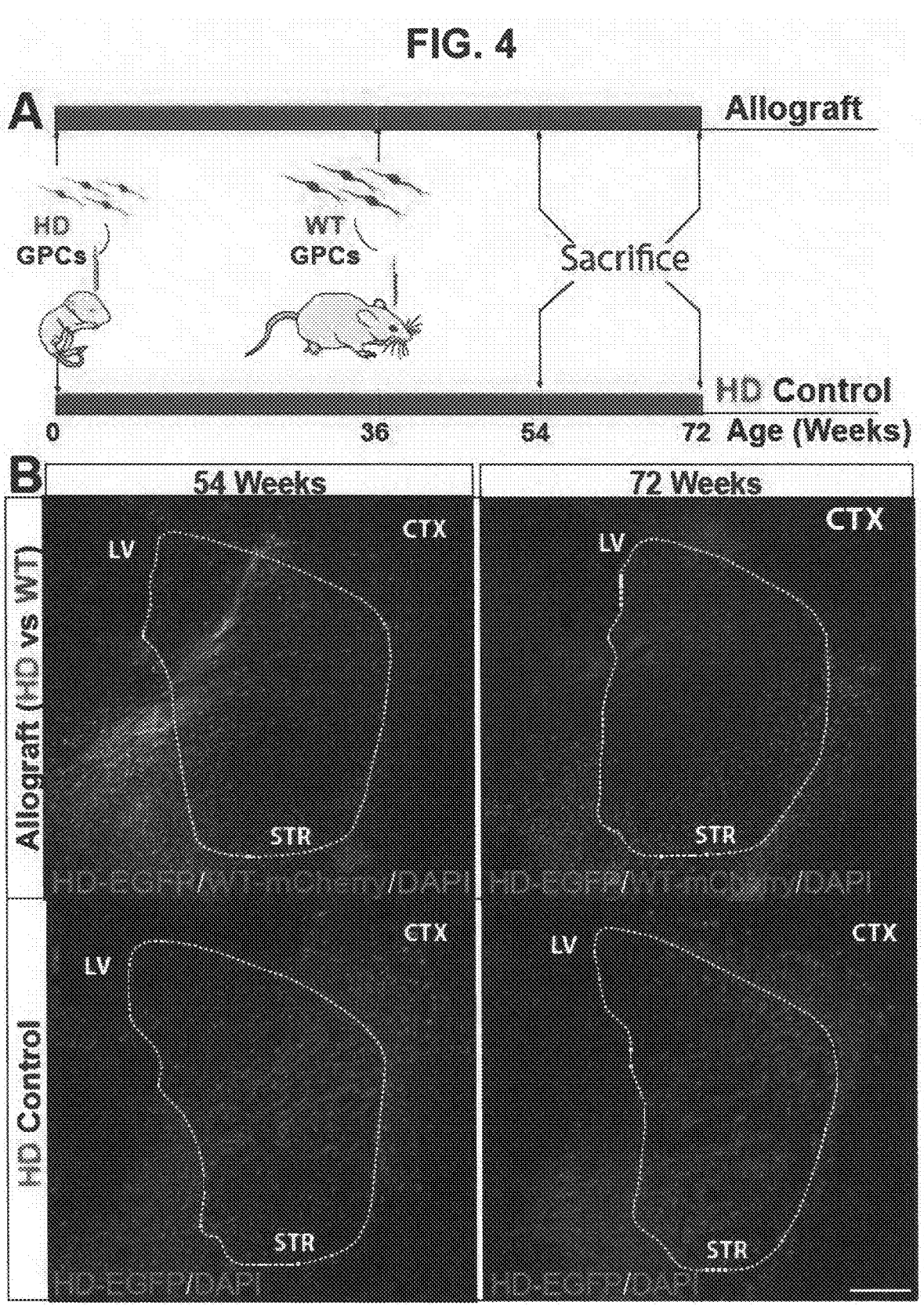
FIG. 4 shows adult-transplanted WT human GPCs outcompete and replace neonatally resident HD hGPCs. Panel A. Experimental design and analytical endpoints. Panel B—Engraftment of WT glia (mCherry+, red) into the striatum of HD chimeras yielded progressive replacement of HD glia (EGFP+, green) creating extensive exclusive domains in their advance. Dashed outlines (white) demarcate the striatal outlines within which human cells were mapped and quantified. Panel C-D. The border between advancing WT and retreating HD hGPCs was typically well-delineated, such that exclusive domains are formed as WT GPCs (Olig2+, white) displace their HD counterparts. Panel E. GPC replacement precedes astrocytic replacement, as within regions colonized by WT hGPCs, stray HD astrocytes (hGFAP+, white) could still be found. Panel F. Mapped distributions of human glia in host striata. Human glia were mapped in 15 equidistant sections (5 are shown as example) and reconstructed in 3D. Their distribution was measured radially as a function of distance to the injection site. Panel G. Rendered examples of mapped striata. Panel H. Volumetric quantification shows that WT gradually replaced their HD counterparts as they expanded from their implantation site; H1: WT vs. HD (Allograft; n=8 for 54 weeks, n=7 for 72 weeks). The advance of WT cells was accompanied by a progressive elimination of HD glia from the tissue, relative to untransplanted HD chimeras (HD control); H2: HD (Allograft; n=8 for 54 weeks, n=7 for 72 weeks) vs. HD Control (n=4 for both timepoints; 2-way ANOVA with Šidák's multiple comparisons tests. **P<0.0001, *P<0.001, **P<0.01, *P<0.05; data are presented as means±SEM). Panel I. At the boundary between WT and HD glia, a high incidence of Ki67+ (white) cells can be seen exclusively within the WT glial population. Panel I'. Higher magnification of two WT daughter cells at the edge of the competitive boundary. Panel J. Quantification of Ki67+ glia within each population as a function of time shows a significant proliferative advantage by WT glia, that is sustained throughout the experiment. HD control: 54 wks (n=4), 72 wks (n=4); WT control: 54 wks (n=5), 72 wks: n=3; WT vs. HD allograft: 54 wks (n=5), 72 wks (n=3). Comparisons by 2-way ANOVA with Šidák's multiple comparisons tests; mean±SEM. STR, striatum (caudate-putamen); LV, lateral ventricle; CTX, cortex. Dashed rectangle (orange) represents inset (B'). Scale: Panel B, 500 μm; Panel C', 100 μm; Panel D, 50 μm; Panel E, 10 μm; Panel I, 100 μm; Panel I', 10 μm.
Figure 4:
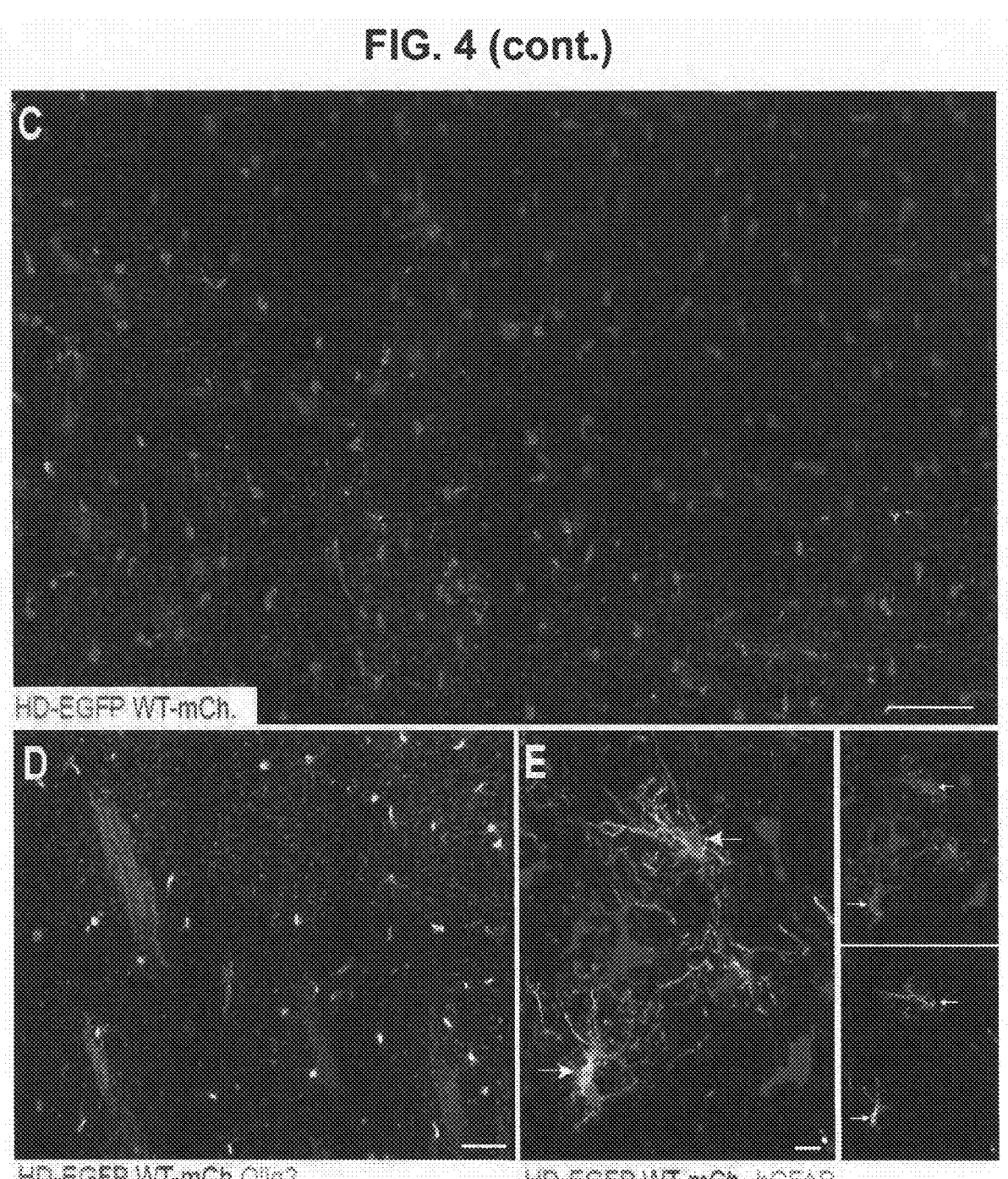
Figure 4:
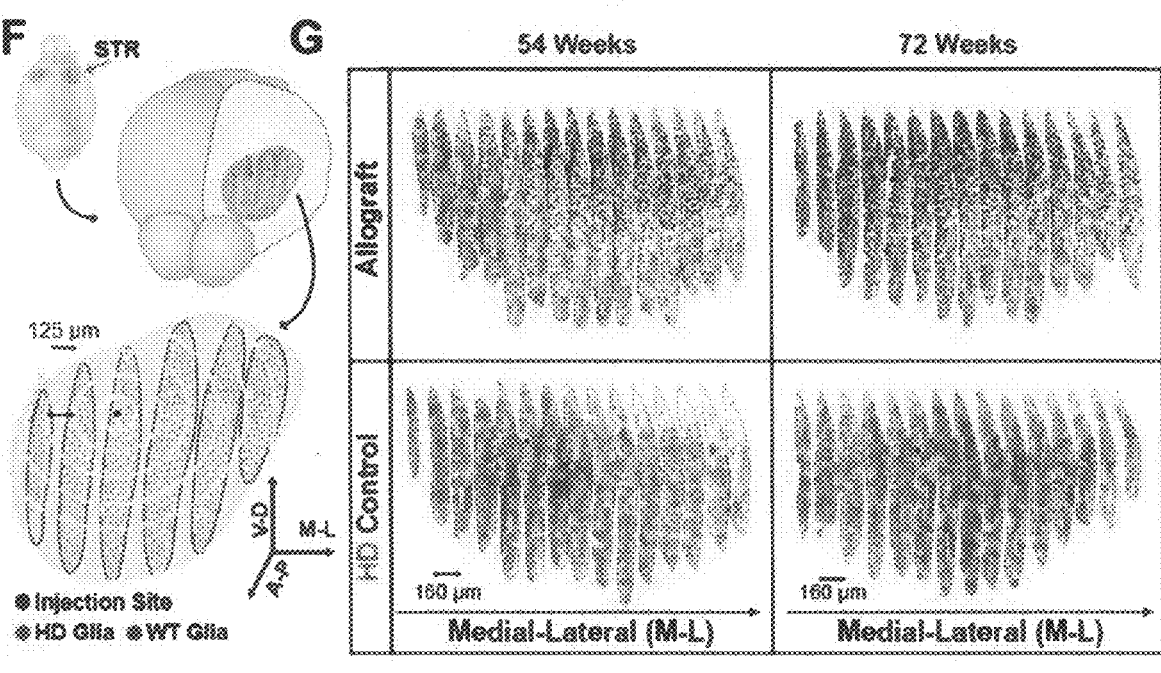
Figure 4:
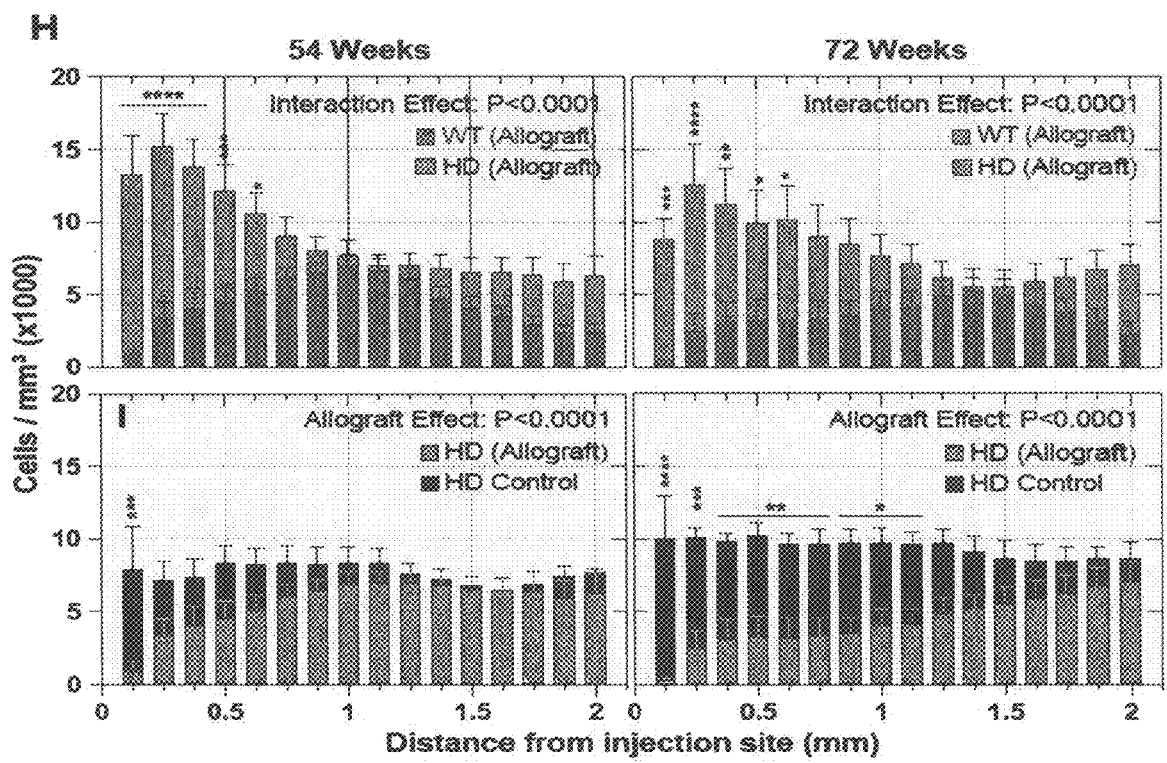
Figure 4:
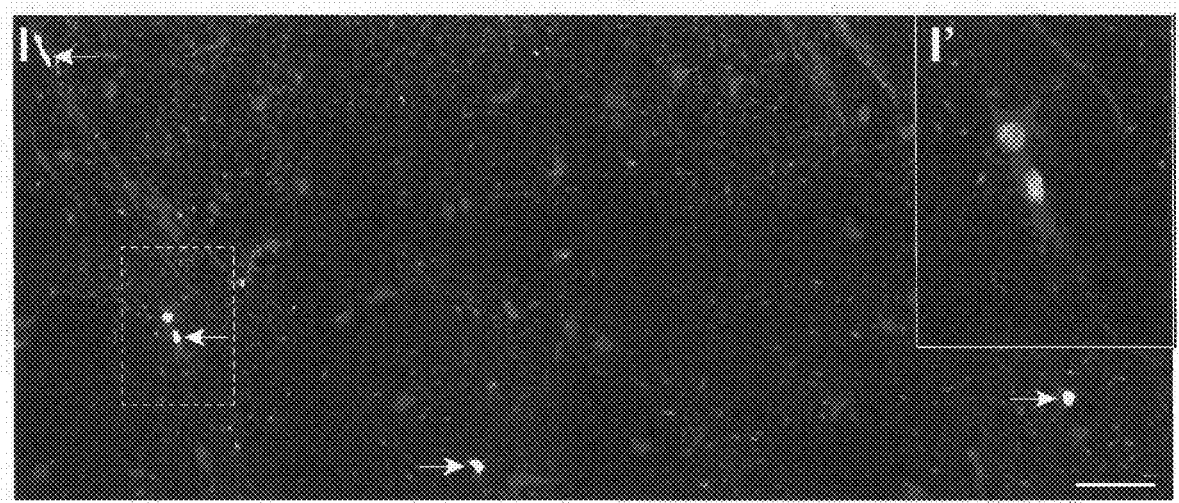
Figure 4:
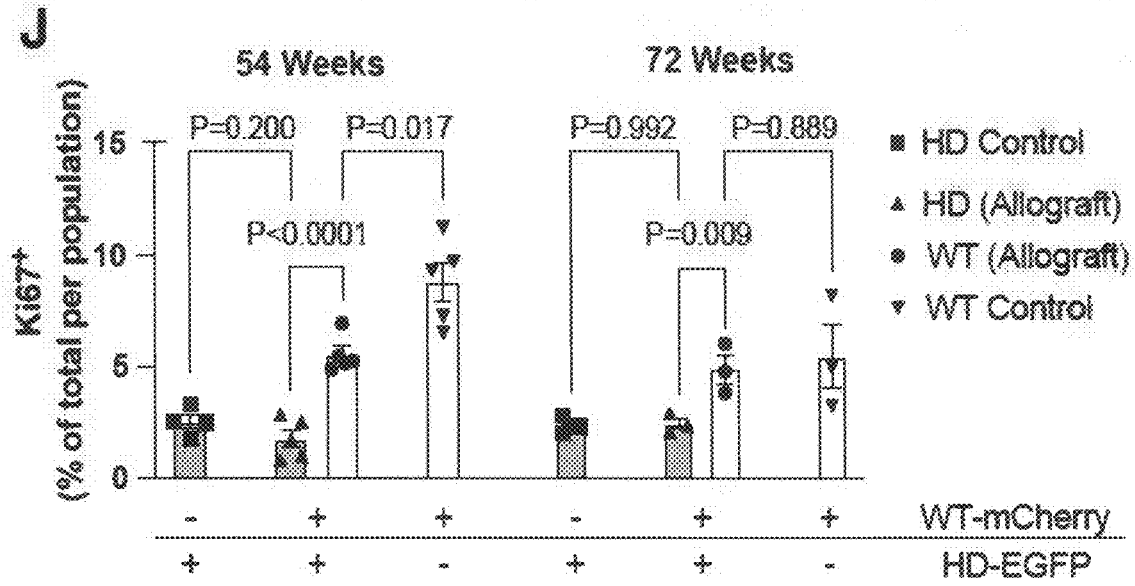

Phenotyping of human cells was accomplished by immunostaining for their respective fluorescent reporter, together with a specific phenotype marker: Olig2 (oligodendrocyte transcription factor, marking GPCs) and GFAP (glial fibrillary acidic protein, marking astrocytes). Fluorescent reporters were used as makers for human cells as their expression remained ubiquitous throughout the animal's life (FIG. 4). In animals that received a 1:1 mixture of WT-mCherry and WT-untagged human glia, the latter were identified by the expression of human nuclear antigen and the lack of fluorescent reporter expression. To immunolabel, sections were rehydrated with PBS, then permeabilized and blocked using a permeabilization/blocking buffer (PBS+0.1% Triton-X (Sigma-Aldrich cat. no. T8787)+10% Normal Goat Serum (ThermoFisher, cat. no. 16210072)) for 2 h. Sections were then incubated overnight with primary antibodies targeting phenotypic makers at 4° C. The following day, the primary antibodies were thoroughly rinsed from the sections with PBS and secondary antibodies were applied to the sections for 1 h. After thoroughly rinsing out the secondary antibodies with PBS, a second round of primary antibodies, this time against fluorescent reporters, were applied to the sections overnight at 4° C. These were rinsed with PBS the following day and the sections were incubated with secondary antibodies for 1 h. The slides were again thoroughly washed with PBS and mounted with Vectashield Vibrance (Vector Labs, cat. no. H-1800).

Xenotransplant Mapping and 3D Reconstruction

To map human cell distribution within the murine striatum, whole brain montages of 15 equidistantly spaced 160 μm apart sagittal sections spanning the entire striatum were captured using a Nikon Ni-E Eclipse microscope equipped with a DS-Fil camera at 10× magnification and processed in the NIS-Elements imaging software (Nikon). The striatum within each section was outlined and immunolabeled human cells were identified and mapped within the outlined striatum using the StereoInvestigator software (MicroBrightField Bioscience). When applicable, the injection site for WT glia was mapped as a reference point for further volumetric quantification of human cell distribution. Mapped sections were then aligned using the lateral ventricle as a reference to produce a 3D reconstructed model of the humanized murine striatum.

After 3D reconstruction, the cartesian coordinates for each human cell marker, injection site and striatal outlines were exported for further analysis.

To assess the distribution and proportion of proliferative cells in each human cell population within the striatum, immunolabeled human cells expressing Ki67 were mapped in every third section of the 15 sections when performing the 3D reconstructions.

Volumetric Quantification

To quantify the spatial distribution of HD glia in HD chimeras, the volumes for each quantified striatal section were calculated by multiplying the section thickness (20 μm) by the section area. The cell density for each section was then calculated by dividing the number of marked cells in each section by their respective volume.

To quantify the spatial-temporal dynamics of competing WT and HD glia, a program was developed to calculate the volumetric distribution of each cell population as a function of distance to the WT glia delivery site in 3D reconstructed datasets (FIG. 4). To that end, each quantified section was given an upper and lower boundary $z_u$, $z_l$, by representing the striatal outline as two identical polygons separated from each other by the section thickness (20 μm). Then, since the depth-wise location of each cell marker within each individual section is unknown, marked cells within each section were represented as uniform point probability functions with constant probability across the section. I.e., each cell marker in a section from $zz_{ll}$ to $zz_{uu}$ has a probability function:

$$P(z) = \begin{cases} \dfrac{1}{z_u - z_l}, & z_l \leq z < z_u \\ 0, & \text{otherwise} \end{cases}.$$

The spatial distribution of each cell population was then measured by counting the number of marked cells within concentric spherical shells radiating from the WT glia delivery site in radial increments of 125 μm (For control HD chimeras, an average of the coordinates of the WT glia delivery site was used). Marked cells were counted if their respective representative line segments are fully inside, fully outside or intersecting the spherical shell at either the upper or lower boundary. The density of each cell population $\rho_{a,b}$—where a,b represents the minimum and maximum radii of the spherical shell—was then calculated by dividing number of marked cells within the spherical shell by the combined section volume within the shell:

$$\rho_{a,b} = N_{a,b} / V_{a,b}$$

where $N_{a,b}$ is the sum of integrated point probability functions over each section for each point and $V_{a,b}$ is the combined section volume within the spherical shell. Subsequent analyses were restricted to a 2 mm spherical radius. The code was implemented in Python 3.8 and the package Shapely 1.7 to represent polygons and calculate circle intersections of the polygons.

Stereological Estimations and Phenotyping

Estimations of the total amount of human cells and their respective phenotyping were performed stereologically using the optical fractionator method (Shin, J.-Y. et al. "Expression Of Mutant Huntingtin In Glial Cells Contributes To Neuronal Excitotoxicity" J Cell Biology 171, 1001-1012 (2005), which is hereby incorporated by reference in its entirety) in 5 equidistantly separated 480 μm apart sections spanning the entire striatum. First, whole striatum z-stacked montages were captured using a Nikon Ni-E Eclipse microscope equipped with a DS-Fil camera at 20× magnification and processed in the NIS-Elements imaging software (Nikon). Each z-stack tile was captured using a 0.9 μm step size. The montages were then loaded onto Stereo-Investigator and outlines of the striatum were defined. A set of 200×200 μm counting frames was placed by the software in a systematic random fashion within a 400×400 μm grid covering the outlined striatum of each section. Counting was performed in the entire section height (without guard zones) and cells were counted based on their immunolabelling in the optical section in which they first came into focus.

Statistical Analysis and Reproducibility

Samples exhibiting artifacts related to technical issues from experimental procedures—such as mistargeted injections, overt surgical damage, or injections into gliotic foci were excluded from this study. Statistical tests were performed using GraphPad Prism 9. For comparisons between more than two groups, one-way analysis of variance (Tukey's multiple comparison test) was applied. For comparisons between two groups with more than two factors, two-way analysis of variance (Sidak's multiple comparison test) was applied. When comparing between two matched groups, paired two-tailed t-tests were applied for normally distributed data sets, while for unmatched groups, unpaired two-tailed t-tests were applied. Significance was defined as $P<0.05$. Respective P values were stated in the figures whenever possible, otherwise, **$P<0.0001$, *$P<0.001$, **$P<0.01$, *$P<0.05$. The number of replicates is indicated in the figure legends, with n denoting the number of independent experiments. Data are represented as the mean±standard error of mean (s.e.m).

Figure 2:
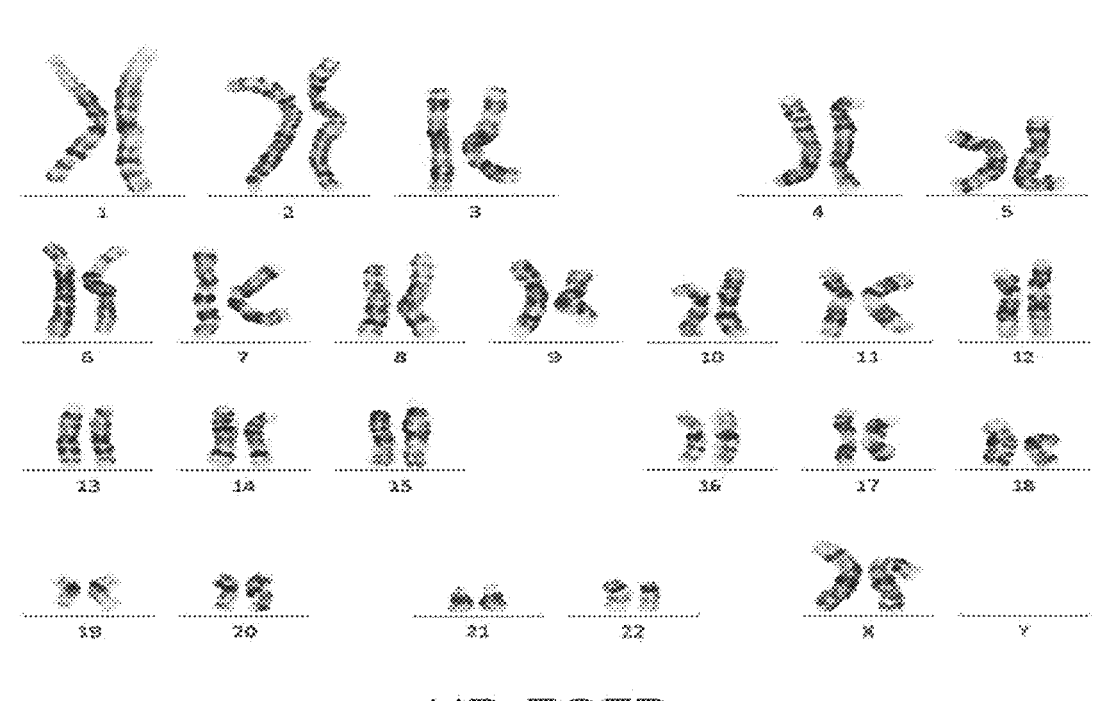
FIG. 2, Panel A shows representative karyotypes from WT-mCherry and HD-EGFP to assess acquired copy number variants (CNVs) and loss-of-heterozygosity regions (LOH). Panels B-C show karyotype analysis.
Figure 2:
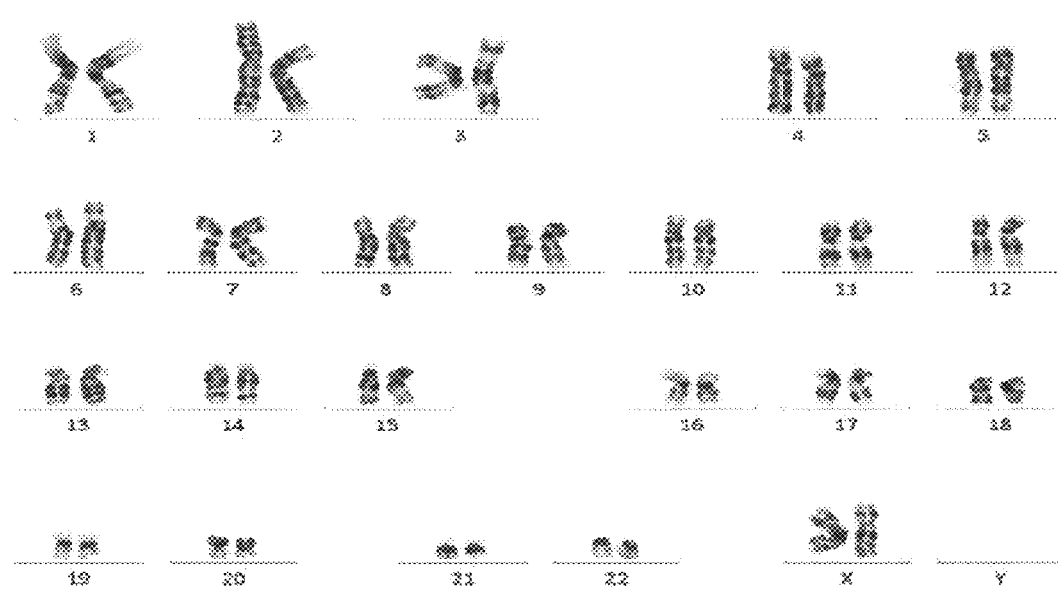

Example 2: Generation of Distinctly Color-Tagged Human Glia from WT and HD hESCs To assess the ability of healthy glia to replace their diseased counterparts in vivo, fluorophore-tagged reporter lines of WT and HD human embryonic stem cells (hESC) were first generated, so as to enable the production of spectrally-distinct GPCs of each genotype, whose growth in vivo could then be independently monitored. A CRISPR-Cas9-mediated knock-in strategy was first used to integrate EGFP and mCherry reporter cassettes into the AAVS1 locus of matched, female sibling wild-type (WT, GENEA019) and mHTT-expressing (HD, GENEA020) hESCs (FIG. 1, Panel A). The reporter cassettes were verified as stably integrated into each of these clones (FIG. 1, Panel D), and that editing did not influence the self-renewal, pluripotency, or karyotypic stability of the tagged hESCs (FIG. 1, Panel E and FIG. 2 Panel A). From these tagged and spectrally-distinct lines, a differentiation protocol was used (Benraiss, A. et al. Human glia can both induce and rescue aspects of disease phenotype in Huntington disease. Nature Communications 7, 11758 (2016)) to produce color-coded human glial progenitor cells (hGPCs) from each line, whose behaviors in vivo could be compared, both alone and in competition. The ability of each line to maintain EGFP or mCherry expression after maturation as astrocytes or oligodendrocytes was validated, and their lack of any significant differentially-expressed oncogenic mutations, or copy number variants (CNVs) that could bias growth (FIG. 2, Panel B-Panel C); it was also verified that both the WT and mHTT-expressing hGPCs, when injected alone, colonized the murine host brains (FIG. 15, Panel A-B, FIG. 5, and FIG. 6, Panel A).

Figure 3:
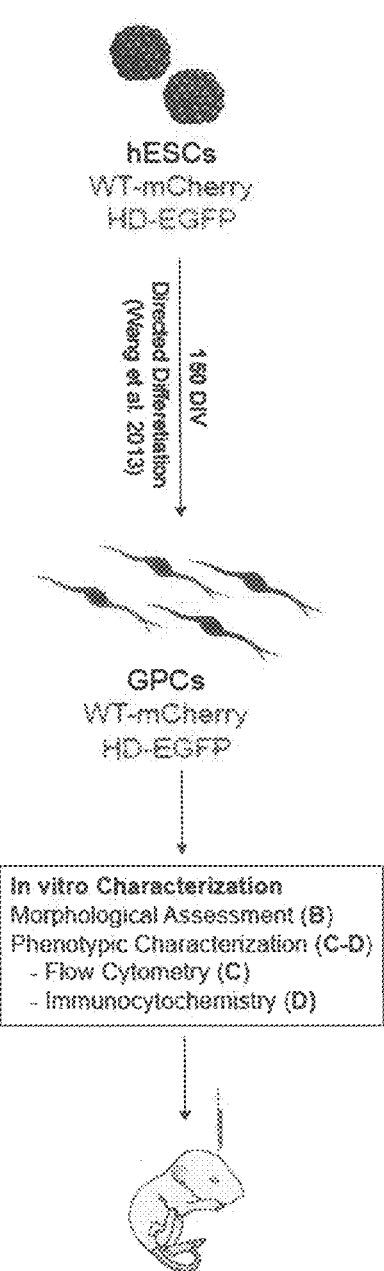
FIG. 3, Panel A illustrates creation of HD-chimeric mice. Panels B-D show representative images and characterization of cells in HD-chimeric mice.
Figure 3:
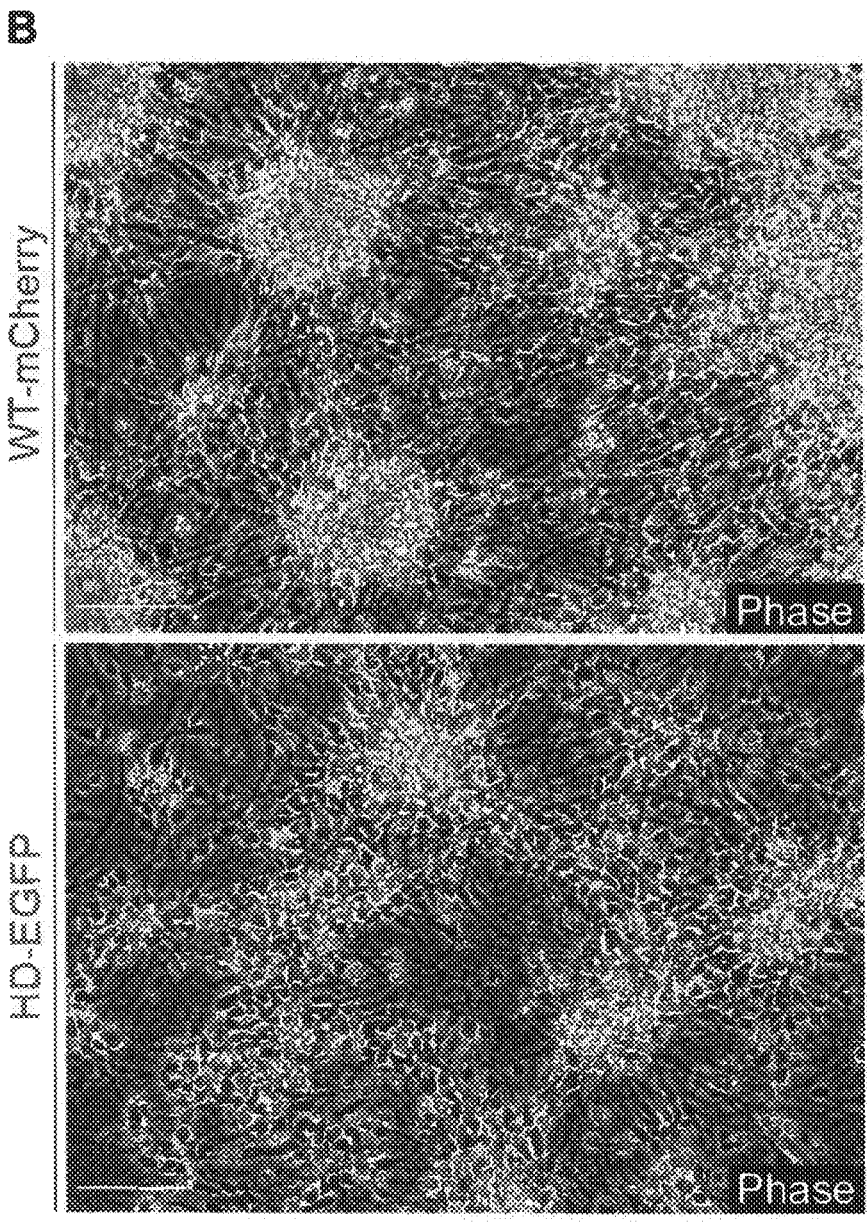
Figure 3:
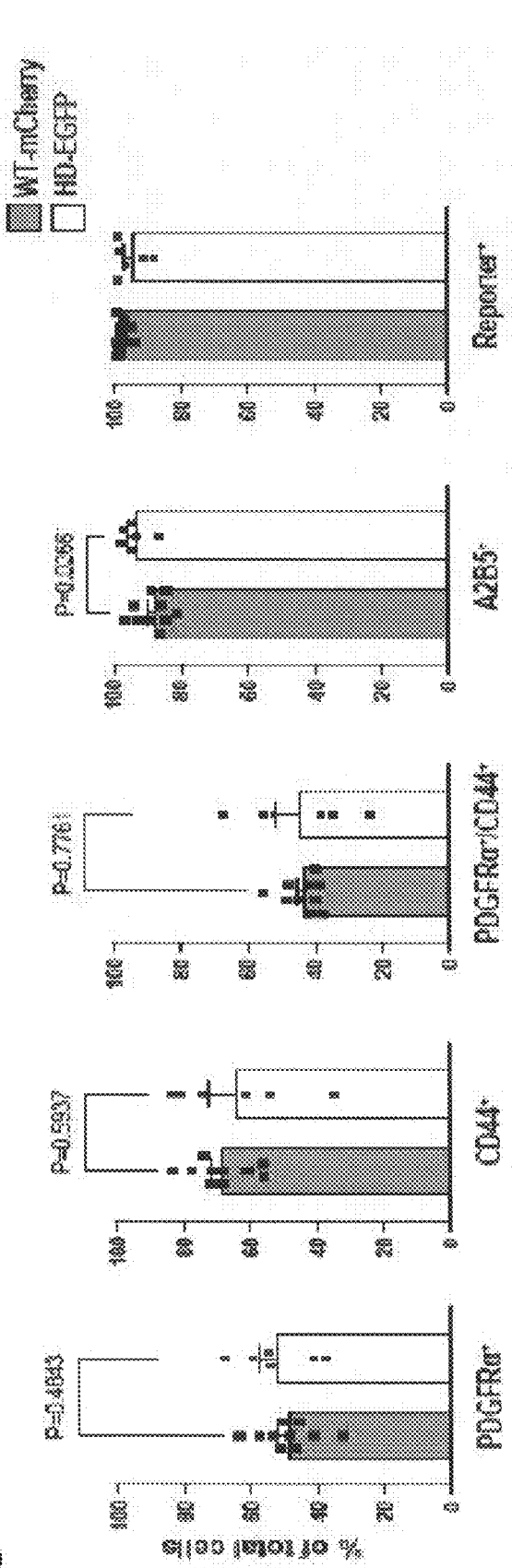
Figure 18:
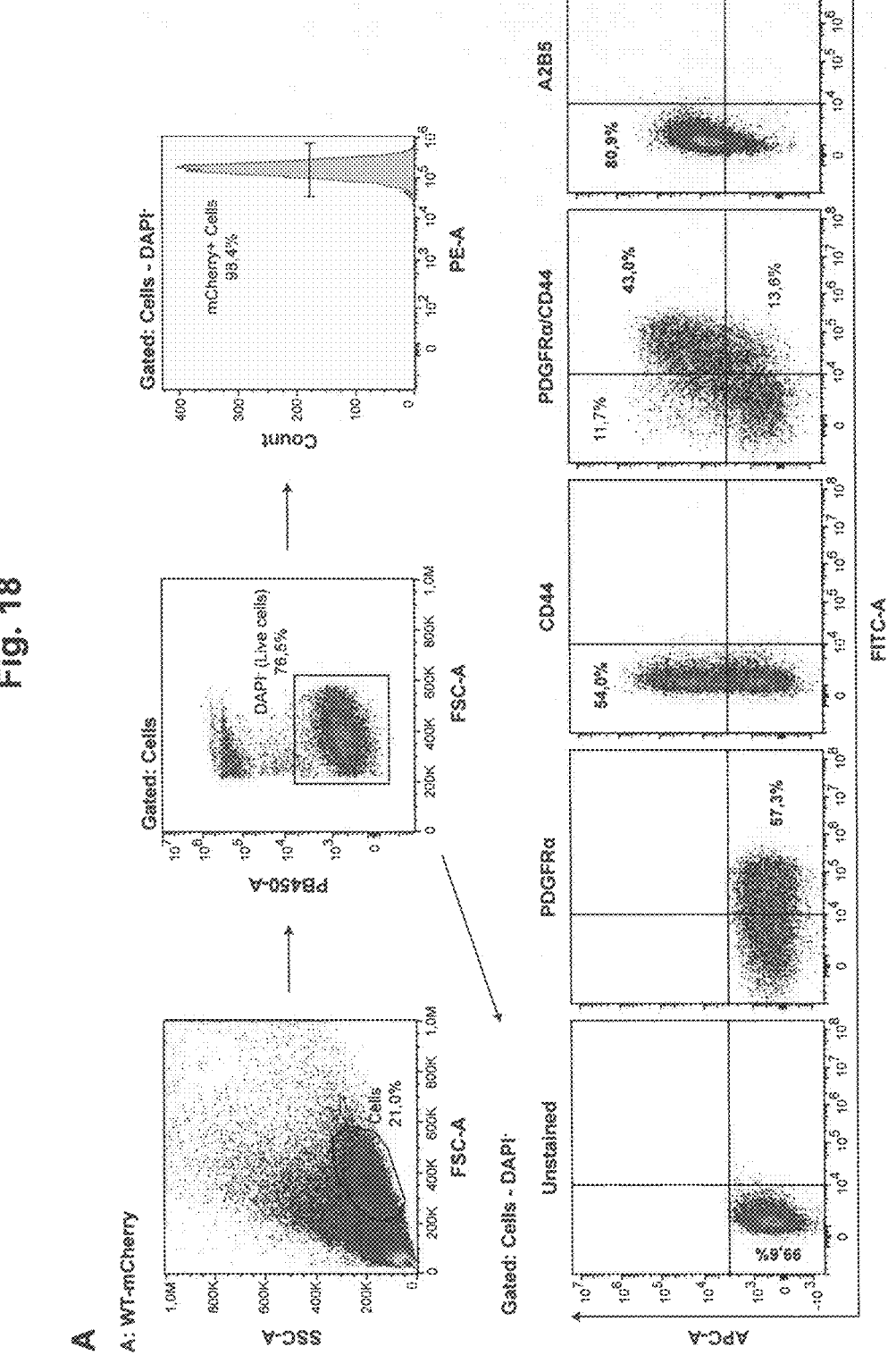
FIG. 18, Panels A-B show gating strategy flow cytometry analysis.
Figure 18:
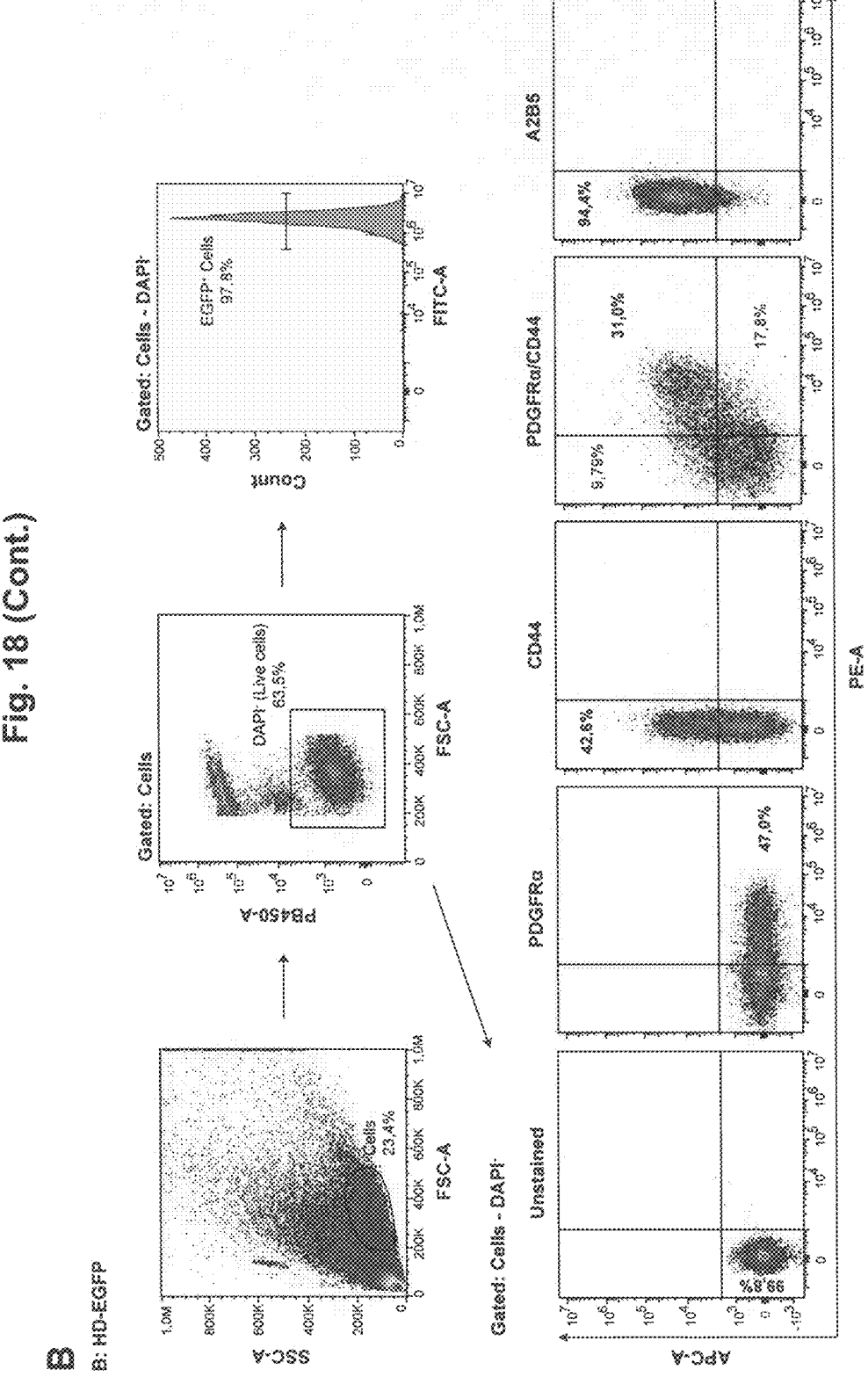

Both WT-mCherry and HD-EGFP hESCs were differentiated using a protocol for generating hGPCs (Wang, S. et al. Human iPSC-Derived Oligodendrocyte Progenitor Cells Can Myelinate and Rescue a Mouse Model of Congenital Hypomyelination. Cell Stem Cell 12, 252-264 (2013)) and both their capacity to differentiate into glia and the stability of their reporter expression upon acquisition of glial fate were assessed (FIG. 3, Panels A-D). By 150 days in vitro (DIV), glial cultures derived from both WT-mCherry and HD-EGFP were equally enriched for PDGFRα+/CD44+ bipotential GPCs (P=0.78), comprising around half of the cells in the cultures, with the rest being immature A2B5+ GPCs 27 and PDGFRα−/CD44+ astrocytes and their progenitors (FIG. 3, Panel C and FIG. 18, Panels A-B). Importantly, virtually all immune-phenotyped cells derived from WT-mCherry and HD-EGFP hESCs-including mature astrocytes as well as GPCs-continued to express their respective fluorescent reporter, indicating that transgene expression remained stable upon acquisition of terminal glial identity (FIG. 3, Panel D).

Example 3: Establishment of Human HD Glial Chimeric Mice

Figure 15:
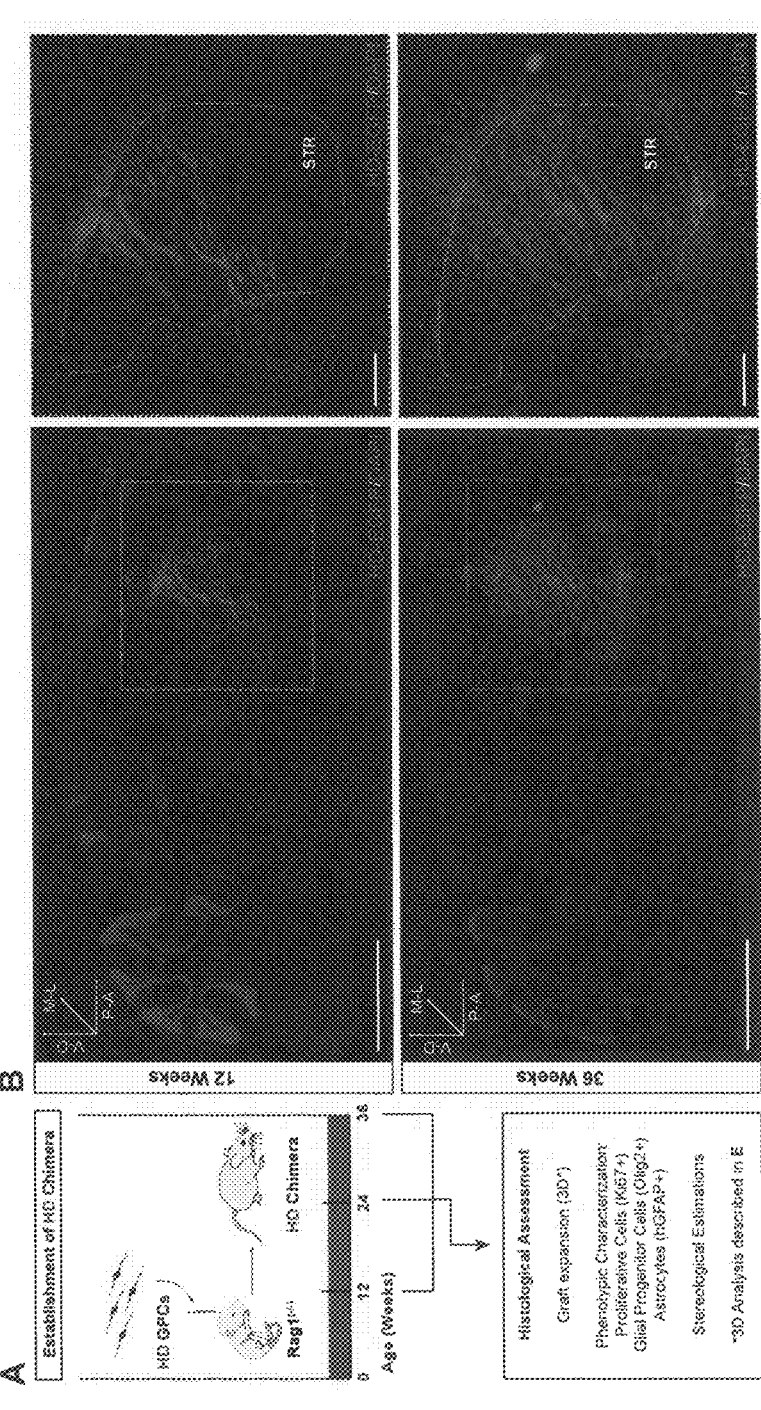
FIG. 15, Panels A-D show murine chimeras with striata substantially humanized by HD glia were generated to provide an in vivo model by which to assess the replacement of diseased human glia by their healthy counterparts. hGPCs derived from mHTT-expressing hESCs engineered to express EGFP were implanted into the neostriatum of immunocompromised Rag1(−/−) mice and their expansion histologically was monitored. Panels E-J show murine chimeras with striata substantially humanized by HD glia were generated to provide an in vivo model by which to assess the replacement of diseased human glia by their healthy counterparts. hGPCs derived from mHTT-expressing hESCs engineered to express EGFP were implanted into the neostriatum of immunocompromised Rag1(−/−) mice and their expansion histologically was monitored.
Figure 15:
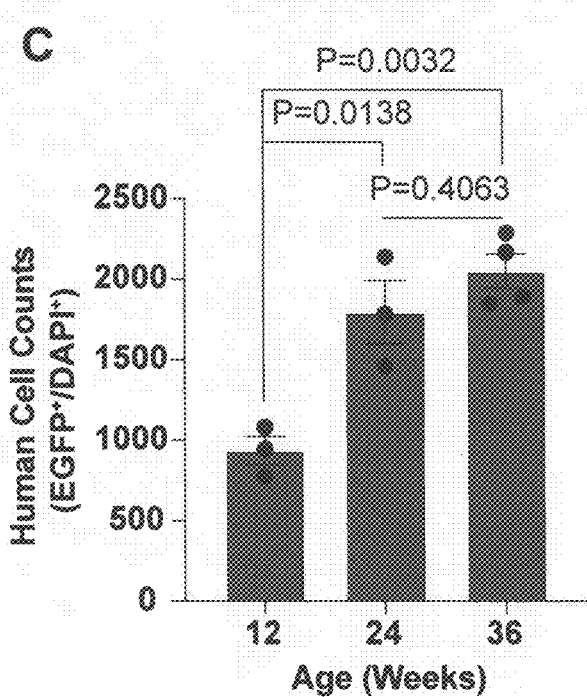
Figure 15:
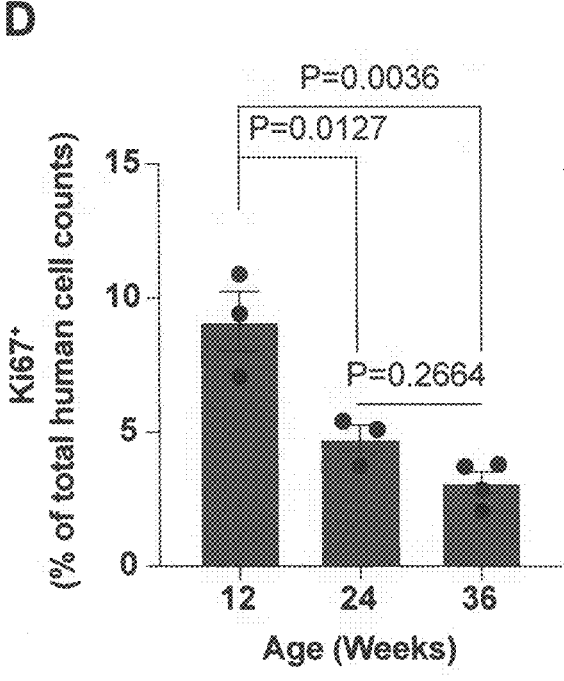
Figure 15:
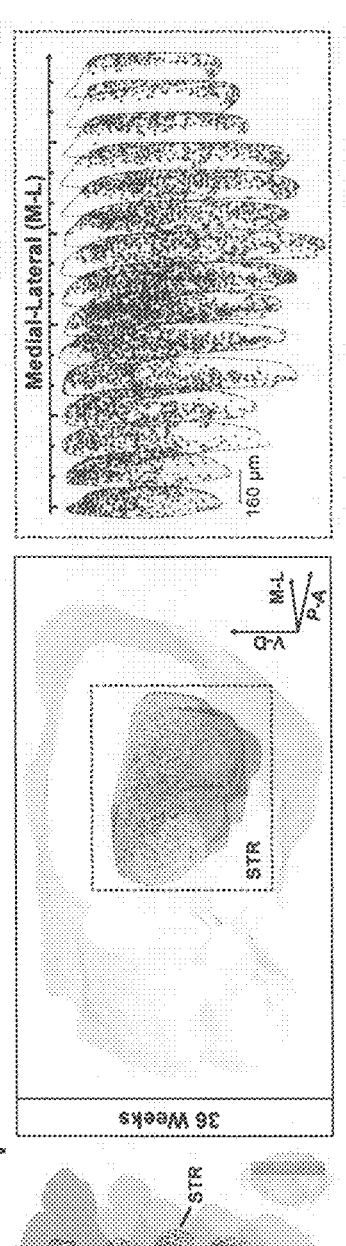
Figure 15:
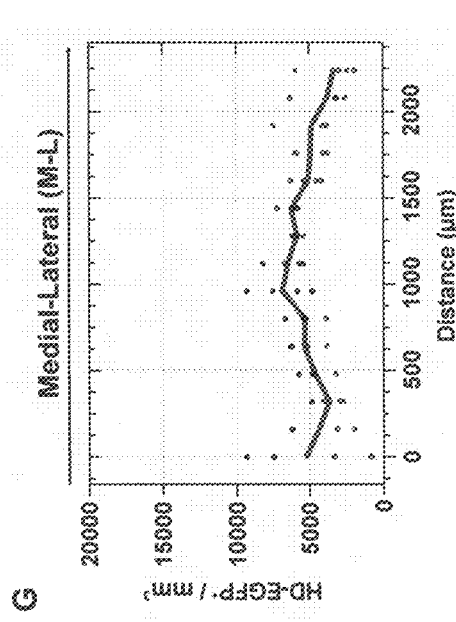
Figure 15:
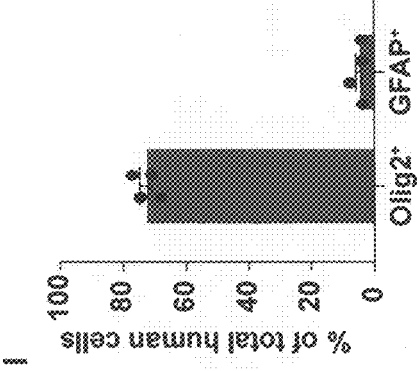
Figure 15:
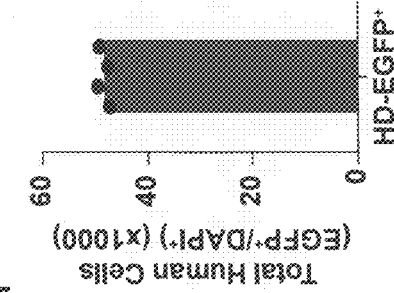
Figure 15:
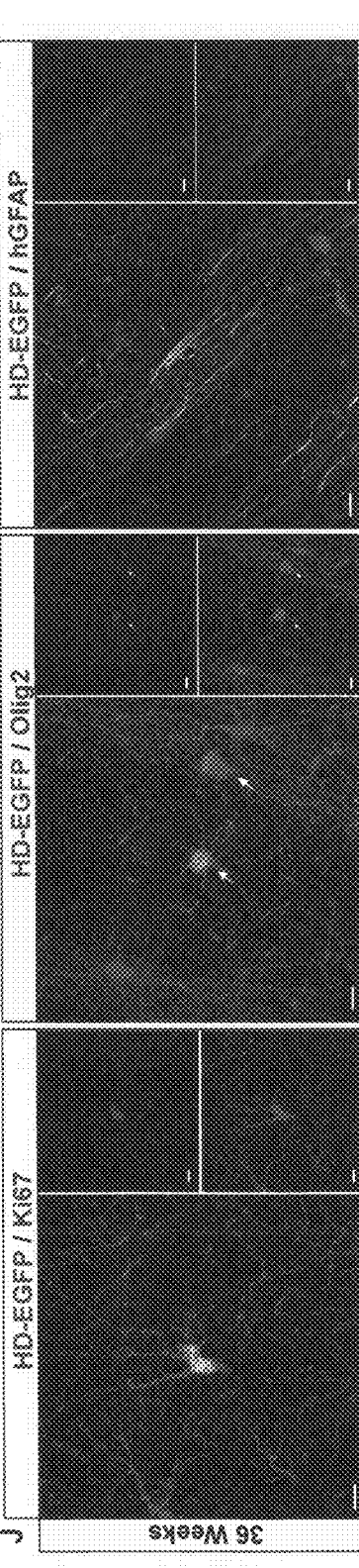
Figure 16:
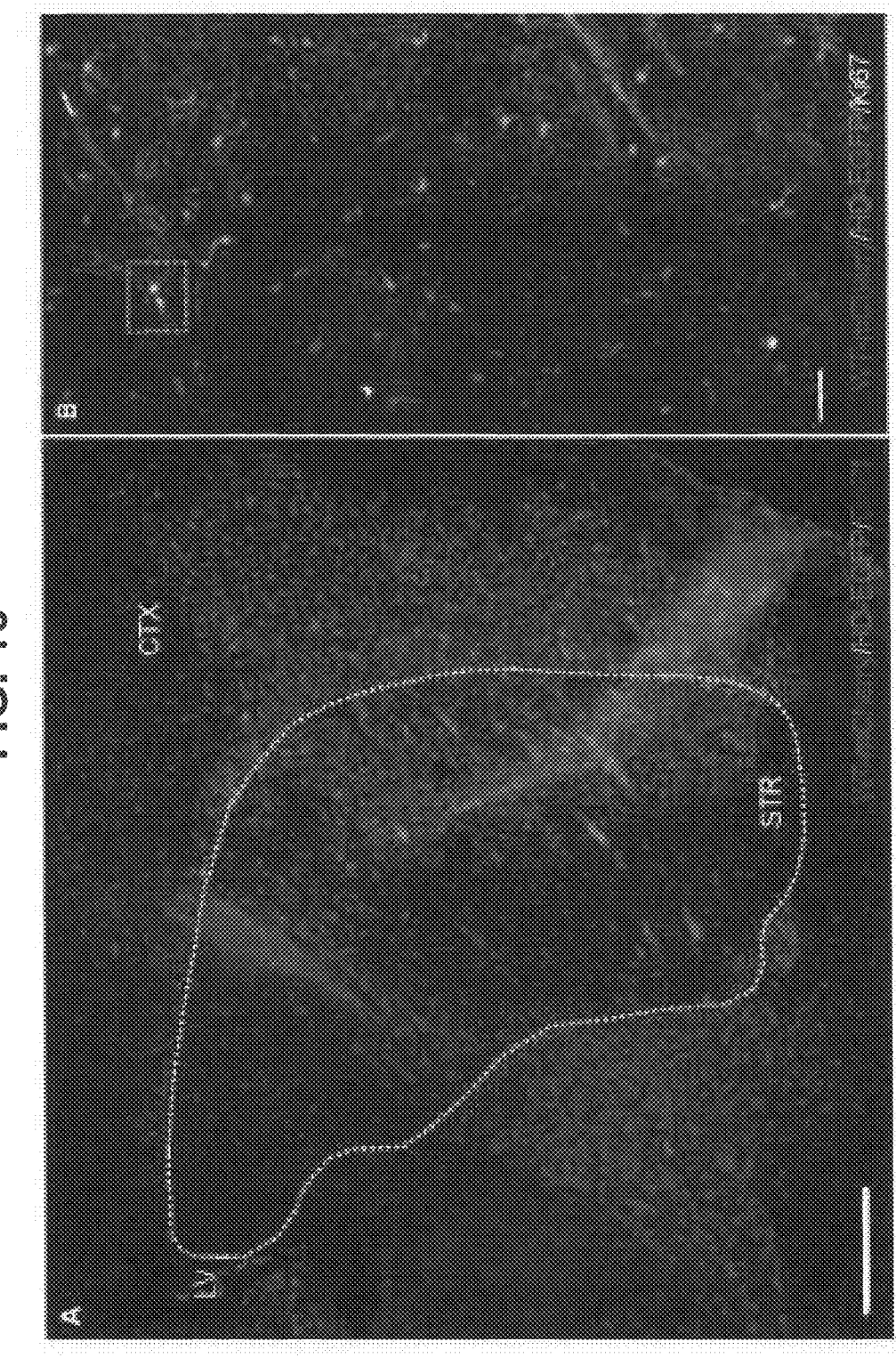
FIG. 16, Panels A-B show proliferative advantage drives WT glia to advance through the humanized HD striatum.

Murine chimeras with striata substantially humanized by HD glia (HD chimeras, FIG. 5) were generated to provide an in vivo model by which to assess the replacement of diseased human glia by their healthy counterparts. hGPCs derived from mHTT-expressing hESCs engineered to express EGFP (FIG. 1 and FIG. 5; henceforth designated as HD) were implanted into the neostriatum of immunocompromised Rag1(−/−) mice and their expansion histologically was monitored (FIG. 15, Panel A).

Following implantation, HD glia rapidly infiltrated the murine striatum, migrating and expanding firstly within the striatal white matter tracts (FIG. 15, Panel B). Gradually, these cells expanded outwards, progressively displacing their murine counterparts from the striatal neuropil, so that by 36 weeks, the murine striatum was substantially humanized by HD glia (FIG. 15, Panel B, 15, Panel F, and 15, Panel G). The advance of HD glia was driven by their mitotic expansion, with their total number doubling between 12 and 36 weeks (FIG. 15, Panel C; P=0.0032). Inversely, as they expanded and matured within their newly established domains, their proliferative cell pool (Ki67+) was progressively depleted (FIG. 15, Panel D, and I; P=0.0036), slowing their expansion rate over time.

Most of the HD glia expanded as Olig2+ GPCs (72.7±1.9%), which persisted as the new resident pool after replacing their murine counterparts. A fraction of these (4.8±0.9%) further differentiated into GFAP+ astrocytes (FIG. 15, Panel I and 15, Panel J). Astrocytic differentiation was mostly observed within striatal white matter tracts. These sick astrocytes lacked the structural complexity typically observed in healthy counterparts and displayed abnormal fiber architecture, as previously reported (FIG. 15, Panel J; Osipovitch, M. et al., "Human ESC-Derived Chimeric Mouse Models of Huntington's Disease Reveal Cell-Intrinsic Defects in Glial Progenitor Cell Differentiation," Cell Stem Cell 24:107-122 (2019), which is hereby incorporated by reference in its entirety).

Figure 5:
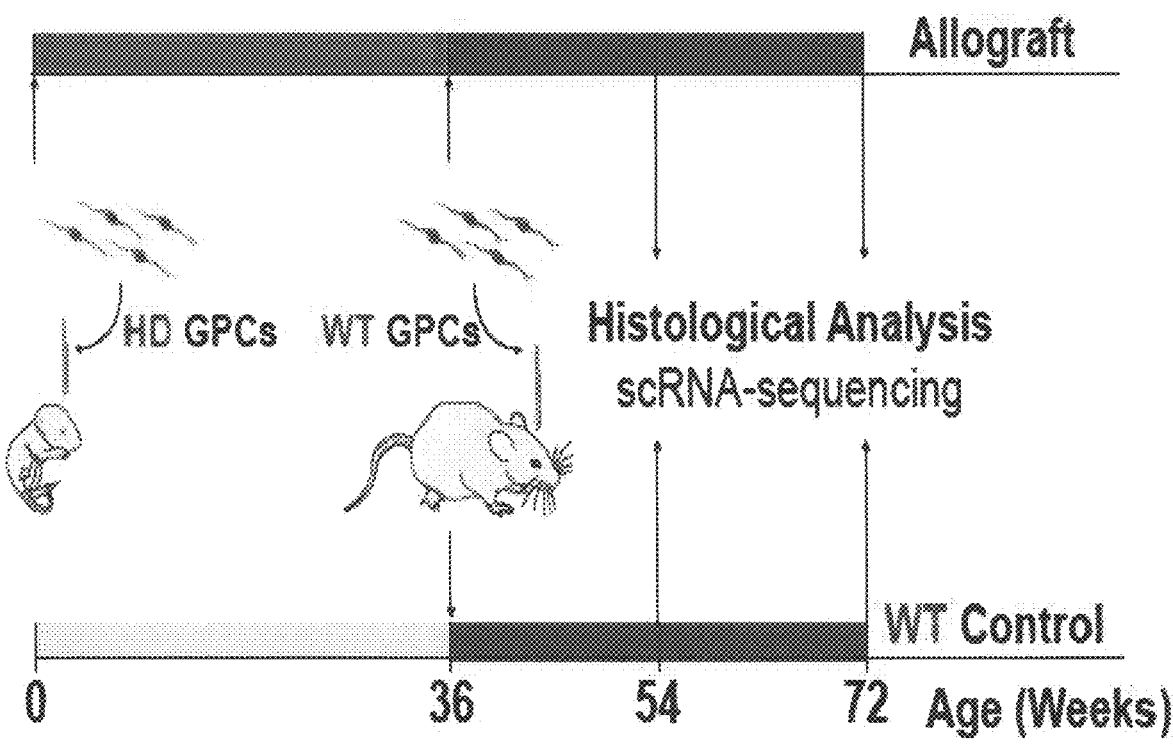
FIG. 5 illustrates the experimental design of the HD vs WT mouse and the HD control mouse.
Figure 6:
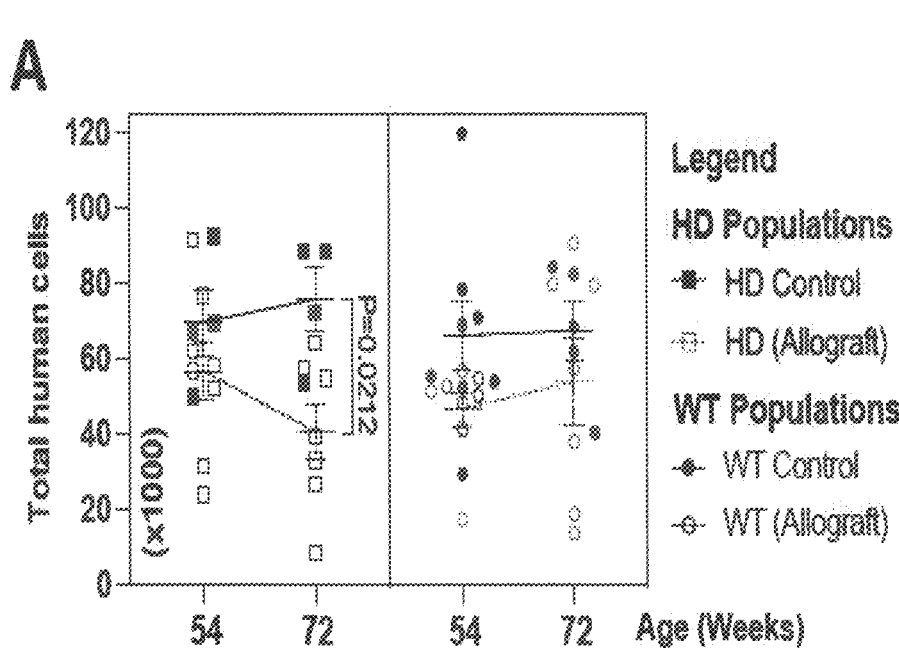
FIG. 6, Panels A-C show human wildtype glia outcompete previously integrated human HD glia. Panel A provides stereological estimations demonstrate that the total number of HD glia progressively decreases relatively to HD chimera controls as WT glia expands within the humanized striatum; Two-way ANOVA with Šidák's multiple comparisons test. Panel B and Panel C show the proportion of GPCs (Olig2+, Panel B) and astrocytes (GFAP+, Panel C) in both populations was maintained as they competed for striatal dominance; HD Control—n=4 for both timepoints; WT Control—n=4 for 54 weeks, n=3 for 72 weeks; HD vs WT—n=5 for 54 weeks, n=3 for 72 weeks; Orange arrows point to co-labelled cells. Data shown as means±s.e.m with individual data points. Panels D-E shows representative images of HD glia (Panel D) and WT glia (Panel E) of WT glia expanded as Olig2+ (white) GPCs displacing their HD counterparts. Within areas where they became dominant, they further differentiated into hGFAP+ (white) astrocytes.
Figure 6:
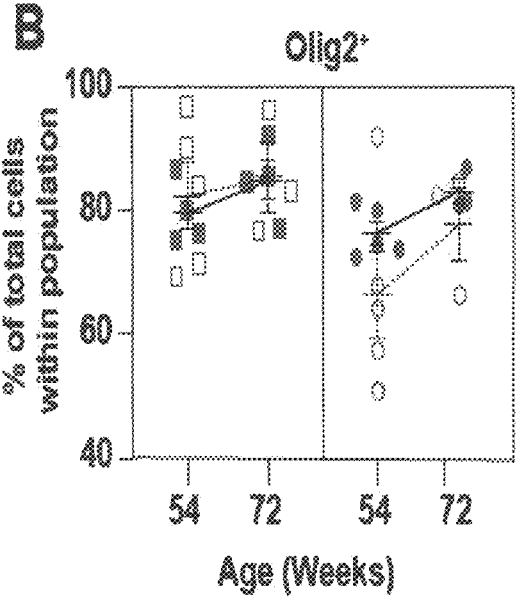
Figure 6:
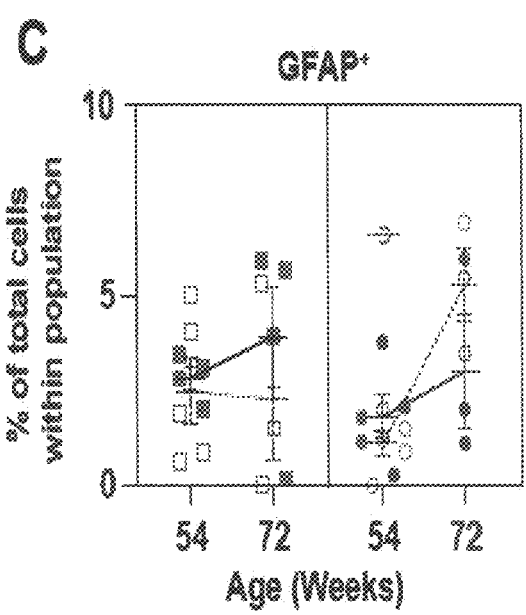
Figure 6:
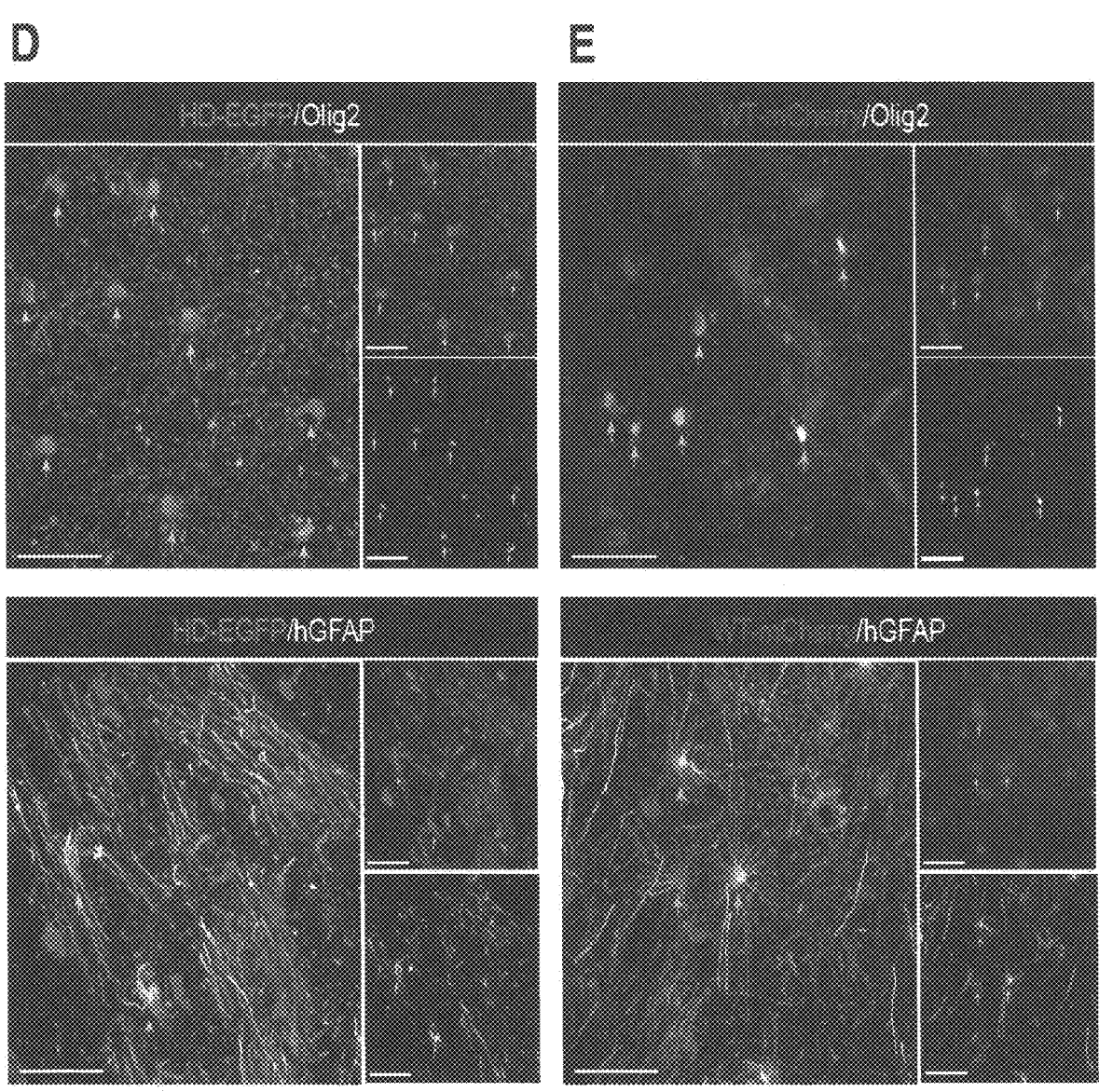

Example 4: Healthy WT hGPCs Infiltrate the HD Chimeric Adult Striatum and Outcompete Resident Glia The established chimeras whose striatal glia are largely mHTT-expressing and human were used to determine how the resident HD human glia might respond to the introduction of healthy hGPCs and whether the resident glial populations might to some extent be replaced. hGPCs derived from WT hESCs engineered to express mCherry (FIG. 1, FIG. 2, and FIG. 3; henceforth designated as WT) were engrafted into the striatum of 36 weeks old HD chimeras and monitored for expansion using histology as they competed for striatal domination (FIG. 5).

Following engraftment, WT glia pervaded the previously humanized striatum, gradually displacing their HD counterparts as they expanded from their implantation site (FIG. 4). This process was slow but sustained, over time yielding substantial repopulation of the HD striatum (FIG. 4; 54 weeks, p<0.0001; 72 weeks, p<0.0001). Remarkably, the expansion of WT glia was paralleled by a concurrent elimination of HD glia from the tissue (as opposed to their spatial relocation) (FIG. 4; 54 weeks-P<0.0001, 72 weeks-P<0.0001), and was typically characterized by a discrete advancing front behind which almost no HD glia could be found (FIG. 4).

Mutually exclusive domains formed in the wake of competition between Olig2+ GPCs (FIG. 4). These comprised most of the WT glial population (80.1±4.7% at 72 weeks), which persisted as the new resident GPC pool after replacing their HD counterparts. Their potential to generate astroglia was maintained, as a fraction of these (4.0±1.5% at 72 weeks) further differentiated into GFAP+ astrocytes (FIG. 6) within their newly established domains. Curiously, within regions dominated by WT glia, HD astrocytes (GFAP+) lingered, primarily within white matter tracts (FIG. 4). Nonetheless, the overall ratio between Olig2+ and GFAP+ glia remained stable throughout the experiment in both populations (FIG. 6) indicating that while GPC replacement precedes astrocytic replacement, proportional phenotypic repopulation is achieved over time.

Figure 7:
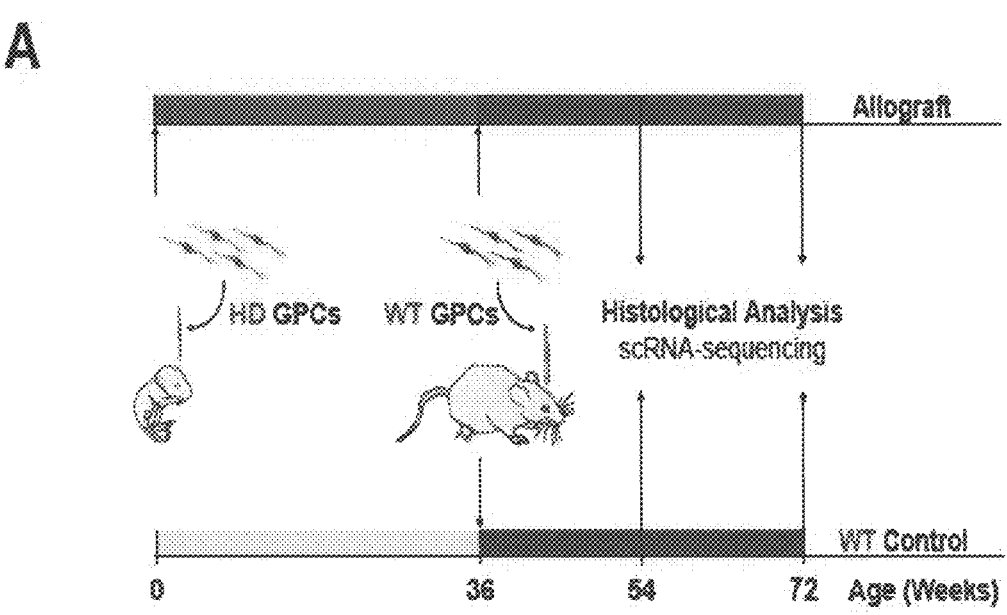
FIG. 7, Panels A-B illustrates the experimental design and analytic timepoints of the WT Control group (Panel A). Panel B shows representative images of engraftment of WT glia (mCherry+, red) into the adult striatum of Rag1 (−/−) mice yields substantial humanization of the murine striatum over time. Panels C-D show volumetric quantifications show that WT glia infiltrate and disperse throughout the murine striatum over time, and they do so more broadly than those grafted onto HD chimeras; WT (HD vs WT Group)—n=8 for 54 weeks, n=7 for 72 weeks vs WT Control—n=7 for 54 weeks, n=5 for 72 weeks; Two-way ANOVA with Šidák's multiple comparisons test; Main effects are shown as numerical P values; Data is presented as means±s.e.m.
Figure 7:
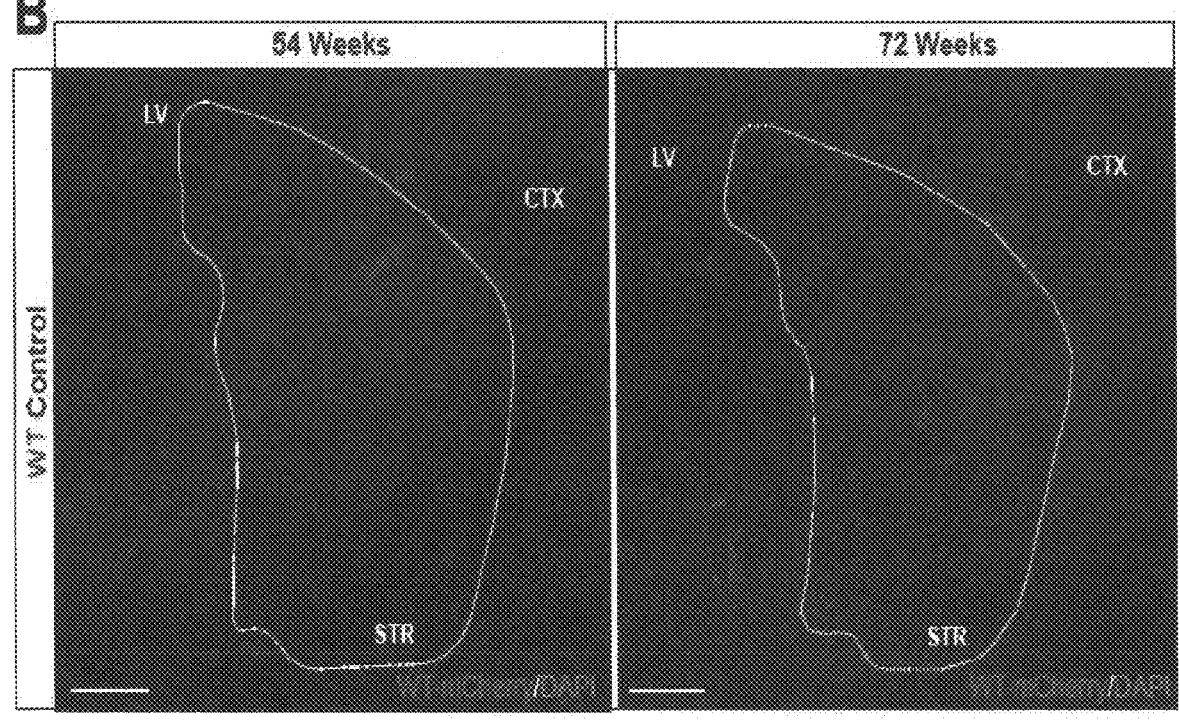
Figure 7:
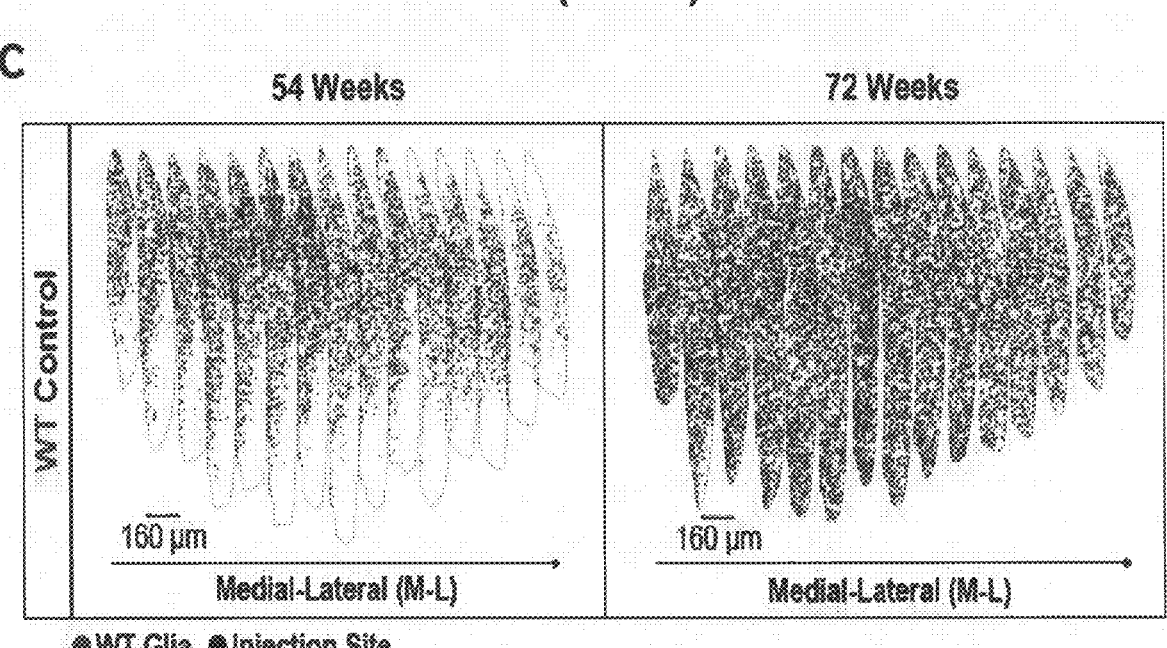
Figure 7:
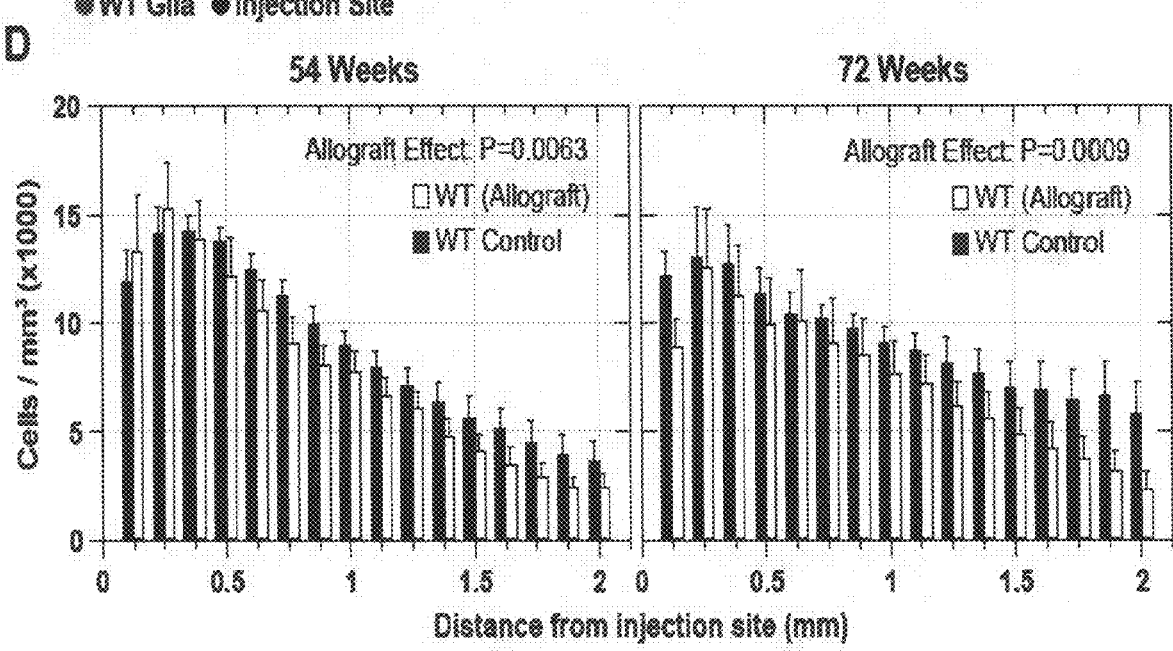

Interestingly, human-human glial replacement developed at a slower rate than human-murine glial replacement, as WT hGPCs implanted into naïve adult Rag1(−/−) mice expanded throughout the host striatum more broadly than those grafted into neonatally-chimerized adult Rag1(−/−) mice (FIG. 7; 54 weeks: P=0.14, 72 weeks: P=0.0009). These results indicate that competitive glial replacement develops with species-specific kinetics that differ between xenogeneic and allogeneic grafts.

Figure 8:
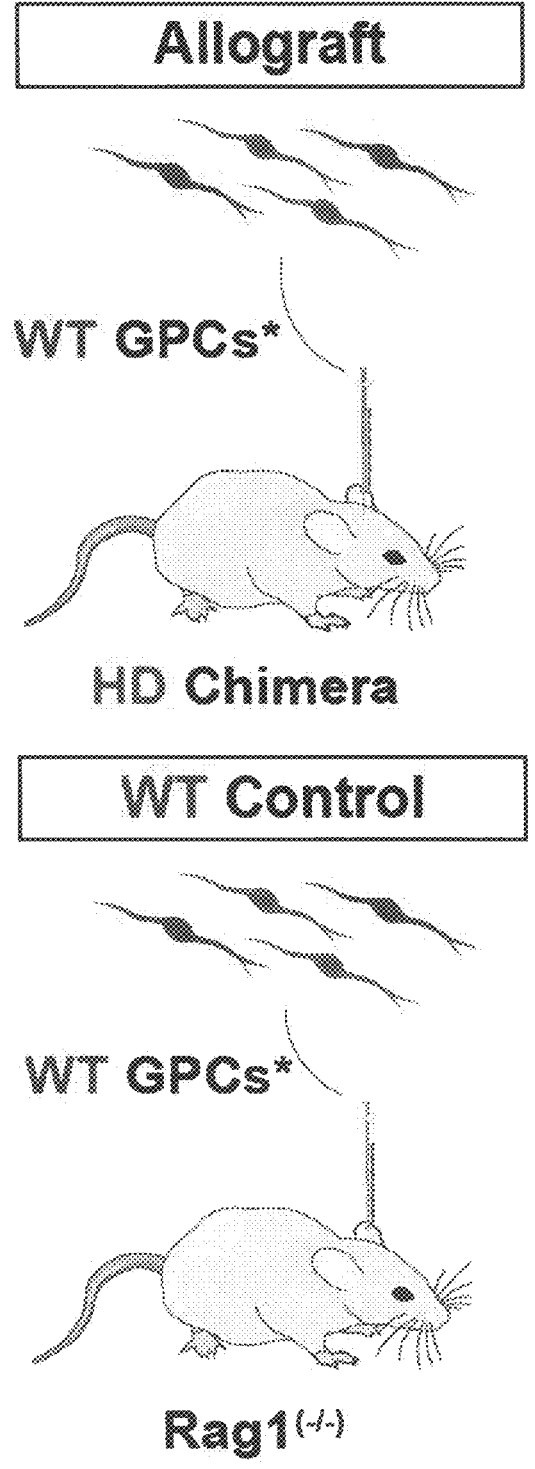
FIG. 8 illustrates the experimental design for mice that received a 1:1 mixture of mCherry-tagged (WT-mCherry) and untagged (WT-untagged) WT glia.
Figure 9:
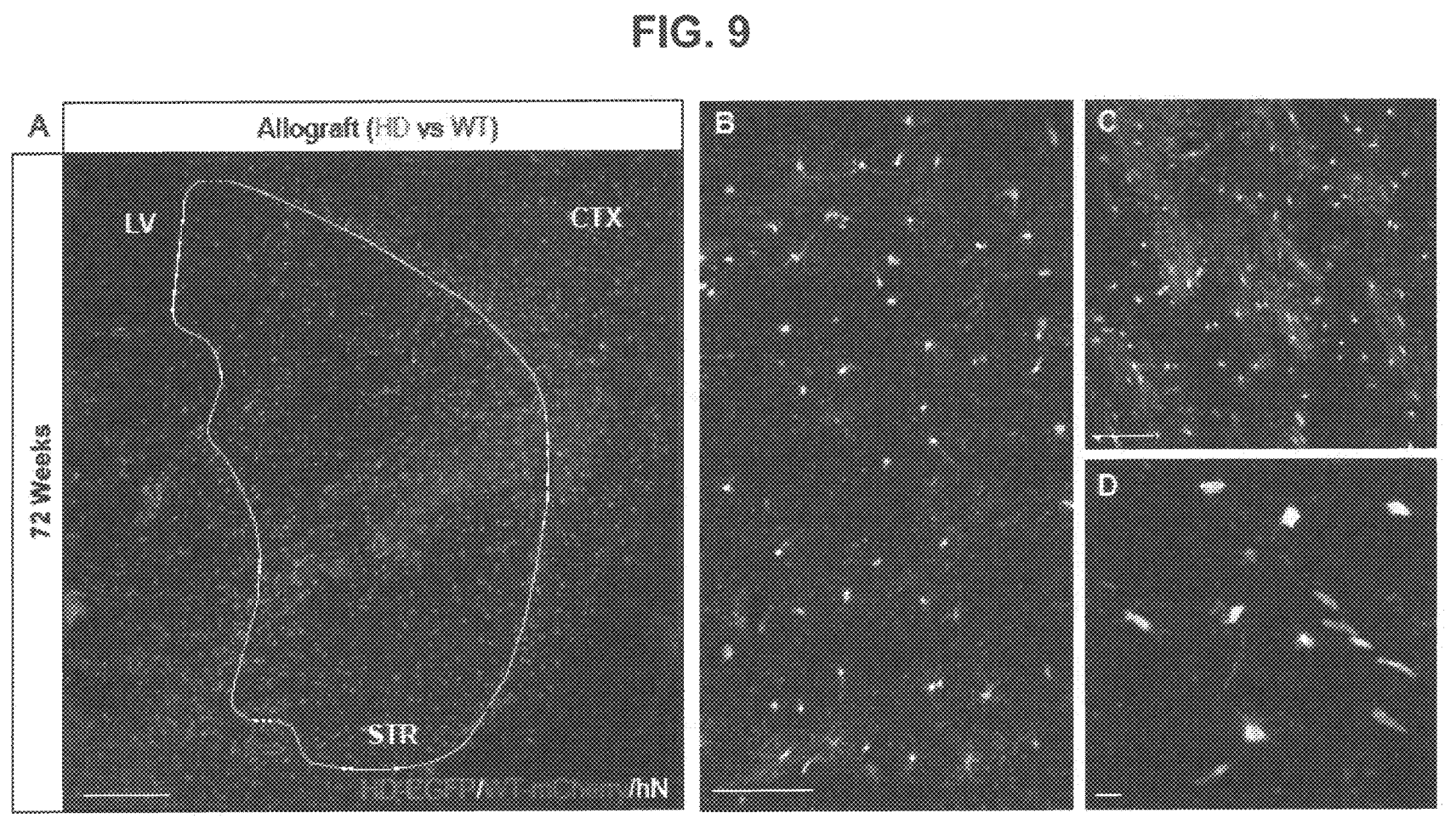
Figure 10:
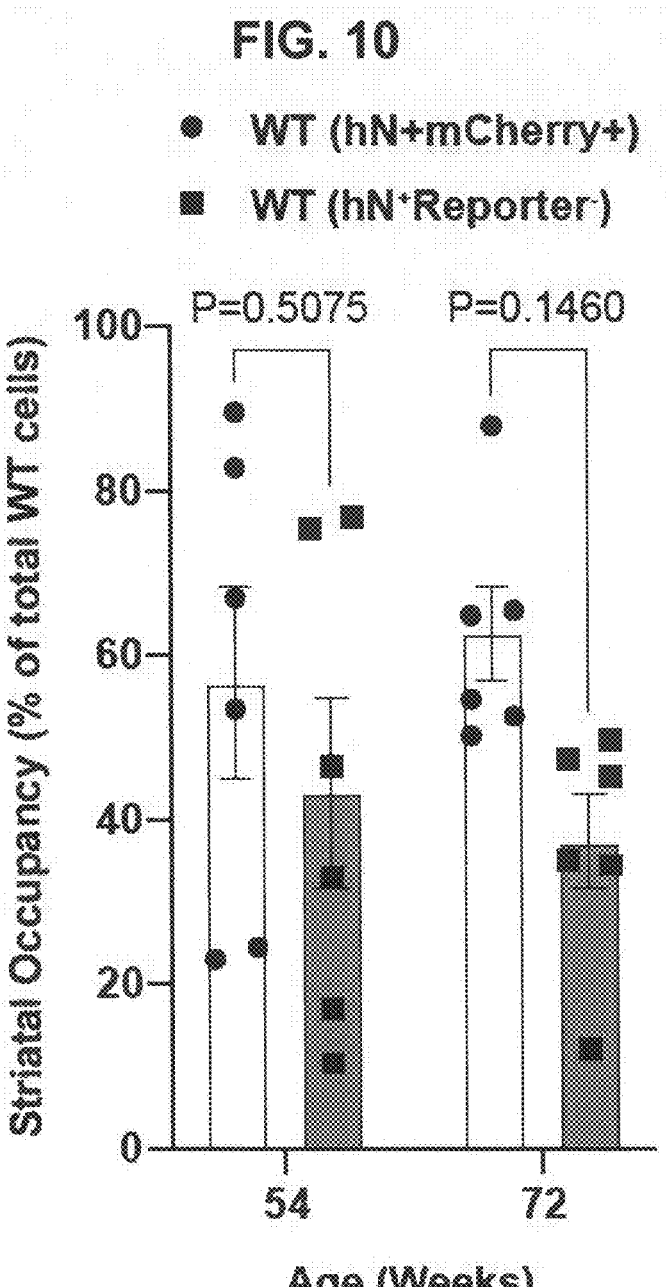
FIG. 10 shows quantification of the proportion of WT-mCherry and WT-untagged glia within the striatum showed no significant difference between the two populations at either quantified timepoint (n=6 for each timepoint); Two-way ANOVA with Šidák's multiple comparisons test; means±s.e.m.
Figure 12:
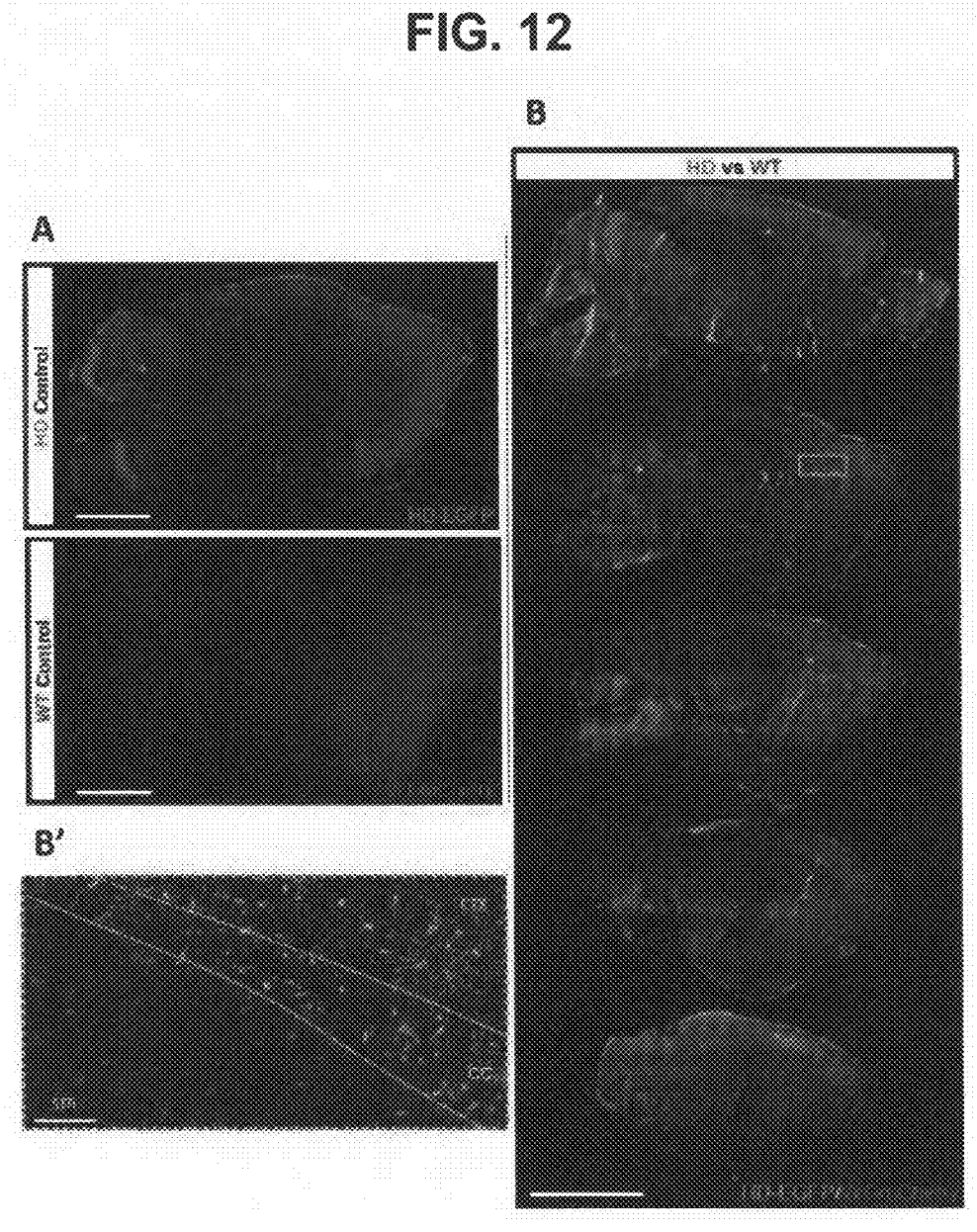
FIG. 12, Panels A-C show representative images of the proportion of WT and HD glia within the striatum in mice co-engrafted with WT and HT glia. The images show no significant growth advantage to either cell population; n=5; two-tailed paired t-test.
Figure 12:
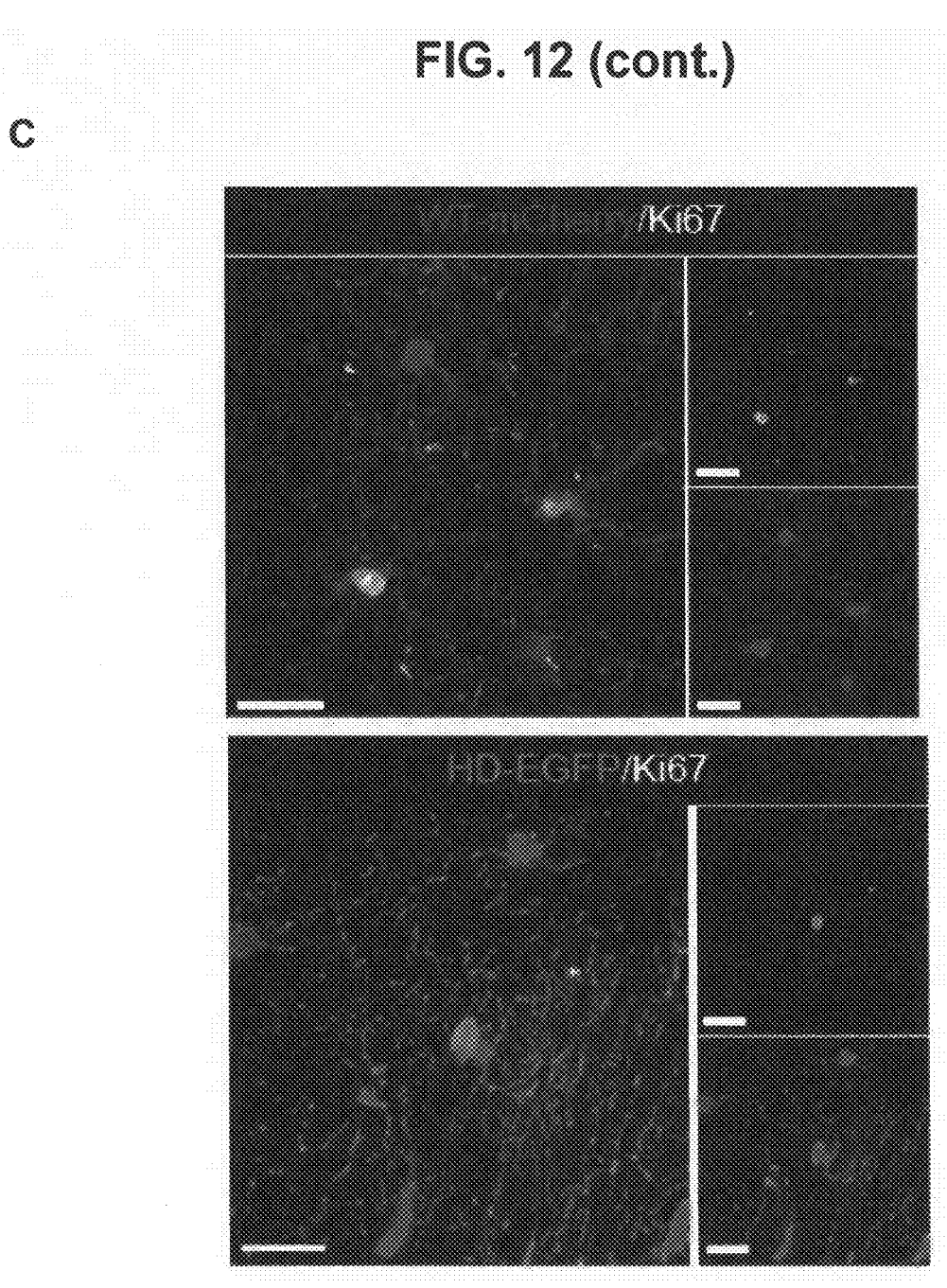

These results were not an artifact of off-target effects derived from gene editing nor fluorescent reporter expression toxicity, as co-engrafted hGPCs derived from WT-mCherry and their unmodified counterparts (WT-untagged) (FIG. 8), expanded equally within the striatum of HD chimeras and yielded analogous glial repopulation (FIG. 9 and FIG. 10; 54 Weeks-P=0.5075-72 Weeks-P=0.1460). As such, analysis done in (FIG. 4) and (FIG. 6 and FIG. 7) reports samples from both experimental paradigms. Remarkably, while WT and HD glia strongly segregated from each other, the two isogenic clones of WT glia could be found admixing (FIG. 9), indicating that active recognition precedes competitive elimination of HD glia from the tissue.

Example 5: Human WT Glia Enjoy a Proliferative Advantage Relative to Resident HD Glia Striatal humanization by HD glia progressed with a gradual exhaustion of their proliferative cell pool as they expanded and matured within the tissue. Therefore, whether the selective expansion of younger WT glia within the HD striatum was sustained by a difference in proliferative capacity between the two populations was tested. The temporal expression of Ki67 in both WT and HD glial populations was assessed as competitive striatal repopulation unfolded.

At both 54 and 72 weeks of age, the mitotic fraction of implanted WT glia was significantly larger than that of resident HD glia (FIG. 4, Panels I and J, 54 weeks—P<0.0001, 72 weeks—P=0.009). These data indicate that the repopulation of the HD striatum by WT glia was fueled by a relatively enriched proliferative cell pool. It's important to note that while this proliferative advantage became less pronounced as the cells aged, it was maintained throughout the experiment. With this in mind, the sustained proliferative advantage of implanted WT glia over their HD counterparts, should provide a driving force for continuous striatal repopulation beyond the observed experimental timepoints.

Figure 19:
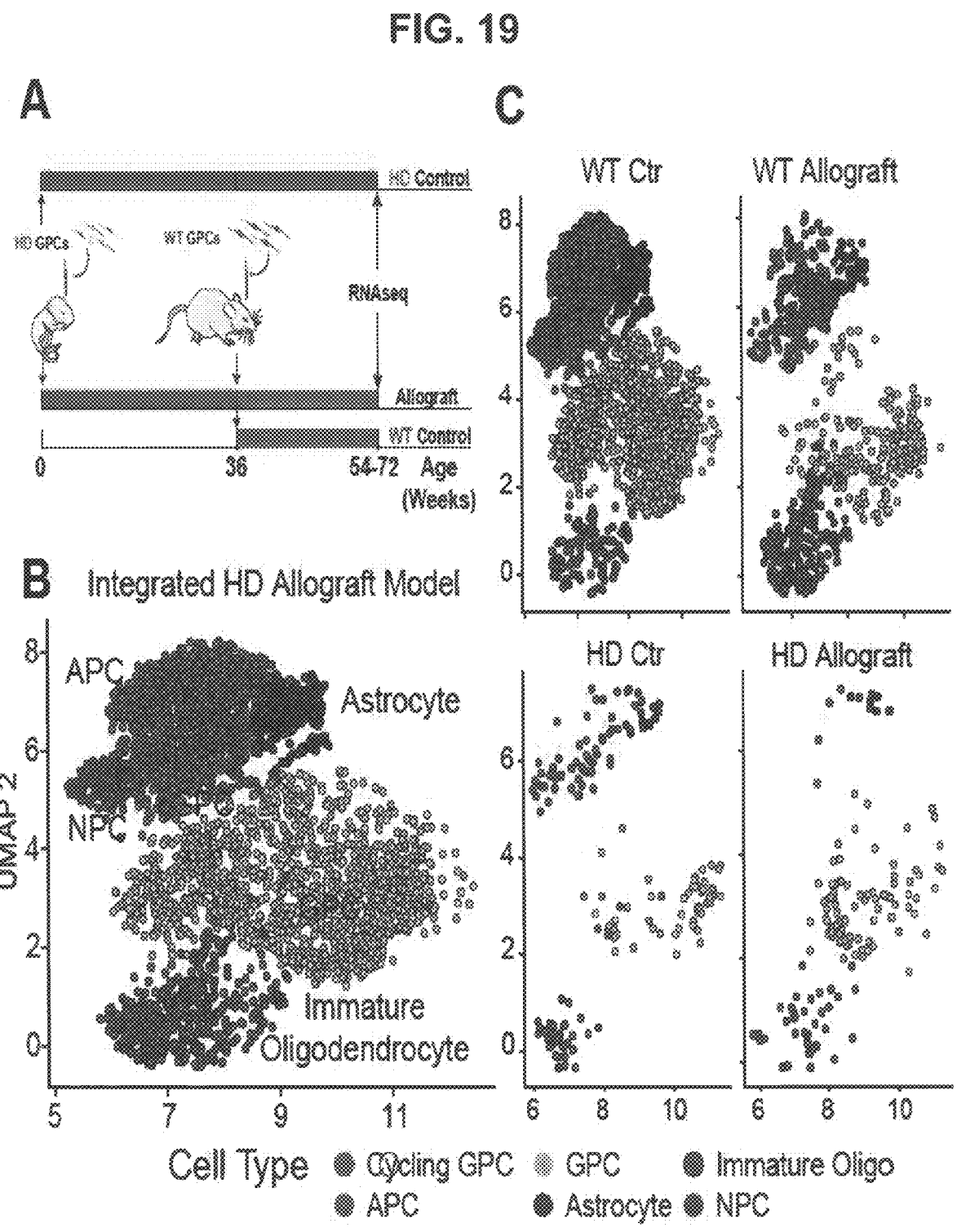
FIG. 19 shows WT glia acquire a dominant competitor transcriptional profile in the face of resident HD glia. Panel A. Experimental design. Panels B and C. Uniform manifold approximation projection (UMAP) visualization of the integrated (B) and split by group (C) scRNA-seq data identifies six major cell populations. Panel D. Stacked bar plot proportions of cell types in each group. Panel E. Cell cycle analysis notched box plots of cycling GPCs and GPCs in the G2/M phase. The box indicates the interquartile range, the notch indicates the 95% confidence interval with the median at the center of the notch, and the error bars represent the minimum and maximum non-outlier values. Panel F. Venn diagram of pairwise differentially expressed GPC genes (Log 2 fold change>0.15, adjusted p-value<0.05). Panel G. Curated ingenuity pathway analysis of genes differentially expressed between GPC groups. The size of circles represents p-value while the shading indicates activation Z-Score with red being more active in the upper group and green being more active in the lower group. Panel H. Heatmap of curated pairwise differentially expressed GPC genes. Panel I. Violin plots of pairwise differentially expressed GPC ribosomal gene log 2 fold changes. Comparisons between groups in E) utilized Dunn tests following a Kruskal-Wallis test with multiple comparisons adjusted via the Benjamini-Hochberg method. *=<0.05, <0.01, *=<0.001, ****=<0.0001 adjusted p-value.
Figure 19:
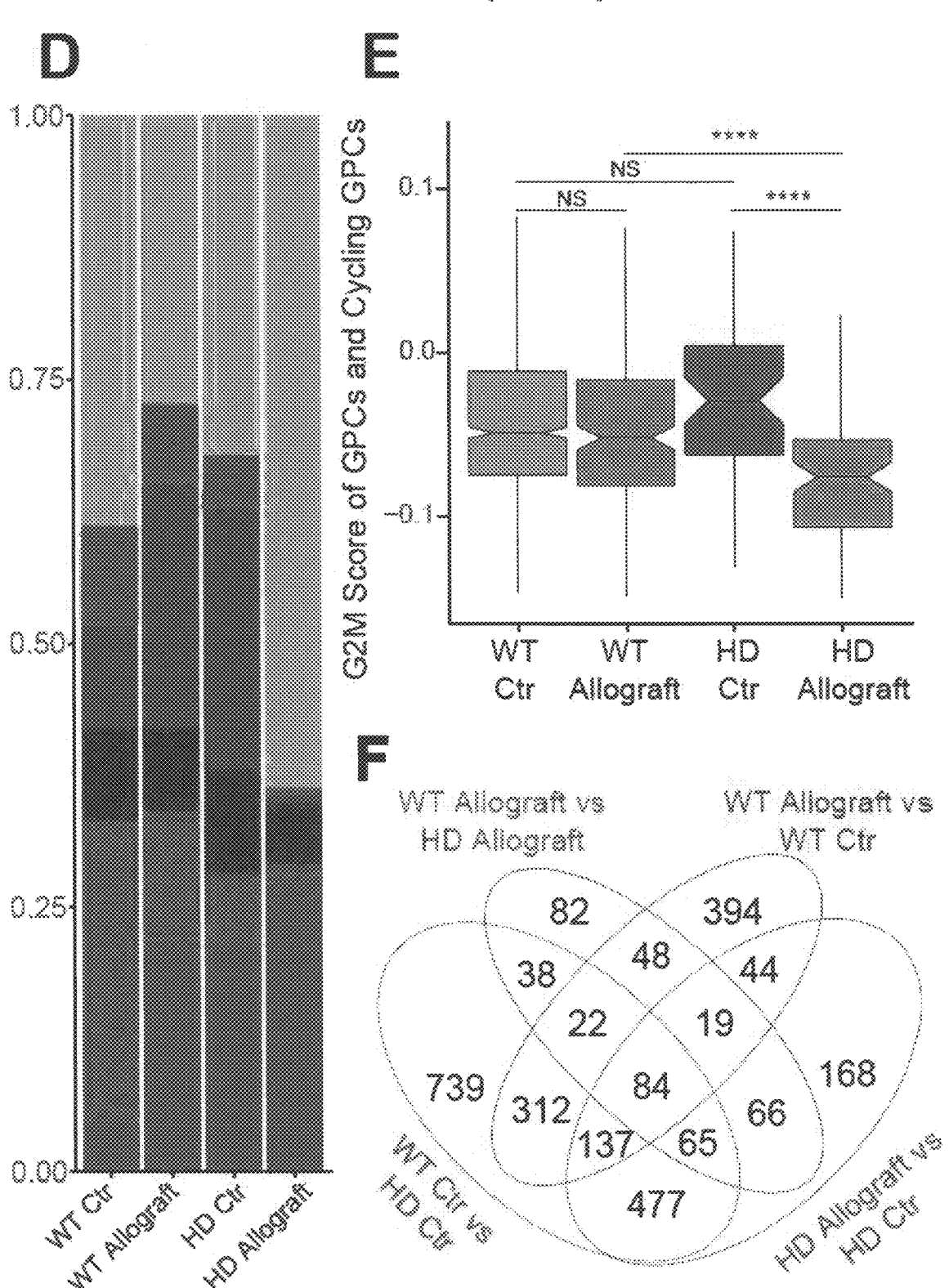
Figure 19:
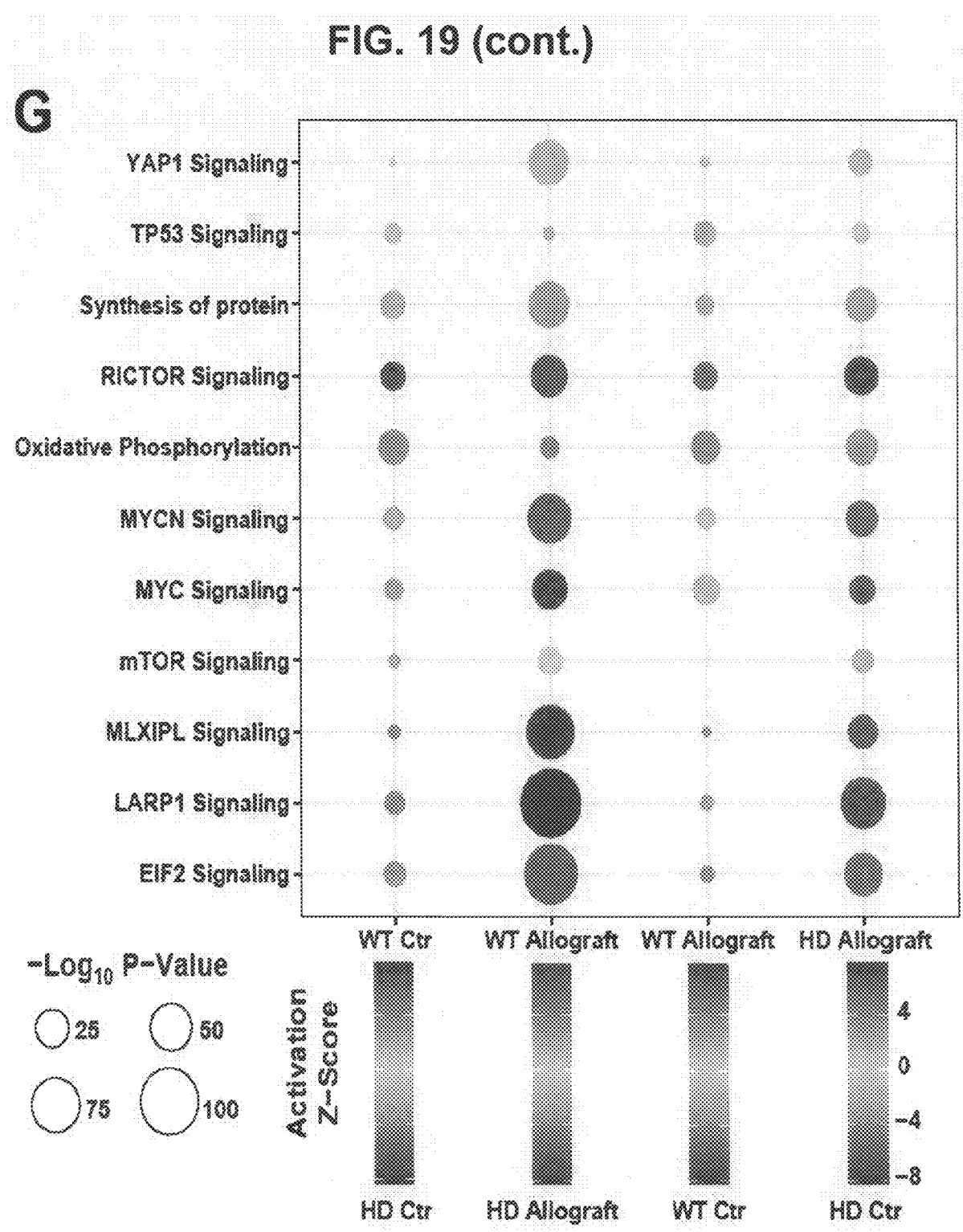
Figure 19:
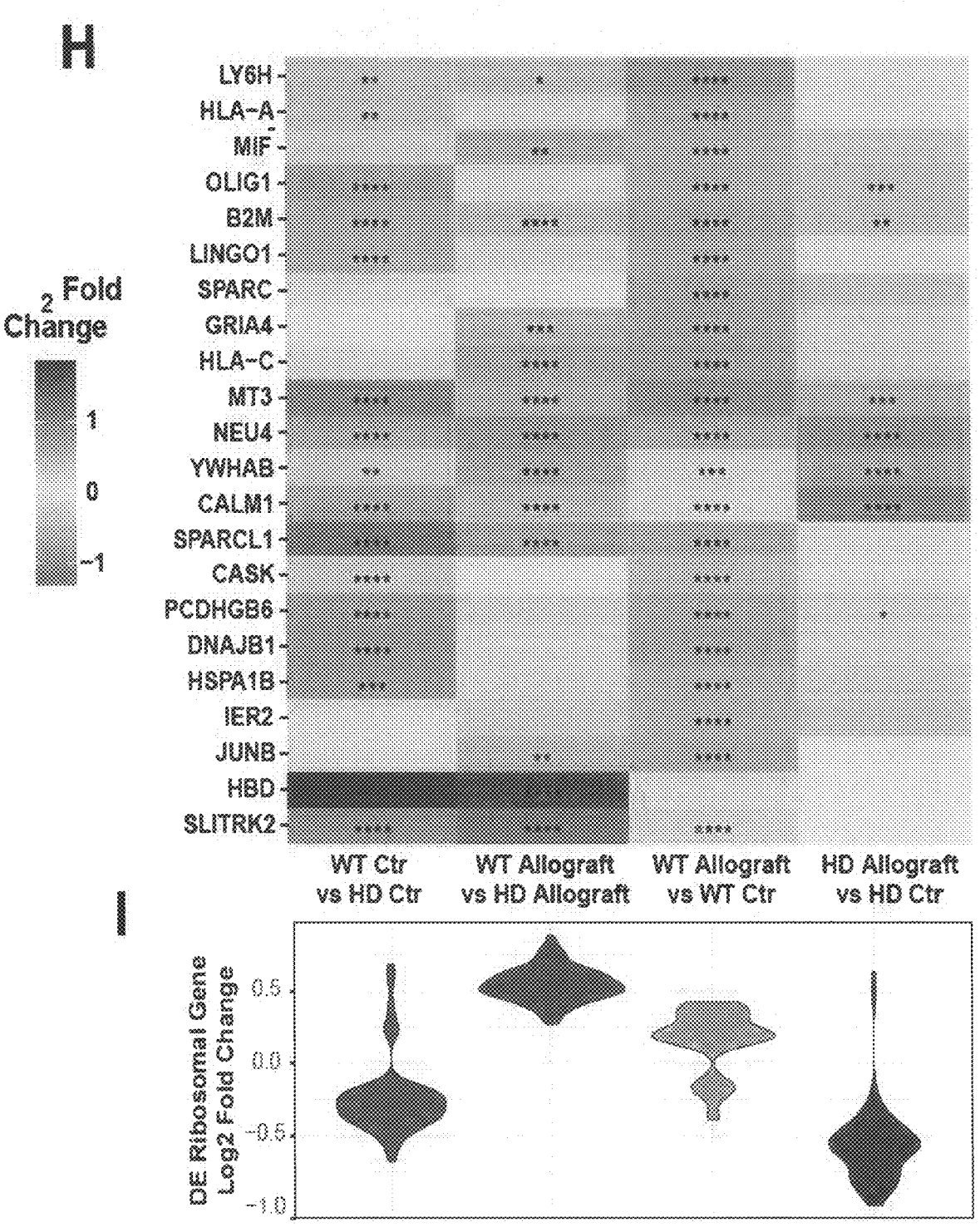

Example 6: Human WT Glia Assume a Dominant Competitor Profile when Encountering HD Glia Having established that implanted WT hGPCs effectively colonize the HD glial chimeric striata at the expense of the resident mHTT-expressing glia, it was next sought to define the molecular signals underlying their competitive dominance. To that end, the transcriptional profiles of WT and HD human glia isolated from the striata of chimeras in which the two cell populations were co-resident and competing were analyzed, as well as from their respective controls in which one or the other was transplanted without the other, using single cell RNA-sequencing (scRNA-seq; 10× Genomics, v3.1 chemistry) (FIG. 19, Panel A). Following integration of all captures and aligning against human sequence, Louvain community detection revealed six major populations of human glia; these included hGPCs, cycling hGPCs, immature oligodendrocytes (iOL), neural progenitor cells (NPCs), astrocytes, and their intermediate progenitors (astrocyte progenitor cells, APCs) (FIG. 19, Panels B-D). Within these populations, cell cycle analysis predicted a higher fraction of actively proliferating G2/M phase cells in competing WT cells compared to their HD counterparts (FIG. 19, Panel E), aligning with the histological observations (FIG. 4, Panel J). To proceed, study focused on hGPCs as the primary competing population in the model. Pairwise differential expression revealed discrete sets of differentially expressed genes across groups (FIG. 19, Panel F), and subsequent functional analysis with Ingenuity pathway analysis (IPA) within the hGPC population revealed numerous salient terms pertaining to their competition (FIG. 19, Panel G).

During competition, it was found WT GPCs activate pathways driving protein synthesis, whereas HD GPCs were predicted to downregulate them. Predicted upstream transcription factor activation identified YAP1, MYC, and MYCN—conserved master regulators of cell growth and proliferation—as significantly modulated across experimental groups. Importantly, YAP1 and MYC targets were found to be selectively down-regulated in competing HD GPCs relatively to their controls (FIG. 19, Panel G). Notably, this down-regulation was attended by a marked repression of ribosomal encoding genes (FIG. 19, Panel I). Conversely, competing WT hGPCs showed an upregulation of both YAP1 and MYC targets, as well as in the expression of ribosomal encoding genes, relative to controls (FIG. 19, Panels G-H). As such, these data suggest that the implanted WT hGPCs actively assumed a competitively dominant phenotype upon contact with their HD counterparts, to drive the latter's local elimination while promoting their own expansion and colonization.

Example 7: Age Differences Drive Competitive Human Glial Repopulation

Figure 17:
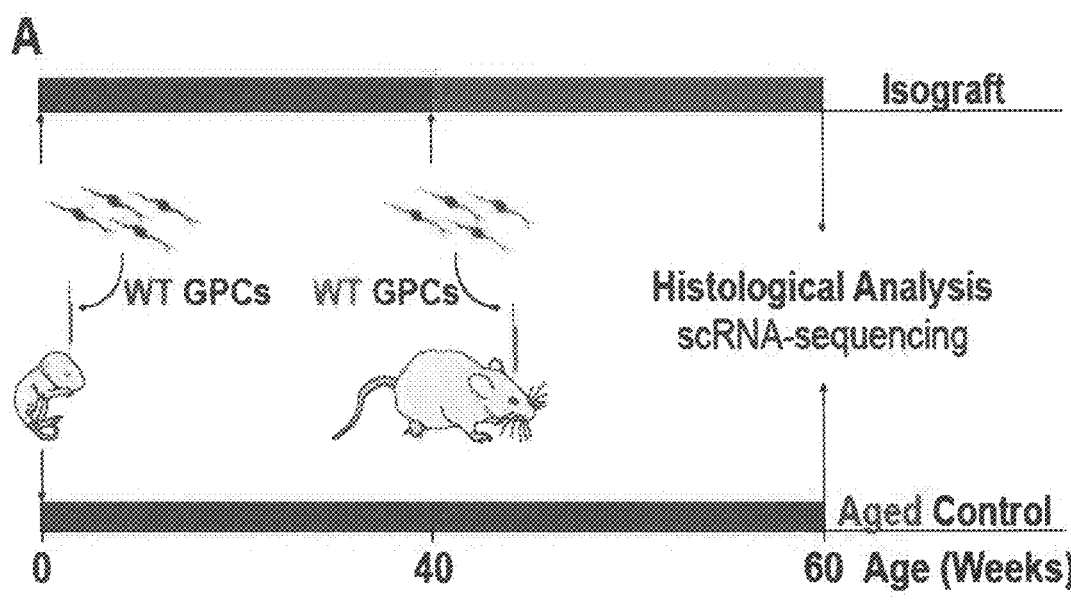
FIG. 17, Panels A-E show differences in cellular age are sufficient to drive competitive glial repopulation. shows differences in cell age are sufficient to drive competitive repopulation of humanized striata. Panel A. Experimental design and analytical endpoints. Panel B. Engraftment of younger WT glia (EGFP+, green) into the striatum of WT chimeras yielded selective replacement of their aged counterparts (mCherry+, red). Dashed outlines demarcate the striatal regions within which human cells were mapped and quantified. Panel C. WT chimeric control, engrafted only at birth. Panel D. Rendered examples of mapped striata. Volumetric quantification shows that the younger WT glia replace their older isogenic counterparts as they expand from their injection site; Panel E. Aged vs. Young (Isograft), n=3. Their advance tracked the progressive elimination of aged WT glia from the tissue, relative to control WT chimeras (Aged control); Panel F. Aged (Isograft) vs. Aged (Control) n=3 each; 2-way ANOVA with Šidák's multiple comparisons test; Interactions or main effects are shown as numerical P values, while post-hoc comparisons are shown as: **P<0.0001, *P<0.001, **P<0.01, *P<0.05; data presented as means±SEM. Panel G. At the interface between young and aged WT glia, a higher incidence of Ki67+ (white) cells can be seen within the younger population. Dashed square represents inset color split (Panel H). Panel I. Quantification of Ki67+ cells shows that younger WT glia are significantly more proliferative than their aged counterparts; n=3 for all experimental groups; One-way ANOVA with Šidák's multiple comparisons test; data are shown as means±SEM with individual data points. Panels B-C. STR, striatum (caudate-putamen); LV, lateral ventricle; CTX, cortex.). Scale: Panel B, 500 µm; Panel C, 100 µm; Panel E, 100 µm; Panel G, 50 µm.
Figure 17:
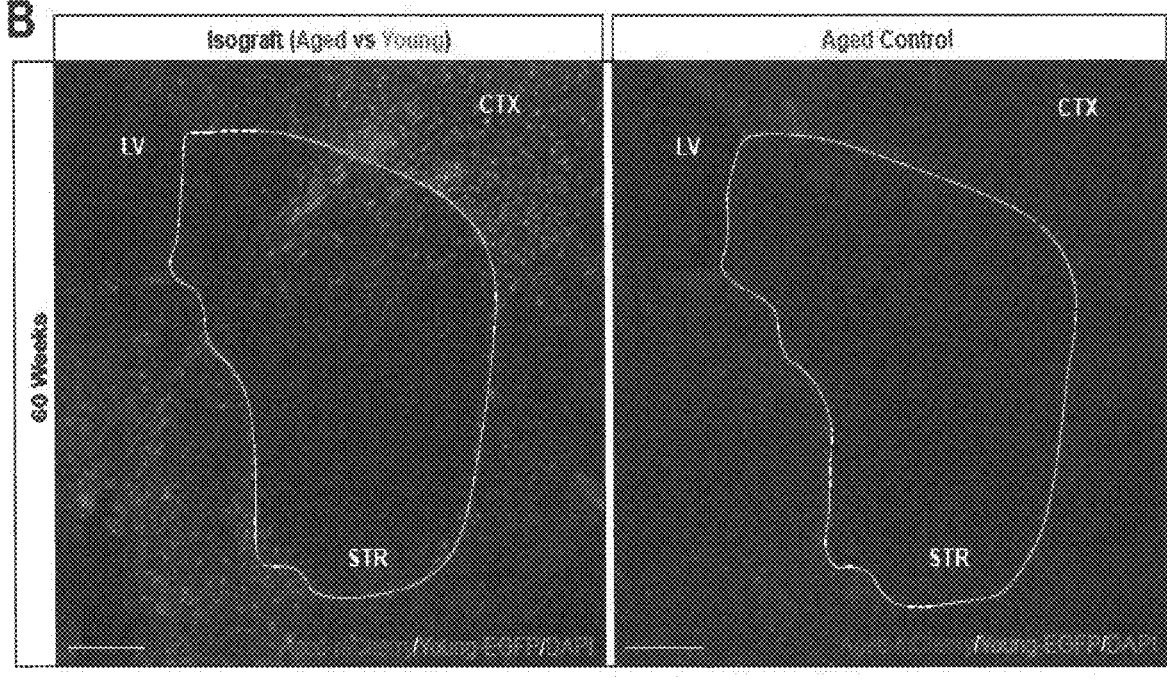
Figure 17:
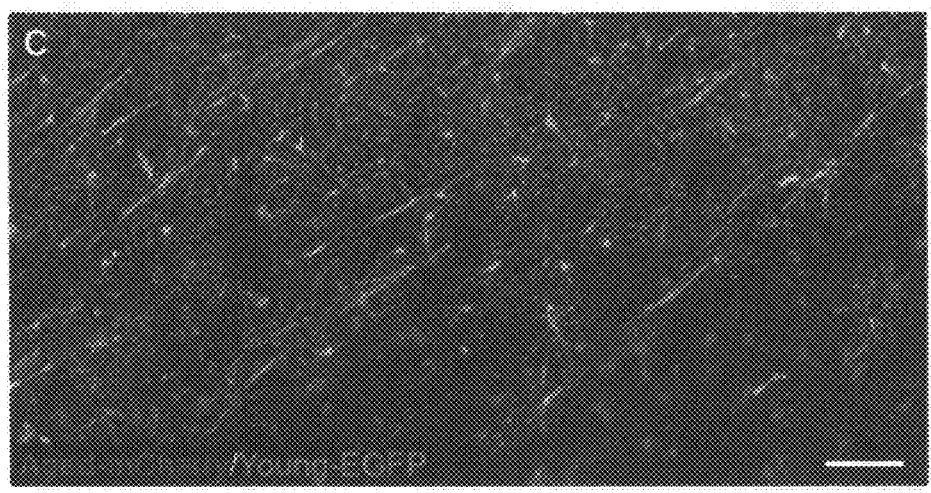
Figure 17:
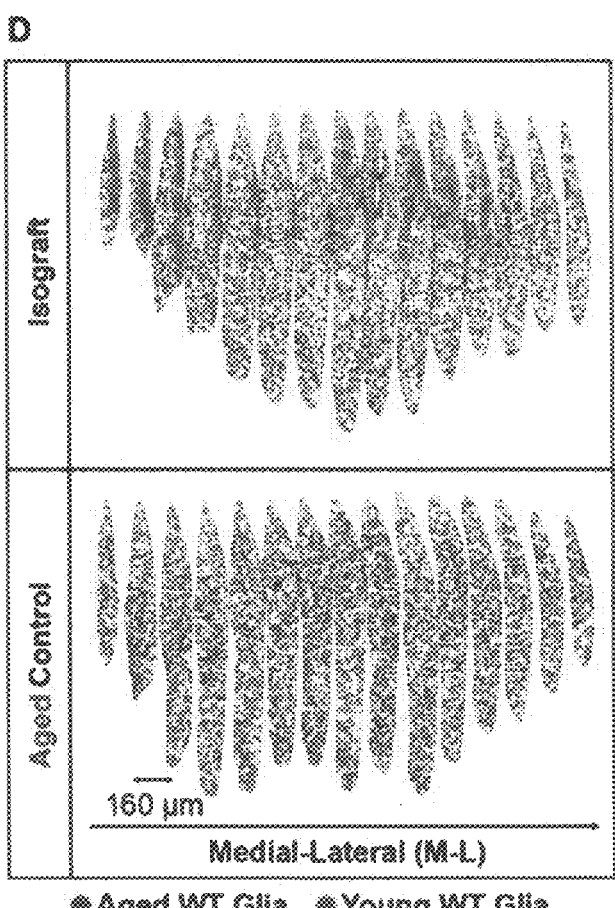
Figure 17:
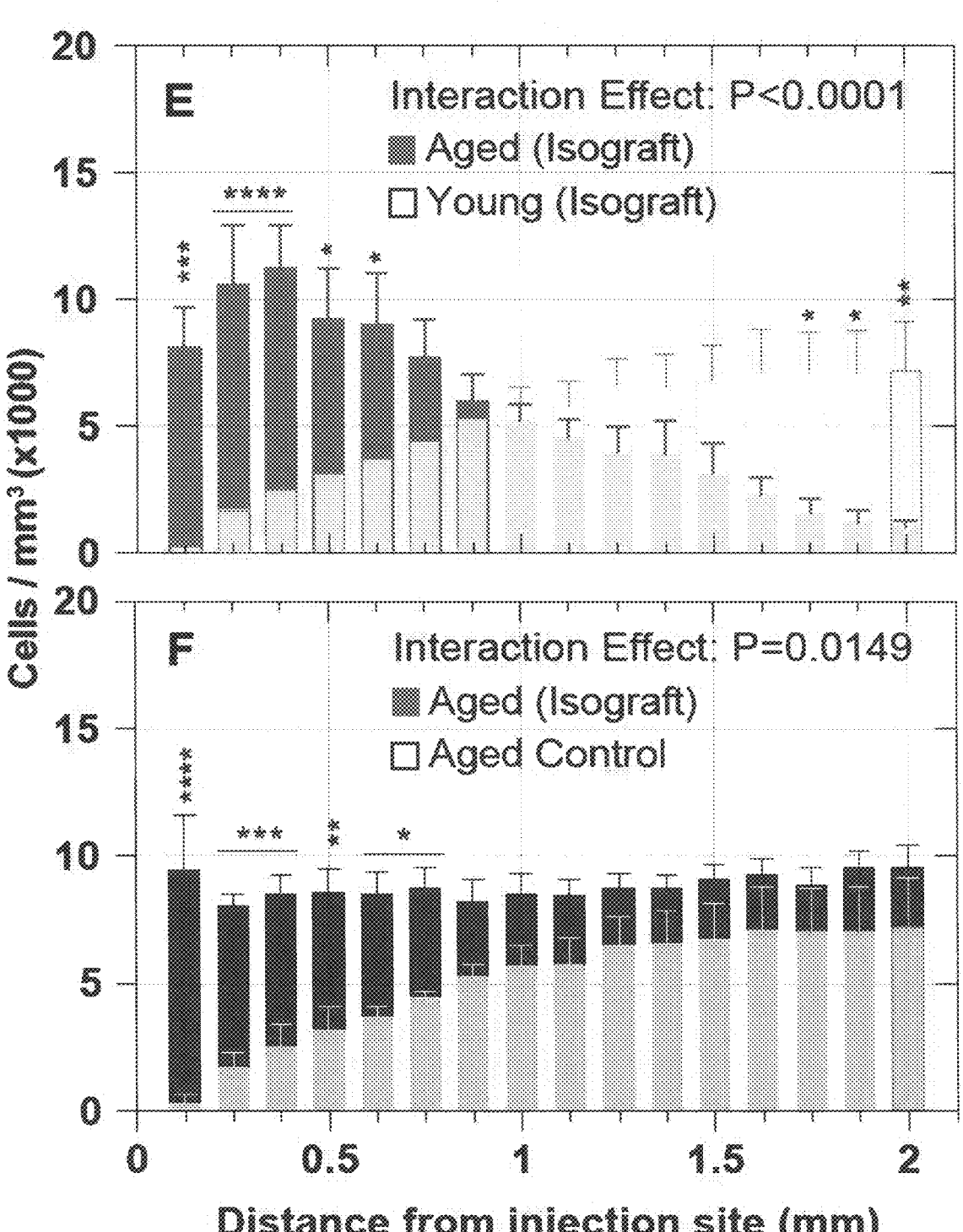
Figure 17:
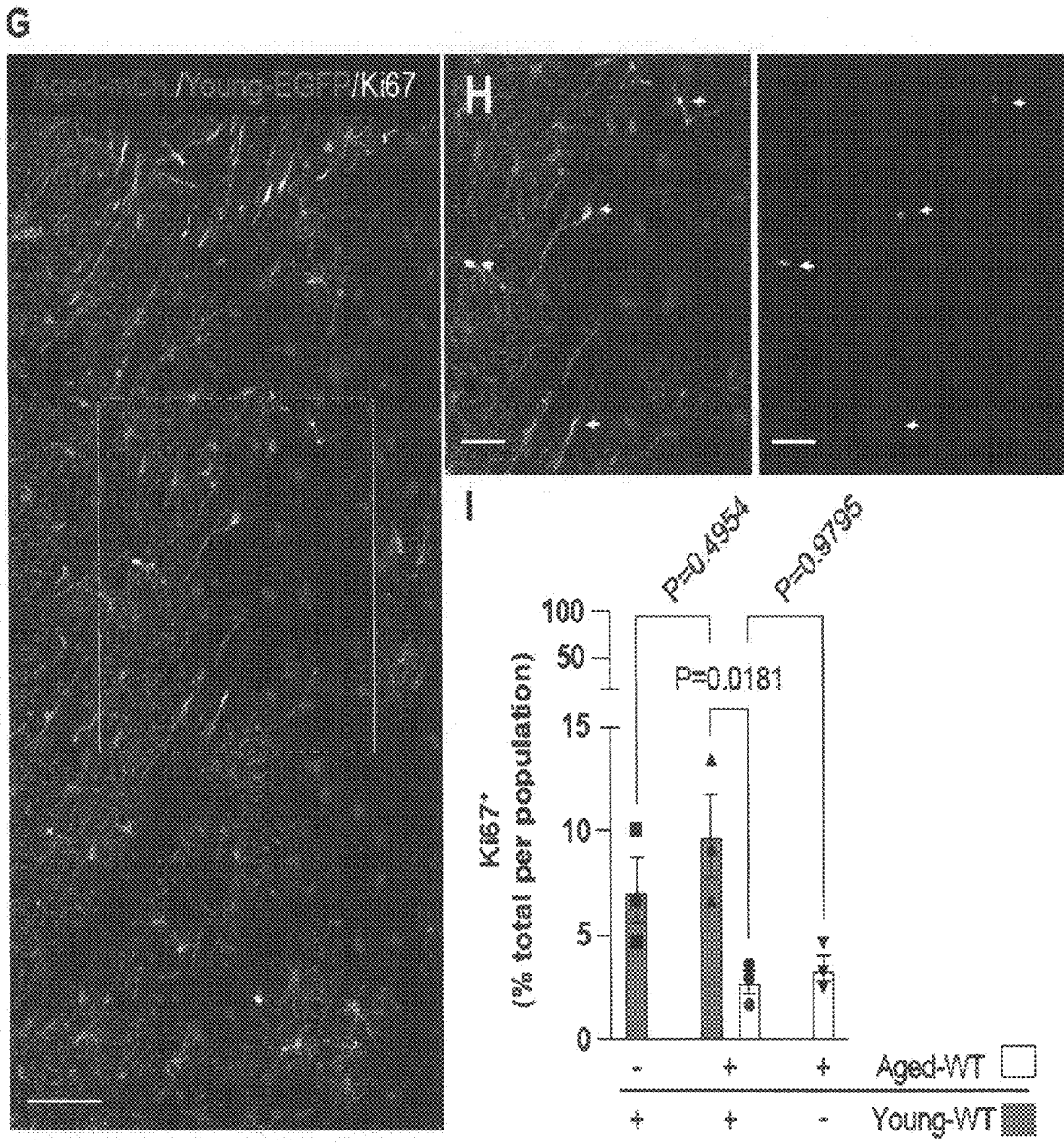

Since WT cells transplanted into adult hosts were fundamentally younger than the resident host cells that they displaced and replaced, it was next asked if differences in cell age, besides disease status, might have contributed to the competitive success of the late donor cells. To that end, engrafted hGPCs newly produced from WT hESCs were engineered to express EGFP into the striata of 40 week-old adult glial chimeras, which had been perinatally engrafted with hGPCs derived from mCherry-tagged, otherwise isogenic WT hESCs (FIG. 17, Panel A). The expansion of the transplanted cells histologically was monitored, so as to map the relative fitness and competitive performance of these isogenic, but otherwise distinctly aged pools of hGPCs.

The expansion of implanted WT glia within the striatum of WT chimeras was strikingly similar to their expansion in the striata of HD chimeras (FIG. 4). Following engraftment, the younger WT glia rapidly infiltrated the previously humanized striatum, progressively displacing their aged counterparts as they expanded from their implantation site, ultimately yielding substantial recolonization of the tissue (FIG. 17, Panels B-D and E; P<0.0001). Their expansion was paralleled by the local elimination of aged WT glia (FIG. 17, Panels B-D and F; P<0.0001), which was also marked by a discrete advancing front, behind which few already-resident WT glia could be found (FIG. 17, Panel C). Accordingly, it was also noted that the mitotic fraction of implanted WT glia was significantly larger than that of their resident aged counterparts (FIG. 17, Panels G-I; P=0.018). Together, these data indicated that the repopulation of the human WT glial chimeric striatum by younger isogenic hGPCs was attended by the replacement of the older cells by their younger counterparts, fueled in part by the relative expansion of the younger, more mitotically active cell population.

Figure 20:
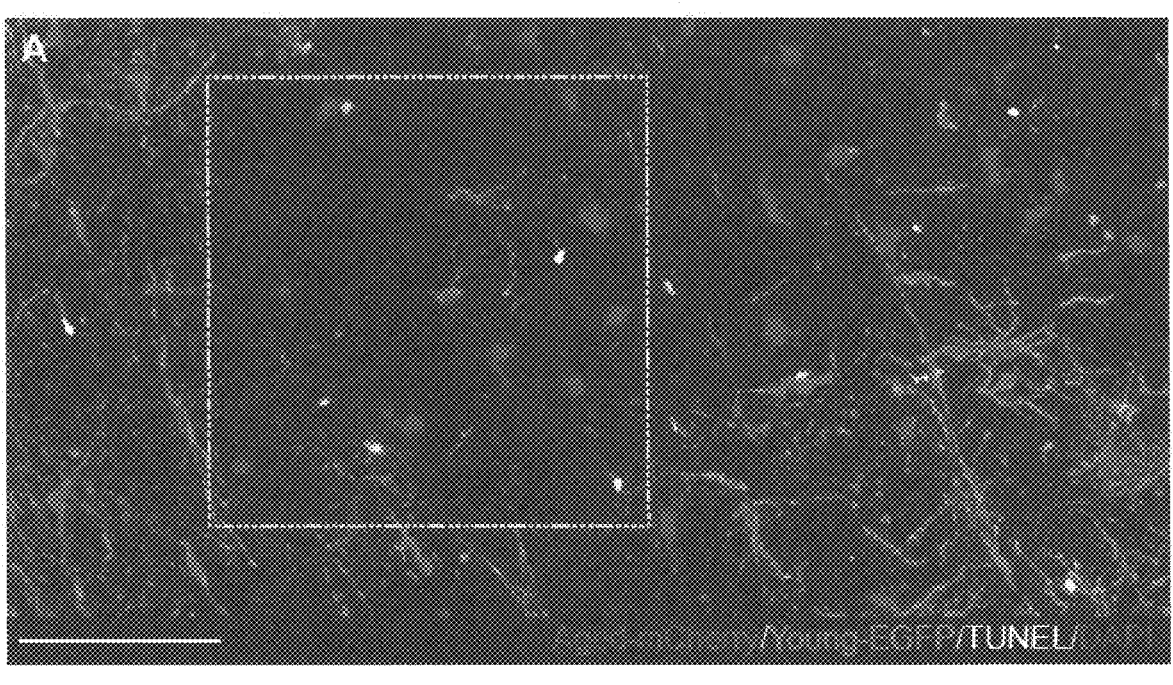
FIG. 20 shows aged human glia are eliminated by their younger counterparts through induced apoptosis. Panel A. At the border between young (EGFP+, green) and aged WT glia (mCherry+, red), a higher incidence of apoptotic TUNEL+ (white) cells are apparent in the aged population. Panel B. Higher magnification of a competitive interface between these distinct populations shows resident glia selectively undergoing apoptosis. Panel C. Quantification of TUNEL+ cells shows significantly higher incidence of TUNEL+ cells among aged resident WT glia, relative to both their younger isogenic counterparts, and to aged WT chimeric controls not challenged with younger cells. Quantification was performed on pooled samples from 60 and 80 weeks timepoints (n=5 for all experimental groups). One-way ANOVA with Šidák's multiple comparisons test; data are shown as means±SEM with individual data points. Scale: Panel A, 100 µm; Panel B, 50 µm.
Figure 20:
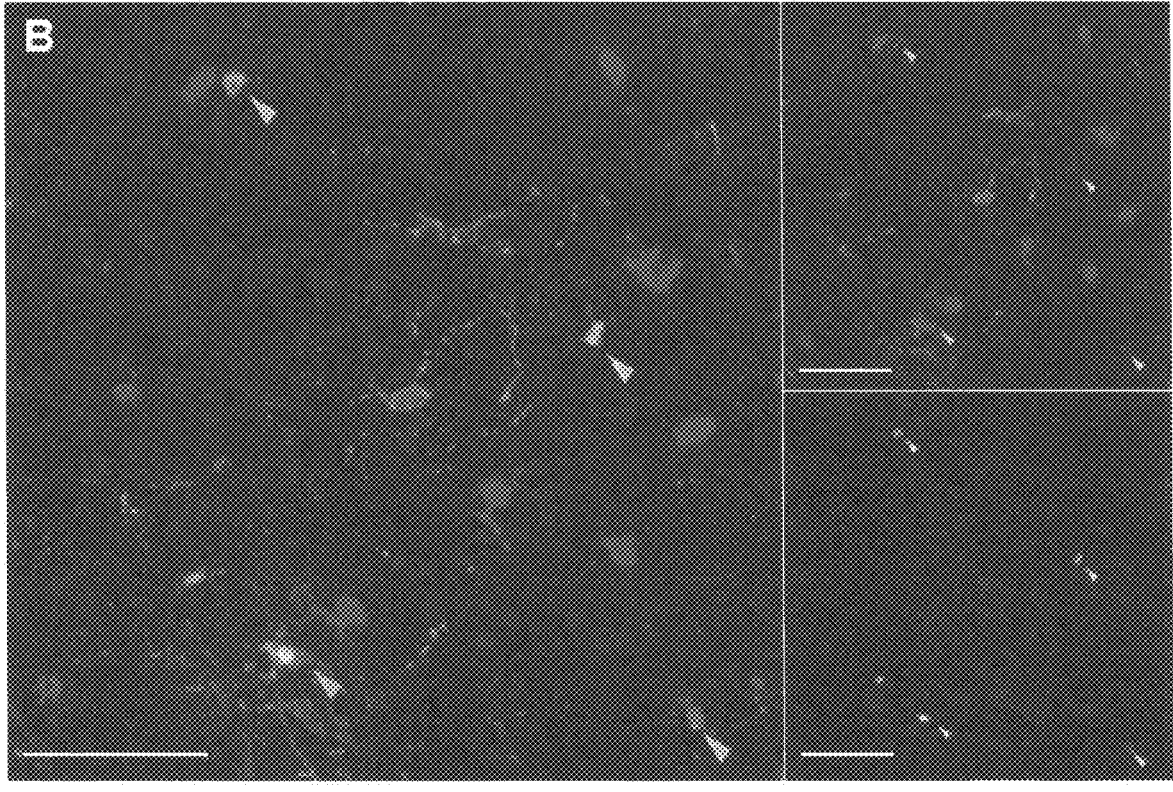
Figure 20:
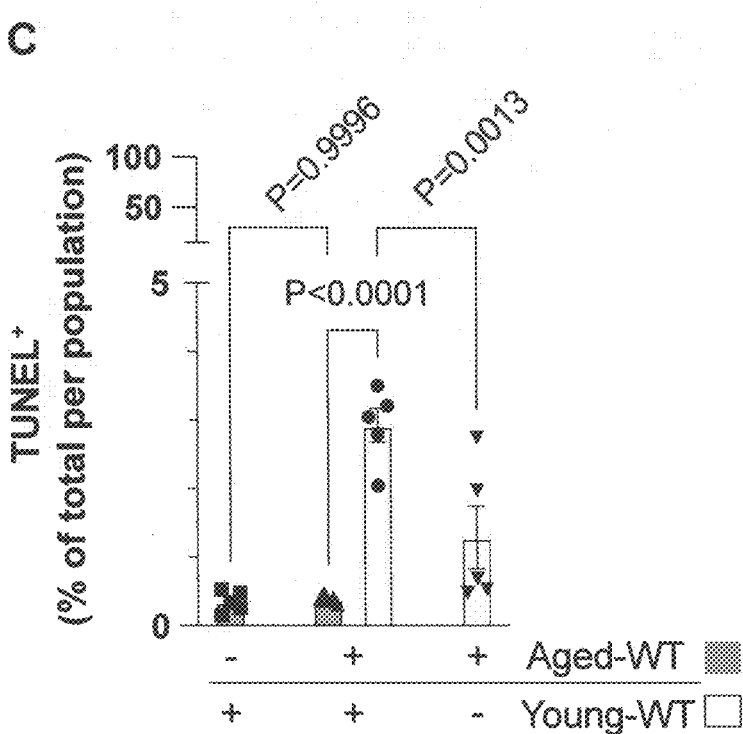

Example 8: Young Cells Replace their Older Counterparts Via the Induction of Apoptosis Since younger glia appeared to exert clear competitive dominance over their older counterparts, it was next asked whether the elimination of the older glia by younger cells occurred passively, as a result of the higher proliferation rate of the younger cells leading to the relative attrition of the older residents during normal turnover, or whether replacement was actively driven by the induction of programmed cell death in the older cells by the more fit younger cells. To address this question, the TUNEL assay was used to compare the rates of apoptosis in aged and young WT glial populations as they competed in the host striatum, as well as at their respective baselines in singly-transplanted controls. It was found that as competitive repopulation unfolded, that aged WT glia underwent apoptosis at a markedly higher rate than their younger counterparts (FIG. 20, Panels A-C; P<0.0001). Critically, the increased apoptosis of older, resident glia appeared to be driven by their interaction with younger cells, since a significantly higher proportion of aged glia was found to be apoptotic in chimeras transplanted as adults with younger cells, than in controls that did not receive the later adult injection (FIG. 30, Panel C; P=0.0013). These data suggest that aged resident glia confronted by their younger counterparts are actively eliminated, at least in part via apoptosis triggered by their encounter with the younger hGPCs, whose greater relative fitness permitted their repopulation of the chimeric host striatum.

Figure 21:
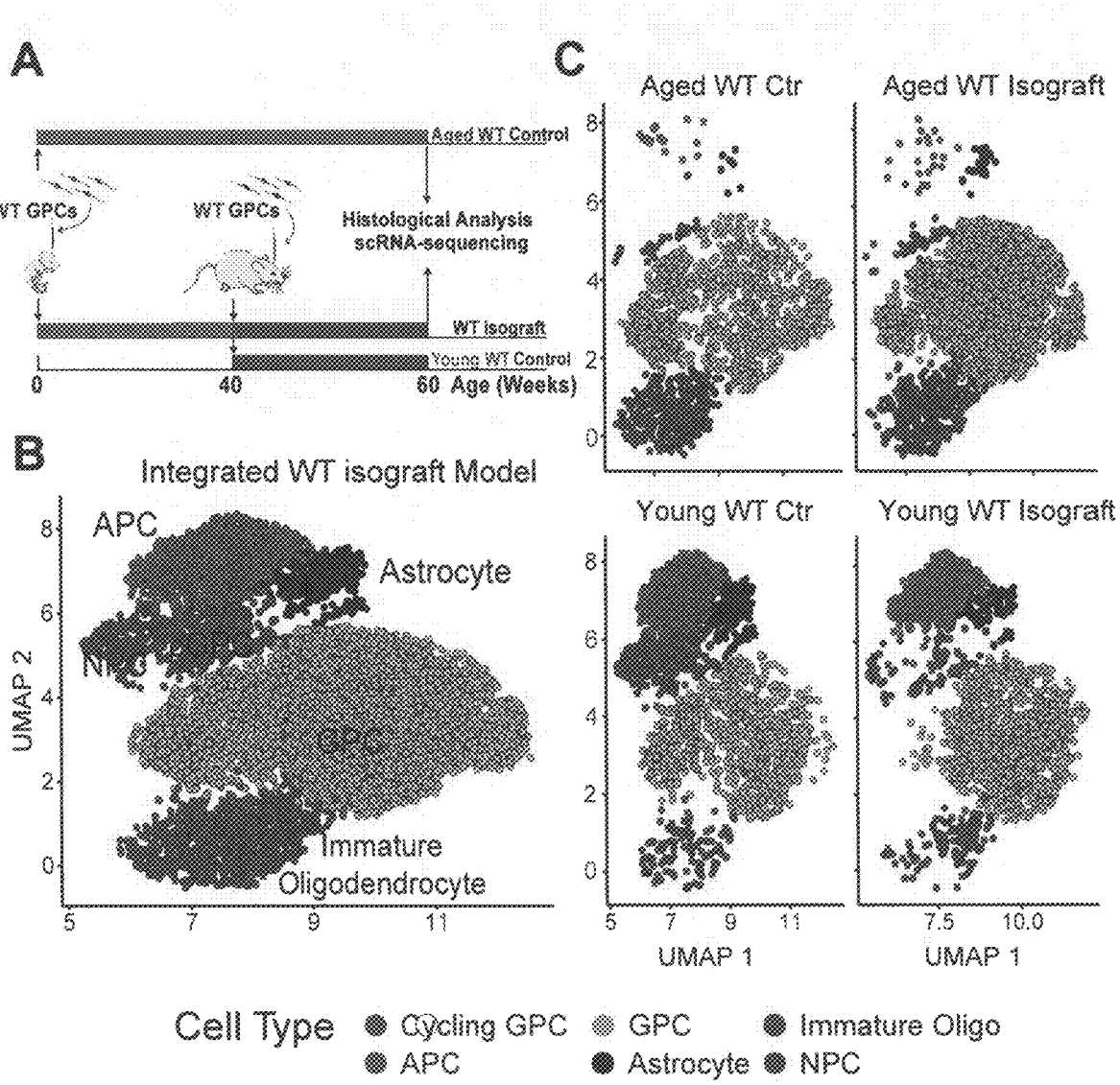
FIG. 21 shows WT glia acquire a dominant transcriptional profile when confronting their aged counterparts. Panel A. Experimental design. Panel B-C. Uniform manifold approximation projection (UMAP) visualization of the integrated (Panel B) and split by group (Panel C) scRNA-seq data identifies six major cell populations. Panel D. Stacked bar plot proportions of cell types in each group. Panel E. Cell cycle analysis notched box plots of cycling GPCs and GPCs in the G2/M phase. The box indicates the interquartile range, the notch indicates the 95% confidence interval with the median at the center of the notch, and the error bars represent the minimum and maximum non-outlier values. Panel F. Venn diagram of pairwise differentially expressed GPC genes (Log 2 fold change>0.15, adjusted p-value<0.05). Panel G. Curated Ingenuity Pathway analysis of genes differentially expressed between GPC groups. The size of circles represents p-value while the shading indicates activation Z-Score with red being more active in the upper group and green being more active in the lower group. Panel H. Heatmap of curated pairwise differentially expressed GPC genes. Panel I. Violin plots of pairwise differentially expressed GPC ribosomal gene log 2 fold changes. Comparisons between groups in E utilized Dunn tests, following a Kruskal-Wallis test with multiple comparisons adjusted via the Benjamini-Hochberg method. *=<0.05, <0.01, *=<0.001, ****=<0.0001 adjusted p-value.
Figure 21:
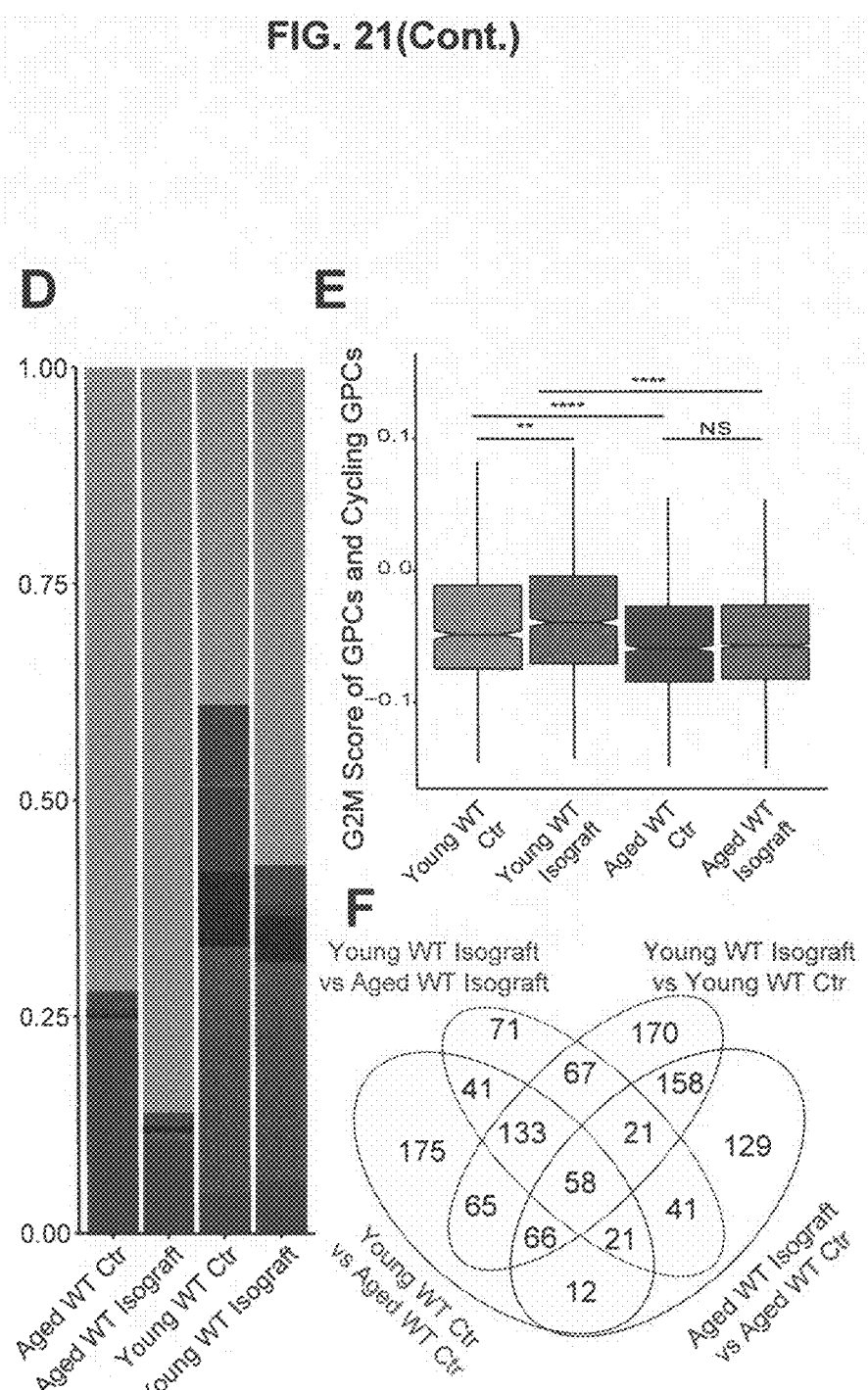
Figure 21:
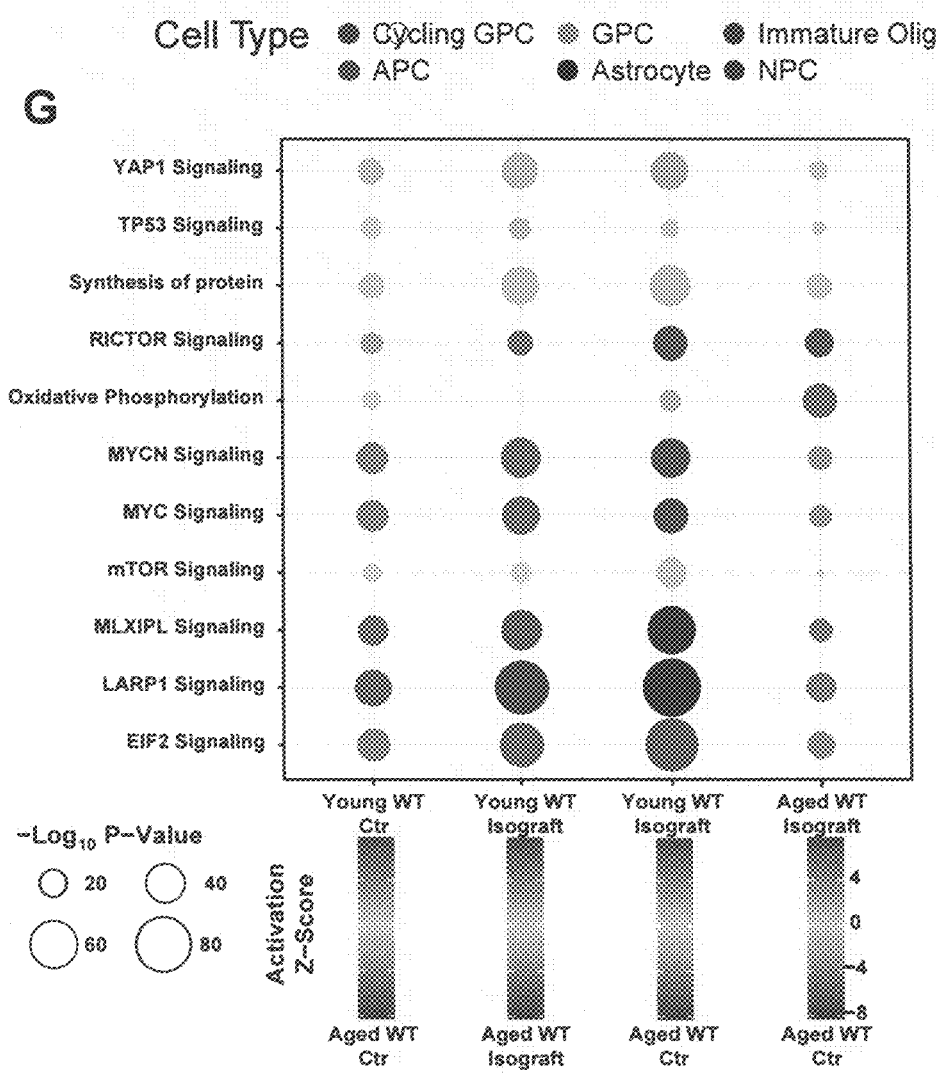
Figure 21:
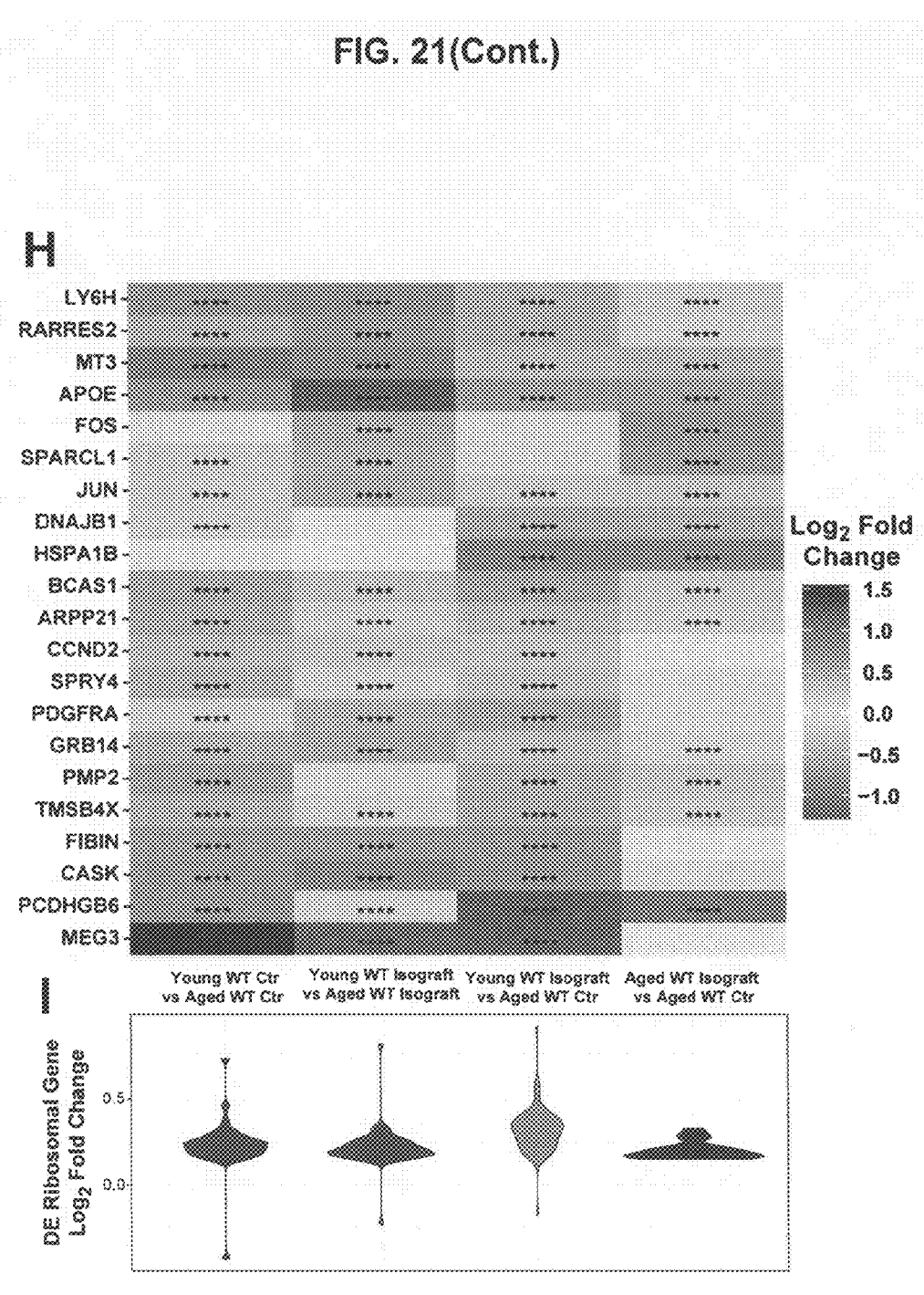

Example 9: Young hGPCs Acquire a Signature of Dominance when Challenged with Older Isogenic Cells To ascertain if the molecular signals underlying the competitive dominance of younger WT glia over aged WT glia are similar to those underlying their dominance over HD glia, the transcriptional signatures of competing young and aged WT glia and their respective controls were analyzed, using scRNA-seq (FIG. 21, Panel A). Within the sequenced populations (FIG. 21, Panel B-D), it was noted that the fraction of competing aged WT cells in the G2/M phase of the cell cycle to be markedly lower than their younger counterparts (FIG. 21, Panel E), in accord with the histological data (FIG. 17, Panel I). Differential expression analysis revealed discrete sets of genes differentially expressed between competing young and aged WT GPCs (FIG. 21, Panel F and H), and subsequent IPA analysis of those gene sets revealed a signature similar to that observed between donor (young) WT and already-resident (aged) HD GPCs in our competitive allograft model (FIG. 21, Panel G). In particular, genes functionally associated with protein synthesis, including ribosomal genes as well as upstream YAP1, MYC and MYCN signaling, were all activated in competing young WT GPCs relative to their aged counterparts (FIG. 21, Panel G). Yet despite these similarities, in other respects aged WT GPCs responded differently than did HD GPCs to newly implanted WT GPCs. In contrast to HD GPCs, aged WT cells confronted with younger isogenic competitors upregulated both YAP1 and MYC targets relative to their non-competing controls (FIG. 21, Panel G) with a concomitant upregulation of ribosomal genes (FIG. 21, Panel I). This difference in their profiles may represent an intrinsic capacity to respond competitively when challenged, which mHTT-expressing HD hGPCs lack. Nonetheless, this upregulation was insufficient to match the greater fitness of their younger counterparts, which similarly—but to a relatively greater degree—manifested the selective upregulation of YAP1 and MYC targets, as well as ribosomal genes, relative to their non-competing controls (FIG. 21, Panels G-H). Together, these data indicate that the determinants of relative cell fitness may be conserved across different scenarios of challenge, and that the outcomes of the resultant competition are heavily influenced by the relative ages of the competing populations.

Figure 22:
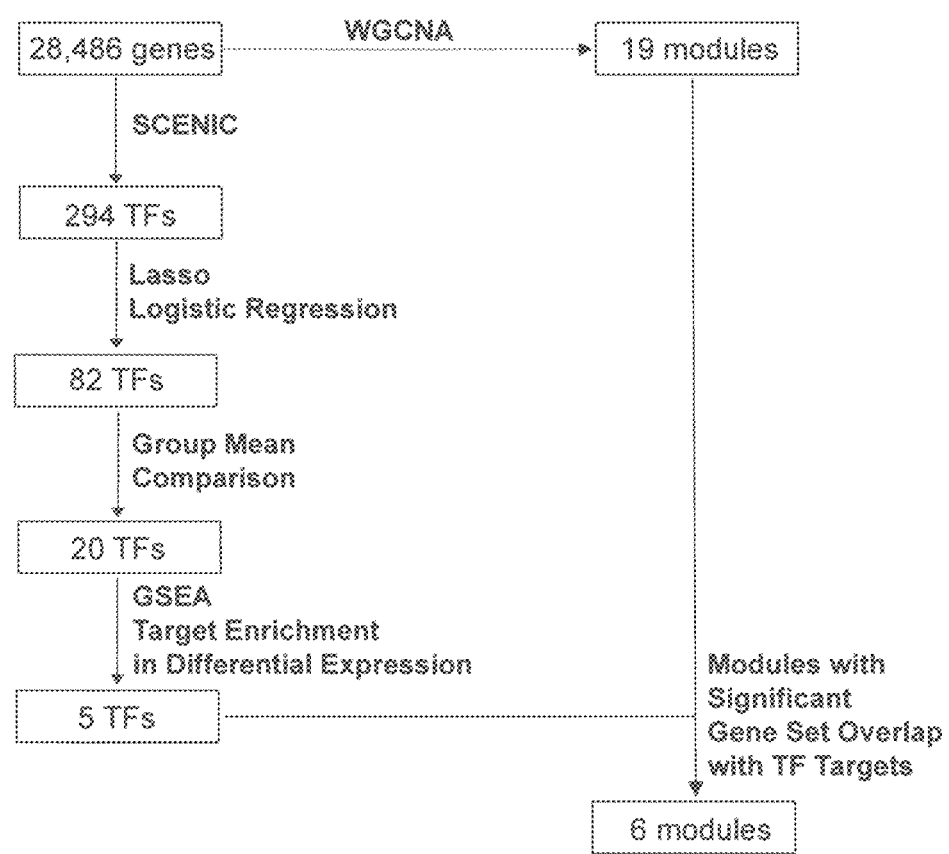
FIG. 22 shows transcriptional signature of competitive advantage. Panel A. Schematic of transcription factor candidate identification. Panel B. Violin plots of identified WGCNA module eigengenes per condition. Represented are significant modules (black, green, blue, brown, red, cyan), whose members are enriched for the downstream targets of the five transcription factors in Panel E. Panel C. Relative importance analysis to estimate the differential contribution of each biological factor (age vs genotype) to each module eigengene. Panel D. Gene set enrichment analysis (GSEA) highlighted those prioritized transcription factors whose regulons were enriched for upregulated genes in dominant young WT cells. Panel E. Important transcription factors predicted via SCENIC to establish competitive advantage and their relative activities across groups. Panel F. Regulatory network with represented downstream targets and their functional signaling pathways. Targets belong to highlighted modules in Panel B, and their expressions are controlled by at least one other important transcription factor in Panel E. NES: Network enrichment score.
Figure 22:
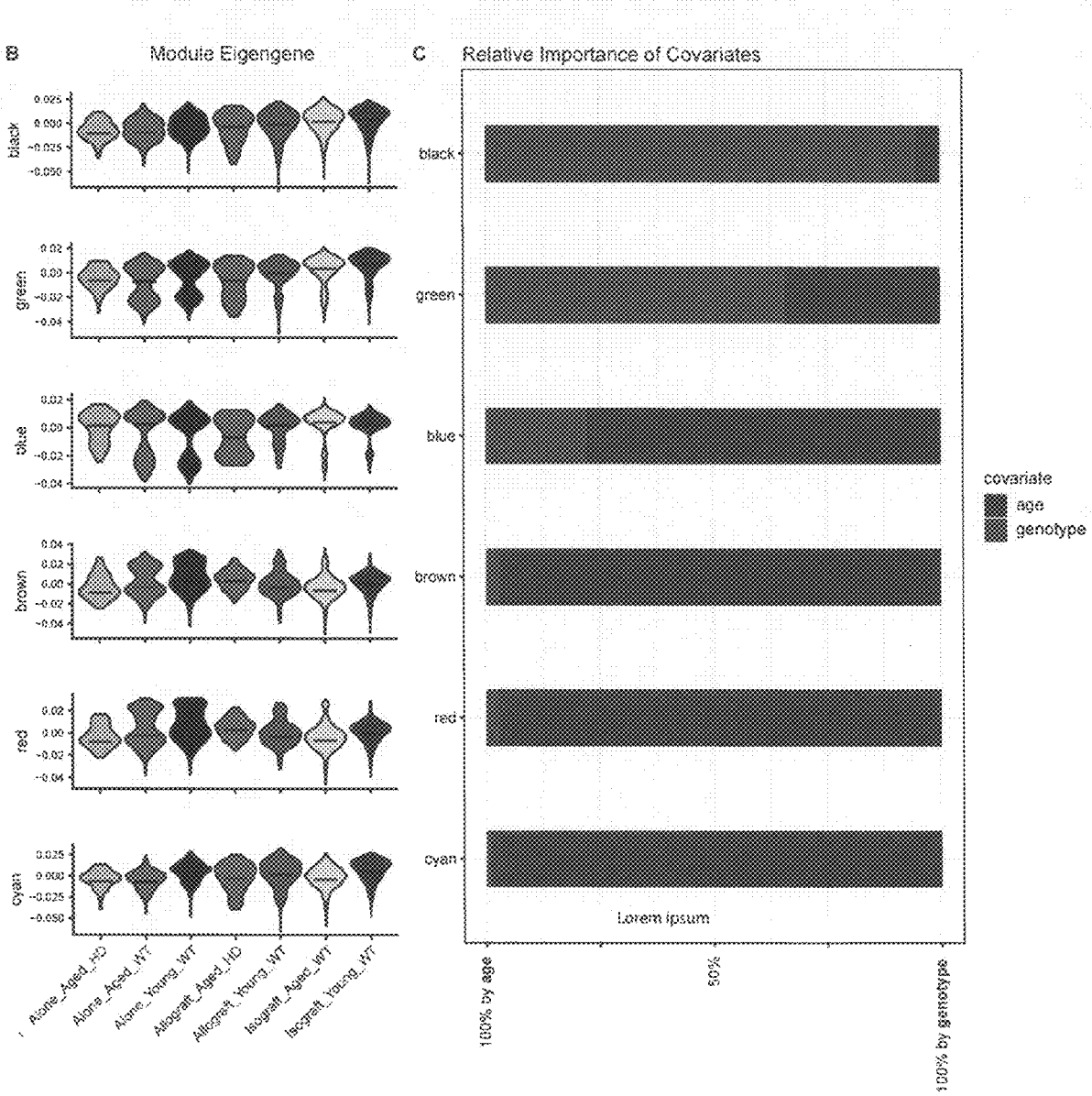
Figure 22:
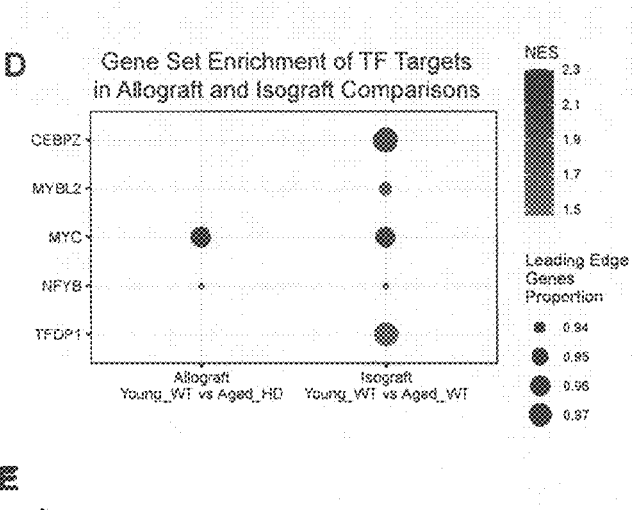
Figure 22:
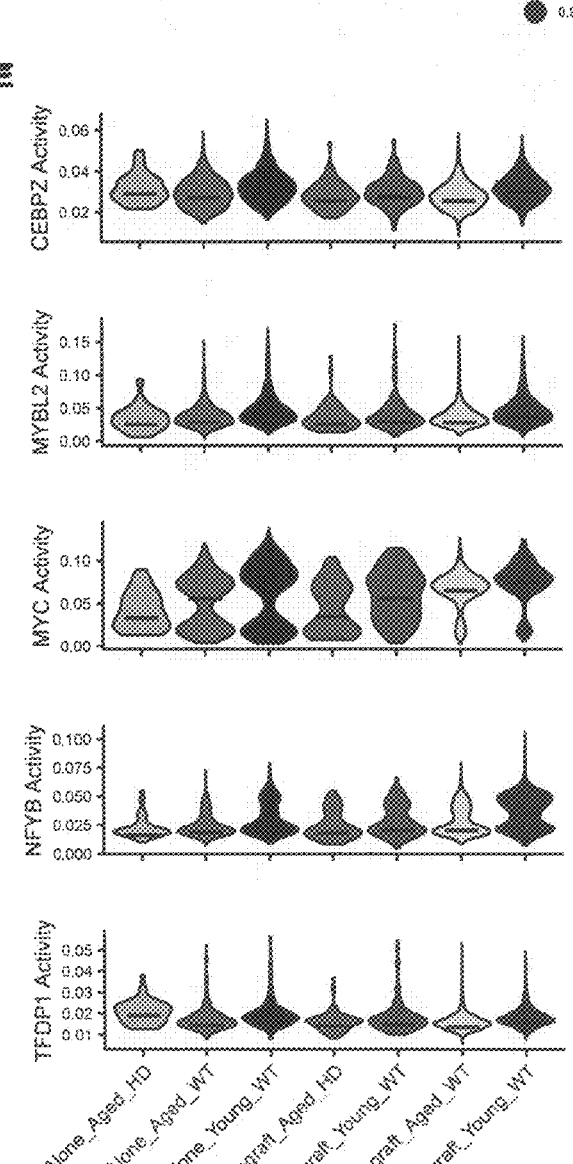
Figure 22:
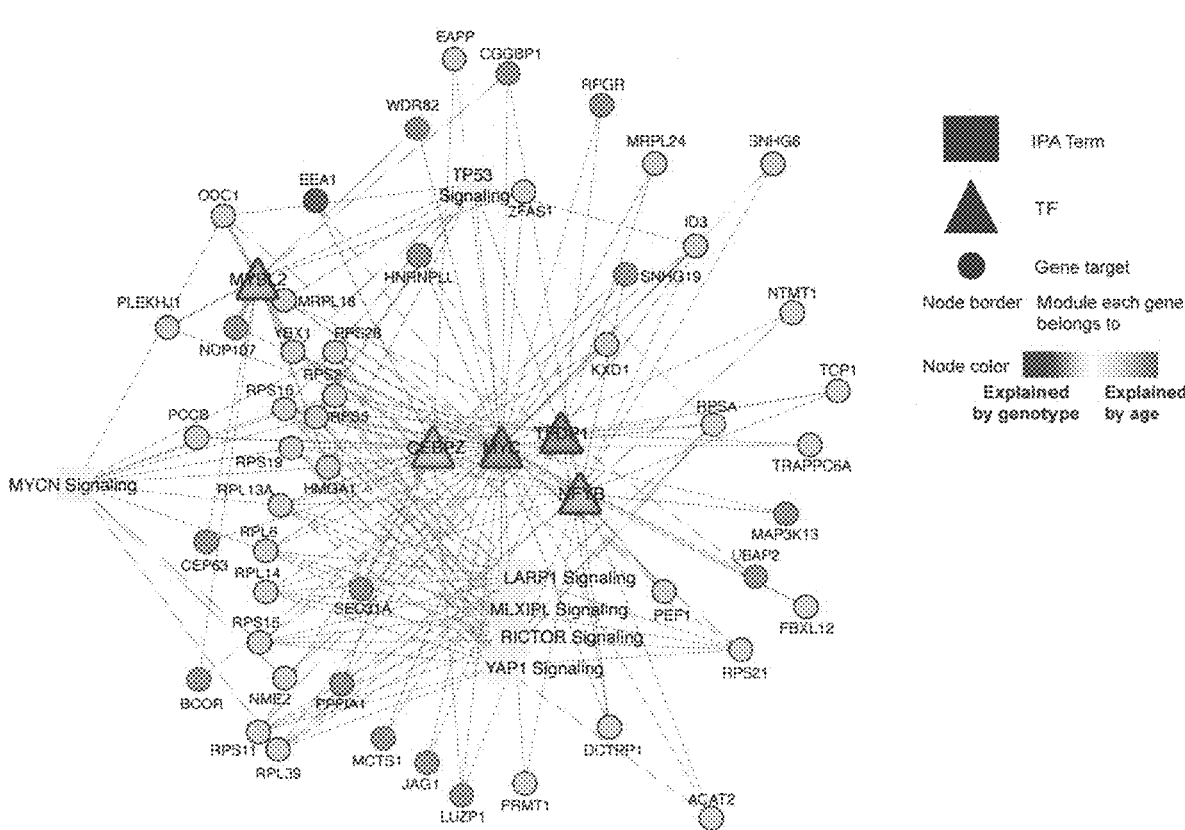

Example 10: Competitive Advantage is Linked to a Discrete Set of Transcription Factors It was next asked what gene signatures would define the competitive advantage of newly-transplanted human GPCs over resident cells. To that end, a multi-stepped analysis using lasso-regulated logistic regression was applied (FIG. 22, Panel A), that pinpointed 5 TFs (CEBPZ, MYBL2, MYC, NFYB, TFDP1) whose activities could significantly explain the dominance of young WT GPCs over both aged HD and aged WT GPCs. These 5 TFs and their putative targets established gene sets (regulons) which were upregulated (normalized enrichment score [NES]>0, adjusted $p<10-2$) in the young WT cells, in both the allograft and isograft models (FIG. 22, Panel D). It was also noticed that while their activities varied when not in a competitive environment (aged HD, aged WT, young WT alone), their mean activities were higher in the dominant young WT cells in both allograft (vs HD) and isograft (vs older isogenic self) paradigms, especially so for MYC (FIG. 22, Panel E).

Next, it was set out to identify cohorts of genes with defined expression patterns, as well as significant overlaps to the five prioritized regulons above. Weighted gene co-expression network analysis (WGCNA) was first employed to detect a total of 19 modules in the GPC dataset (FIG. 22, Panel A). Six modules harbored genes with significant overlap to the targets of CEBPZ, MYBL2, MYC, NFYB, and TFDP1 (FIG. 22, Panel B). It was then asked if the expression pattern of prioritized modules could be explained by the age of cells (young vs. old), by their genotype (HD vs. WT), or both. WGCNA defines module eigengene as the first principal component of a gene cohort, representing thereby the general expression pattern of all genes within that module. As such, linear models were built where module eigengene was a response that was described by both age and genotype. It was observed that modules brown, red, and cyan were mostly influenced by age, while modules black, blue, and green were influenced by both age and genotype (FIG. 22, Panel C).

MYC, whose regulated pathway activation had already been inferred as conferring competitive advantage, was also one of the five prioritized TFs. The MYC regulon and its downstream targets were further characterized, and it was noticed how these downstream targets were also regulated by the other prioritized TFs (FIG. 22, Panel F). Interestingly, while MYC localized to module brown, a large proportion of its targets belonged to module blue. The blue module genes were similarly expressed in the non-competing control paradigms, but their expression levels were higher in the young WT compared to the aged HD in the WT vs HD allograft paradigm (FIG. 22, Panel B), a pattern suggesting that the blue signature was not activated unless cells were in a competing environment. Furthermore, lower expression of these genes was noted in the aged HD relative to the aged WT hGPCs (FIG. 22, Panel E-F), which may highlight the intrinsically greater capacity of WT cells to compete, congruent with the earlier observation that aged WT hGPCs respond differently than HD hGPCs when challenged with newly-engrafted WT GPCs. Importantly, the blue module eigengene could be described by both genotype and age, demonstrating that the competitive advantage associated with MYC signaling was driven by both of these variables. Accordingly, the targets in this network were enriched for pathways regulating cell proliferation (TP53, RICTOR, YAP), gene transcription (MYCN, MLXIPL), and protein synthesis (LARP1), each of which had been previously noted as differentially-expressed in each competitive scenario (FIGS. 19 and 21). As such, the output of this competition-triggered regulatory network appeared to confer competitive advantage upon young WT hGPCs when introduced into the adult brain, whether confronted by older HD-derived or isogenic hGPCs.

While various embodiments have been described above, it should be understood that such disclosures have been presented by way of example only and are not limiting. Thus, the breadth and scope of the subject compositions and methods should not be limited by any of the above-described exemplary embodiments, but should be defined only in accordance with the following claims and their equivalents.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the components and steps in any sequence which is effective to meet the objectives there intended, unless the context specifically indicates the contrary.

wherein at least some of the second human glial cells induce apoptosis of some of the first human glial cells.

2. The method of claim 1, wherein the first population of human glial progenitor cells are human disease-specific glial progenitor cells and wherein the second population of human glial progenitor cells are healthy human glial progenitor cells.

---

---

What is claimed is:

1. A method for producing a chimeric non-human mammal comprising human glial cells, the method comprises the steps of:

firstly introducing a first population of human glial progenitor cells into the brain and/or brain stem of a non-human mammal, wherein the first population of human glial progenitor cells are tagged with a first detectable label;

secondly introducing a second population of human glial progenitor cells into the brain and/or brain stem of the non-human mammal, wherein the second population of human glial progenitor cells are tagged with a second detectable label that is distinguishable from the first detectable label;

thirdly recovering, as a result of said introducing, the chimeric non-human mammal with human glial cells comprising combination of first human glial cells that are (1) derived or differentiated from the first population of human glial progenitor cells and (2) tagged with the first detectable label, and second human glial cells that are (1) derived or differentiated from the second population of human progenitor cells and (2) tagged with the second detectable label, wherein (1) at least 30% of all the glial cells in the corpus callosum of the chimeric non-human mammal are human glial cells, and/or (2) at least 5% of all of the glial cells in the white matter of the brain and/or brain stem of the chimeric non-human mammal are human glial cells, and 3. The method of claim 2, wherein the human disease-specific glial progenitor cells comprise human neurodegenerative disorder-specific glial progenitor cells, or human neuropsychiatric disorder-specific glial progenitor cells, or human myelin disease-specific glial progenitor cells.

4. The method of claim 2, wherein the human disease-specific glial progenitor cells comprise Huntington's disease-specific glial progenitor cells.

5. The method of claim 1, wherein the second population of human glial progenitor cells are younger than the first population of human glial progenitor cells.

6. A chimeric non-human mammal produced according to the method of claim 1.

7. The chimeric non-human mammal of claim 6 wherein the human glial cells comprise a combination of human disease-specific glial cells and healthy human glial cells, wherein the human disease-specific glial cells are tagged with the first detectable label, and wherein the healthy human glial cells are tagged with the second detectable label.

8. The chimeric non-human mammal of claim 7, wherein the human disease-specific glial cells comprise human neurodegenerative disorder-specific glial cells, or human neuropsychiatric disorder-specific glial cells, or human myelin disease-specific glial cells.

9. The chimeric non-human mammal of claim 7, wherein the human disease-specific glial cells comprise human neurodegenerative disorder-specific glial cells and wherein the human neurodegenerative disorder is selected from the group consisting of Huntington's disease, frontotemporal dementia, Parkinson's disease, multisystem atrophy, and amyotrophic lateral sclerosis.

10. The chimeric non-human mammal of claim 9, wherein the human disease-specific glial cells comprise Huntington's disease-specific glial cells.

11. The chimeric non-human mammal of claim 7, wherein the human disease-specific glial cells comprise human neuropsychiatric disorder-specific glial cells and wherein the human neuropsychiatric disorder is selected from the group consisting of schizophrenia, autism spectrum disorder, and bipolar disorder.

12. The chimeric non-human mammal of claim 7, wherein the human disease-specific glial cells comprise human myelin disease-specific glial cells and wherein the human myelin disease leukodystrophy or a white matter disease.

13. The chimeric non-human mammal of claim 6, wherein the mammal is post-natal.

14. The chimeric non-human mammal of claim 6, wherein the mammal is mouse.

15. The chimeric non-human mammal of claim 6, wherein the mammal is immune-incompetent, immune-deficient, or immune-suppressed.

16. The chimeric non-human mammal of claim 7, wherein the human disease-specific glial cells are derived from human disease-specific glial progenitor cells implanted at a first implantation date, wherein the healthy human glial cells are derived from healthy human glial progenitor cells implanted at a second implantation date, and wherein the first implantation date is the same as the second implantation date.

17. The chimeric non-human mammal of claim 7, wherein the human disease-specific glial cells are derived from human disease-specific glial progenitor cells implanted at a first implantation date, wherein the healthy human glial cells are derived from healthy human glial progenitor cells implanted at a second implantation date, and wherein the first implantation date is earlier than the second implantation date.

18. The chimeric non-human mammal of claim 17, wherein the first implantation date is 30-40 weeks earlier than the second implantation date.

* * * * *

SEQUENCE LISTING

```
Sequence total quantity: 3
SEQ ID NO: 1                moltype = DNA   length = 21
FEATURE                     Location/Qualifiers
misc_feature                1..21
                            note = Synthetic: Dna803
source                      1..21
                            mol_type = other DNA
                            organism = synthetic construct
SEQUENCE: 1
tcgacttccc ctcttccgat g                                          21

SEQ ID NO: 2                moltype = DNA   length = 21
FEATURE                     Location/Qualifiers
misc_feature                1..21
                            note = Synthetic: Dna804
source                      1..21
                            mol_type = other DNA
                            organism = synthetic construct
SEQUENCE: 2
gagcctaggg ccgggattct c                                          21

SEQ ID NO: 3                moltype = DNA   length = 22
FEATURE                     Location/Qualifiers
misc_feature                1..22
                            note = Synthetic: Dna183
source                      1..22
                            mol_type = other DNA
                            organism = synthetic construct
SEQUENCE: 3
ctcaggttct gggagagggt ag                                         22
```